(12) United States Patent
Béliveau et al.

(10) Patent No.: US 11,780,882 B2
(45) Date of Patent: *Oct. 10, 2023

(54) PEPTIDE COMPOUNDS AND PEPTIDE CONJUGATES FOR THE TREATMENT OF CANCER THROUGH RECEPTOR-MEDIATED CHEMOTHERAPY

(71) Applicant: TRANSFERT PLUS, S.E.C., Montréal (CA)

(72) Inventors: Richard Béliveau, Montréal (CA); Borhane Annabi, Brossard (CA); Michel Demeule, Beaconsfield (CA); Alain Larocque, St-Laurent (CA); Jean-Christophe Currie, Repentigny (CA); Cyndia Charfi, La Prairie (CA)

(73) Assignee: Transfert Plus, S.E.C., Montreal (CA)

( * ) Notice: Subject to any disclaimer, the term of this patent is extended or adjusted under 35 U.S.C. 154(b) by 230 days.

This patent is subject to a terminal disclaimer.

(21) Appl. No.: 17/239,544

(22) Filed: Apr. 23, 2021

(65) Prior Publication Data
US 2022/0356209 A1    Nov. 10, 2022

Related U.S. Application Data

(63) Continuation of application No. 15/778,626, filed as application No. PCT/CA2016/051379 on Nov. 24, 2016, now Pat. No. 11,034,727.

(60) Provisional application No. 62/259,178, filed on Nov. 24, 2015.

(51) Int. Cl.
| C07K 7/08 | (2006.01) |
| A61K 47/64 | (2017.01) |
| A61P 35/00 | (2006.01) |
| A61K 31/337 | (2006.01) |
| C07K 1/06 | (2006.01) |
| C07K 14/00 | (2006.01) |
| A61K 38/00 | (2006.01) |

(52) U.S. Cl.
CPC .............. *C07K 7/08* (2013.01); *A61K 31/337* (2013.01); *A61K 47/64* (2017.08); *A61P 35/00* (2018.01); *C07K 1/061* (2013.01); *C07K 14/001* (2013.01); *A61K 38/00* (2013.01)

(58) Field of Classification Search
None
See application file for complete search history.

(56) References Cited

U.S. PATENT DOCUMENTS

| 4,680,338 | A | 7/1987 | Sundoro |
| 5,306,809 | A | 4/1994 | Boon et al. |
| 5,525,491 | A | 6/1996 | Huston et al. |
| 6,759,509 | B1 | 7/2004 | King et al. |
| 7,271,149 | B2 | 9/2007 | Glaesner et al. |
| 7,696,221 | B2 | 4/2010 | Coghlan et al. |
| 8,344,211 | B2 | 1/2013 | Alexandrov et al. |
| 9,161,988 | B2 | 10/2015 | Castaigne et al. |
| 11,034,727 | B2 * | 6/2021 | Béliveau ............. A61K 31/337 |
| 2010/0215683 | A1 | 8/2010 | Doro et al. |
| 2020/0157151 | A1 | 5/2020 | Béliveau et al. |

(Continued)

FOREIGN PATENT DOCUMENTS

| AU | 38888/01 A1 | 11/2001 |
| CA | 2653974 | 2/2008 |
| CA | 2981851 | 10/2016 |

(Continued)

OTHER PUBLICATIONS

Seifert et al. "A unique serine-rich repeat protein (Srr-2) and novel surface antigen (e) associated with a virulent lineage of serotype III *Streptococcus agalactiae*" Microbiology 152:1029-1040. (Year: 2006).*

(Continued)

*Primary Examiner* — Sudhakar Katakam
*Assistant Examiner* — Zachary J Miknis
(74) *Attorney, Agent, or Firm* — Foley & Lardner LLP

(57) ABSTRACT

The present disclosure relates to peptide compounds and conjugate compounds, processes, methods and uses thereof for treating cancer. For example, the compounds can comprise compounds of formula

| $X_1X_2X_3X_4X_5GVX_6AKAGVX_7NX_8FKSESY$ (I) | (SEQ ID NO: 1) |
| $(X_9)_nGVX_{10}AKAGVX_{11}NX_{12}FKSESY$ (II) | (SEQ ID NO: 2) |
| $YKX_{13}LRRX_{14}APRWDX_{15}PLRDPALRX_{16}X_{17}L$ (III) | (SEQ ID NO: 3) |
| $YKX_{18}LRR(X_{19})_nPLRDPALRX_{20}X_{21}L$ (IV) | (SEQ ID NO: 4) |
| IKLSGGVQAKAGVINMDKSESM (V) | (SEQ ID NO: 5) |
| IKLSGGVQAKAGVINMFKSESY (VI) | (SEQ ID NO: 6) |
| IKLSGGVQAKAGVINMFKSESYK (VII) | (SEQ ID NO: 7) |
| GVQAKAGVINMFKSESY (VIII) | (SEQ ID NO: 8) |
| GVRAKAGVRNMFKSESY (IX) | (SEQ ID NO: 9) |
| GVRAKAGVRN(Nle)FKSESY (X) | (SEQ ID NO: 10) |
| YKSLRRKAPRWDAPLRDPALRQLL (XI) | (SEQ ID NO: 11) |
| YKSLRRKAPRWDAYLRDPALRQLL (XII) | (SEQ ID NO: 12) |
| YKSLRRKAPRWDAYLRDPALRPLL (XIII) | (SEQ ID NO: 13) | wherein $X_1$ to $X_{21}$ and n can have various different values and wherein at least one protecting group and/or at least one labelling agent is optionally connected to said peptide compound at an N- and/or C-terminal end.

21 Claims, 41 Drawing Sheets

Specification includes a Sequence Listing.

(56) References Cited

U.S. PATENT DOCUMENTS

| | | | |
|---|---|---|---|
| 2020/0392184 | A1 | 12/2020 | Béliveau et al. |
| 2022/0000971 | A1* | 1/2022 | Béliveau ............... C07K 14/47 |

FOREIGN PATENT DOCUMENTS

| | | |
|---|---|---|
| CN | 102131826 A | 7/2011 |
| CN | 102307904 A | 1/2012 |
| EP | 2 077 278 A1 | 7/2009 |
| EP | 2 740 726 A1 | 6/2014 |
| WO | WO-2008/019187 A2 | 2/2008 |
| WO | WO-2009/132656 A2 | 11/2009 |
| WO | WO-2010/022175 A1 | 2/2010 |
| WO | WO-2010063122 A1 | 6/2010 |
| WO | 2011082290 | 7/2011 |
| WO | 2016164637 | 10/2016 |
| WO | WO-2016/164637 A1 | 10/2016 |

OTHER PUBLICATIONS

Liu et al., "Research progress of progranulin and related diseases of nervous system", Chin J Clinicians, Nov. 15, 2013, pp. 10256-10259, vol. 7, No. 22. (English Abstract).

Petersen et al., "Propeptide cleavage conditions sortilin/neurotensin receptor-3 for ligand binding", The EMBO Journal, Feb. 1, 1999, pp. 595-604, vol. 18, No. 3, European Molecular Biology Organization.

Extended European Search Report issued in European Application No. 21174271.3, dated Oct. 27, 2021, 9 pages.

Abstract of Schmidt et al., "Protein sorting gone wrong—VPS10P domain receptors in cardiovascular and metabolic diseases", Atherosclerosis. Feb. 2016, 245:194-9.

Abstract of M.-C. Bissery, "Preclinical Pharmacology of Docetaxel", European Journal of Cancer, vol. 31A, Suppl 4, pp. 51-56, 1995.

Abstract of Carter et al., "Engineering antibodies for imaging and therapy", Biotechnology 1997, 8:449-454.

Abstract of Mazella et al., "Internalization and recycling properties of neurotensin receptors", Peptides 27 (Aug. 9, 2006), 2488-2492.

Abstract of Pedersen et al., "Comparison of Surface Accessible Residues in Human and Murine Immunoglobulin Fv Domains—Implication for Humanization of Murine Antibodies", J. Mol. Biol. (1994) 235,959-973.

Abstract of Truzzi et al., "Neurotrophins and Their Receptors Stimulate Melanoma Cell Proliferation and Migration", Journal of Investigation Dermatology (2008) 128, 2031-2040.

Vincent et al., "Neurotensin and neurotensin receptors", TiPS—Jul. 1999 (vol. 20).

Akil et al., "Fine-Tuning Roles of Endogenous Brain-Derived Neurotrophic Factor, TrkB and Sortilin in Colorectal Cancer Cell Survival", PloS ONE, Sep. 2011, vol. 6, Issue 9, e25097.

Al-Shawi et al., "ProNGF, Sortilin, and Age-related Neurodegeneration", Ann. N.Y. Acad. Sci. 1119:208-215 (2007).

Altschul et al., "Basic Local Alignment Search Tool", J. Mol. Biol. (May 15, 1990) 215,403-410.

Altschul et al., "Gapped BLAST and PSI-BLAST: a new generation of protein database search programs", Nucleic Acids Research, Jul. 16, 1997, vol. 25, No. 17, 3389-3402.

ASCO—Abstract of Demeule et al., "New docetaxel-peptide conjugate for the treatment of sortilin-positive triple-negative breast cancer", Journal of Clinical Oncology, vol. 37, Issue 15 (May 26, 2019).

BD Transduction Laboratories, Technical Data Sheet "Purified Mouse Anti-Neurotensin Receptor 3" (2008).

JR Bradley, "TNF-mediated inflammatory disease", Journal of Pathology 2008; 214:149-160.

Cao et al., "Tumour vasculogenic mimicry is associated with poor prognosis of human cancer patients: A systemic review and meta-analysis", European Journal of Cancer (Aug. 27, 2013) 49,3914-3923.

Carlo et al., "Sorting receptor sortilin-a culprit in cardiovascular and neurological diseases", J Mol Med (May 18, 2014) 92:905-911.

Chiablaem et al., "Curcumin Suppresses Vasculogenic Mimicry Capacity of Hepatocellular Carcinoma Cells through STAT3 and PI3K/AKT Inhibition", Anticancer Research 34:1857-1864 (2014).

Clarijis et al., "Presence of a Fluid-Conducting Meshwork in Xenografted Cutaneous and Primary Human Uveal Melanoma", IOVS, Apr. 2002, vol. 43, No. 4.

Clarke et al., "Clinical Pharmacokinetics of Docetaxel", Clin Pharmacokinet (Feb. 1999) 36(2):99-114.

Cole et al., "A Strategy for the Production of Human Monoclonal Antibodies Reactive with Lung Tumor Cell Lines", Cancer Research 44, 2750-2753, Jul. 1984).

Dal Farra et al., "Involvement of the Neurotensin Receptor Subtype NTR3 in the Growth Effect of Neurotensin on Cancer Cell Lines", Int J. Cancer: 92, 503-509 (2001).

Fernandez-Cortes et al., "Vasculogenic Mimicry: Become an Endothelial Cell "But Not So Much"", Frontiers in Oncology, Aug. 2019, vol. 9, Article 803.

Foote et al., "Antibody Framework Residues Affecting the Conformation of the Hypervariable Loops", J. Mol. Biol. (1992) 224, 487-499.

Ge et al., "Overview of advances in vasculogenic mimicry—a potential target for tumor therapy", Cancer Management and Research 2018: 10.

Giorgi et al., "Expression of Neurotensin and its Receptors in Pituitary Adenomas", Journal of Neuroendocrinology 20, 1052-1057 (May 26, 2008).

Han et al., "The Association Between Sortilin and Inflammation in Patients with Coronary Heart Disease", Journal of Inflammation Reseach 2020: 13, 71-79.

Karlin et al., "Methods for assessing the statistical significance of molecular sequence features by using general scoring schemes", Proc. Natl. Acad. USA, vol. 87, pp. 2264-2268, Mar. 1990—Evolution.

Karlin et al., "Applications and statistics for multiple high-scoring segments in molecular sequences", Proc. Natl. Acad. Sci. USA 90 (Mar. 24, 1993).

Kirschmann et al., "Moleuclar Pathways: Vasculogenic Mimicry in Tumor Cells: Diagnostic and Therapeutic Implications", Clin Cancer Res; 18(10) May 15, 2012.

Kobayashi et al., "Rapid Accumulation and Internalization of Radiolabeled Herceptin in an Inflammatory Breast Cancer Xenograft with Vasculogenic Mimicry Predicted by the Contrast-enhanced Dynamic MRI with the Macromolecular Contrast Agent G6-(1B4M-Gd)256", Cancer Research 62, 860-866, Feb. 1, 2002.

Kohler, "Continuous cultures of fused cells secreting antibody of predefined specificity", Nature, vol. 256, Aug. 7, 1975.

Kozbor et al., "The production of monoclonal antibodies from human lymphocytes", Immunology Today, vol. 4, No. 3, 1983.

Lewin et al., "Pro-neurotrophins, sortilin, and noceception", European Journal of Neuroscience, vol. 39, pp. 363-374, 2014.

Liang et al., "Association of Vasculogenic Mimicry Formation and CD133 Expression with Poor Prognosis in Ovarian Cancer", Gynecol Obstet Invest, Apr. 29, 2016.

Liu et al., "CD133+ cells with cancer stem cell characteristics associates with vasculogenic mimicry in triple-negative breast cancer", Oncogene (2013) 32, 544-553.

Maniotis et al., "Control of Melanoma Morphogenesis, Endothelial Survival, and Perfusion by Extracellular Matrix", Laboratory Investigation, vol. 82, No. 8, p. 1031, Aug. 2002.

McCafferty et al., "Phage antibodies: filamentous phage displaying antibody variable domains", Nature, vol. 348. Dec. 6, 1990.

Medzhitov, "Origin and physiological roles of inflammation", Nature, vol. 454, Jul. 24, 2008.

Ophir et al., "Personalized approaches to active immunotherapy in cancer", Biochimical et Biophysica Acta 1865 (2016) 72-82.

Poster of Katana biopharma, "Increasing penetration of anticancer drugs through Sortilin receptor-mediated cancer therapy: A new targeted and personalized approach in the treatment of ovarian cancer" UQAM 2017.

Qiao et al., "Advanced Research on vasculogenic mimicry in cancer", J. Cell. Mol. Med. Vol. 19, No. 2, 2015 pp. 315-326.

(56) References Cited

OTHER PUBLICATIONS

Racordon et al., "Structural and functional identification of vasculogenic mimicry in vitro", Scientific Reports, 7:6985 (Aug. 1, 2017).

Riechmann et al., "Reshaping human antibodies for therapy", Nature, vol. 332 (Mar. 24, 1988).

Sahebkar et al., "Curcumin downregulates human tumor necrosis factor-a levels: A systematic review and metal-analysis of randomized controlled trials", Pharmacological Research, vol. 107, May 2016, 234-242.

Sapiezynski et al., "Precision targeted therapy of ovarian cancer", Journal of Controlled Release (Oct. 14, 2016) 250-268.

Scavelli et al., "Vasculogenic mimicry by bone marrow macrophages in patients with multiple myeloma", Oncogene (2008), 663-674.

Sun et al., "Epithelial-to-endothelial transition and cancer stem cells: two cornerstones of vasculogenic mimicry in malignant tumors", Oncotarget, 2017, vol. 8 (No. 18), pp. 30502-30510.

Talbot et al., "Regulatory Roles of Sortilin and SorLA in Immune-Related Processes", Frontiers in Pharmacology, Jan. 7, 2019.

Urruticoechea et al., "Recent Advances in Cancer Therapy: An Overview", Current Pharmaceutical Design, 2010, 16, 3-10.

Vaegter et al., "Sortilin associates with Trk receptors to enhance anterograde transport and neurotrophin signaling" vol. 14, No. 1, Jan. 2011, Nature Science.

Wilson et al., "The Implications of Sortilin/Vps10p Domain Receptors in Neurological and Human Diseases", CNS & Neurological Disorders—Drug Targets, 2014, 13, 1354-1365.

Wilson et al., "A new role under sortilin's belt in cancer", Communicative & Integrative Biology, Mar. 1, 2016, vol. 9, No. 1.

Xiong et al., "ProBDNF and its receptors are upregulated in glioma and inhibits the grown of glioma cells in vitro", Neuro-Oncology 15(8) 990-1007, Apr. 10, 2013.

Yang et al., "Tumor vasculogenic mimicry predicts poor prognosis in cancer patients: a meta-analysis", Angiogenesis (Feb. 22, 2016) 19:191-200.

Yano et al., "A humanized Antibody Specific for the Platelet Integrin gpIIb/IIIa", J Immunol 1994; 152:2968-2976.

Zhao et al., "Docetaxel Nanotechnology in Anticancer Therapy", ChemMedChem 0000, 00, 1-22 (2012).

Chapter 5—Cancer by Organ Site: International Agency for Recearch on Cancer—World Health Organization, "World Cancer Report 2014", Edited by Bernard W. Stewart and Christopher P. Wild, Lyon, 2014.

Barnett S. Kramer, "Controversies in cancer screening and their resolution: a view from the United States 'battleground'"; International Agency for Recearch on Cancer—World Health Organization, "World Cancer Report 2014", Edited by Bernard W. Stewart and Christopher P. Wild, Lyon, 2014.

Chapter 6—Cancer Control: International Agency for Research on Cancer—World Health Organization, "Work Cancer Report 2014", Edited by Bernard W. Stewart and Christopher P. Wild, Lyon, 2014.

Richard Peto in collaboration with Aland D. Lopez, Hongchao Pan, and Michael J. Thun, "The full hazards of smoking and the benefits of stopping: cancer mortality and overall mortality"; International Agency for Recearch on Cancer—World Health Organization, "World Cancer Report 2014", Edited by Bernard W. Stewart and Christopher P. Wild, Lyon, 2014.

Bonavia et al., "Heterogeneity Maintenance in Glioblastoma: A Social Network", Published Online First on May 31, 2011; DOI: 10.1158/0008-5472.CAN-11-0153.

Corbin et al., "Tumour heterogeneity and cancer cell plasticity", Nature, vol. 501, Sep. 19, 2013.

Diaz et al., "The molecular evolution of acquired resistance to targeted EGFR blockade in colorectal cancers", Nature, Jun. 28, 2012; 486(7404):537-540.

Fisher et al., "Cancer heterogeneity: implications for targeted therapeutics", British Journal of Cancer (Jan. 8, 2013) 108, 479-485.

Fodale et al., "Mechanism of Cell Adaptation / When and How Do Cancer Cells Develop Chemoresistance?", The Cancer Journal, vol. 17, No. 2, Mar./Apr. 2011, pp. 89-95.

Ghaemimanesh et al., "The Effect of Sortilin Silencing on Ovarian Carcinoma Cells", Avicenna Journal of Medical Biotechnology, vol. 6, No. 3, Jul.-Sep. 2014, pp. 169-177.

Gore et al., "Challenges and opportunities for converting renal cell carcinoma into a chronic disease with targeted therapies", British Journal of Cancer (2011) 104, 399-406. (The year of publication is sufficiently earlier than the effective U.S. filing date so that the particular month of publication is not an issue).

Hemmati et al., "Ectopic Expression of Sortilin 1 (NTR-3) in Patients with Ovarian Carcinoma", Avicenna Journal of Medical Biotechnology, vol. 1, No. 2, Jul.-Sep. 2009, pp. 125-131.

Heppner, "Perspectives in Cancer Research", Cancer Research 44, 2259-2265, Jun. 1984.

Hosseini et al., "Cancer therapy with phytochemicals: evidence from clinical studies", Avicenna Journal of Phytomedicine, vol. 5, No. 2, Mar.-Apr. 2015.

Kolby et al., "Sortilin, Encoded by the Cardiovascular Risk Gene SORT1, and Its Suggested Functions in Cardiovascular Disease", Curr Atheroscler Rep (2015) 17: 18. (The year of publication is sufficiently earlier than the effective U.S. filing date so that the particular month of publication is not an issue).

Kreso et al., "Variable Clonal Repopulation Dynamics Influence Chemotherapy Response in Colorectal Cancer", Science, vol. 339, Feb. 1, 2013.

Marusyk et al., "Tumor heterogeneity: Causes and consequences", Biochimica et Biophysical Acta 1805 (2010) 105-117. (The year of publication is sufficiently earlier than the effective U.S. filing date so that the particular month of ublication is not an issue).

Marusyk et al., "Cancer Cell Phenotypes, in Fifty Shades of Grey", Science, vol. 339, Feb. 1, 2013.

Mortensen et al., "Targeting sortilin in immune cells reduces proinflammatory cytokines and atherosclerosis", J Clin Invest. 2014; 124(12):5317-5322. (The year of publication is sufficiently earlier than the effective U.S. filing date so that the particular month of publication is not an issue).

Navarro et al., "Shedding of the luminal domain of the neurotensin receptor-3/sortilin in the HT29 cell line", Biochemical and Biophysical Research Communications 298 (Oct. 10, 2002) 760-764.

Nowell, "The Clonal Evolution of Tumor Cell Populations", Science, New Series, vol. 194, No. 4260 (Oct. 1, 1976), pp. 23-28.

Lavi et al., "The Role of Cell Density and Intratumoral Heterogeneity in Multidrug Resistance", Cancer Res; 73(24) Dec. 15, 2013.

Prabakaran et al., "Mannose 6-Phosphate Receptor and Sortilin Mediated Endocytosis of α-Galactosidase A in Kidney Endothelial Cells", PloS ONE, Jun. 2012, vol. 7, Issue 6.

Roselli et al., "Sortilin is associated with breast cancer aggressiveness and contributes to tumor cell adhesion and invasion", Oncotarget, vol. 6, No. 12, Mar. 18, 2015.

Sanz-Moreno et al., "Rac Activation and Inactivation Control Plasticity of Tumor Cell Movement", Cell 135, 510-523, Oct. 31, 2008.

Silva et al., "Modulation of P-glycoprotein efflux pump: induction and activation as a therapeutic strategy", Pharmacoloty & Therapeutics 149 (2015) 1-123. (The year of publication is sufficiently earlier than the effective U.S. filing date so that the particular month of publication is not an issue).

Zhou, "Structure, function and regulation of P-glycoprotein and its clinical relevance in drug disposition", Xenobiotica, Jul.-Aug. 2008; 38(7-8): 802-832.

Abstract of Gillet et al., "Mechanisms of multidrug resistance in cancer", Methods Mol Biol. 2010; 596:47-76. (The year of publication is sufficiently earlier than the effective U.S. filing date so that the particular month of publication is not an issue).

Olga Serup Andersen et al., "Identification of a Linear Epitope in Sortilin that Partakes in Pro-neurotrophin Binding", J Biol Chem. Apr. 16, 2010; 285(16): 12210-12222.

Perrone et al., "Biological and therapeutic activities, and anticancer properties of curcumin (Review)", Experimental and Therapeutic Medicine 10: 1615-1623, Jul. 14, 2015.

Yabe-Wada et al., "TLR signals posttranscriptionally regulate the cytokine trafficking mediator sortilin", Scientific Reports 6:26566 DOI: 10.1038/SREP26566, Published on May 25, 2016.

(56) References Cited

OTHER PUBLICATIONS

Introduction: International Agency for Recearch on Cancer—World Health Organization, "World Cancer Report 2014", Edited by Bernard W. Stewart and Christopher P. Wild, Lyon, 2014.

Chapter 1—Cancer Worldwide: International Agency for Recearch on Cancer—World Health Organization, "World Cancer Report 2014", Edited by Bernard W. Stewart and Christopher P. Wild, Lyon, 2014.

Chapter 2—Cancer Etiology: International Agency for Recearch on Cancer—World Health Organization, "World Cancer Report 2014", Edited by Bernard W. Stewart and Christopher P. Wild, Lyon, 2014.

Cesar G. Victora, "Early-life exposures, birth cohorts, and noncommunicable diseases (with special reference to cancer)"; International Agency for Recearch on Cancer—World Health Organization, "World Cancer Report 2014", Edited by Bernard W. Stewart and Christopher P. Wild, Lyon, 2014.

Chapter 3—Cancer Biology: International Agency for Recearch on Cancer—World Health Organization, "World Cancer Report 2014", Edited by Bernard W. Stewart and Christopher P. Wild, Lyon, 2014.

Harald zur Hausen in collaboration with Ethel-Michele de Villiers, "Prenatal infections with subsequent immune tolerance could explain the epidemiology of common childhood cancer"; International Agency for Recearch on Cancer—World Health Organization, "World Cancer Report 2014", Edited by Bernard W. Stewart and Christopher P. Wild, Lyon, 2014.

Chapter 4—Cancer Prevention: International Agency for Recearch on Cancer—World Health Organization, "World Cancer Report 2014", Edited by Bernard W. Stewart and Christopher P. Wild, Lyon, 2014.

Mel Greaves, "An evolutionary foundation for cancer control"; International Agency for Recearch on Cancer—World Health Organization, "World Cancer Report 2014", Edited by Bernard W. Stewart and Christopher P. Wild, Lyon, 2014.

\* cited by examiner

PRIOR ART

Expression of Sortilin in homogenates of human cancer cell lines

PRIOR ART

AUC1-24
KBA105 = 47.0
Docetaxel = 1.35
Ratio: 34.8

A.

B.

A. Docetaxel

B. KBA105

A.

B.

C.

A.

B.

A.
Breast cancer MDA-MB231/luciferase
Residual Tumor Burden

B.

C.

A.

C.

SEQUENCE LISTING

```
<160> NUMBER OF SEQ ID NOS: 22

<210> SEQ ID NO 1
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (14)..(14)
<223> OTHER INFORMATION: Xaa can be any amino acid
<220> FEATURE:
```

```
<221> NAME/KEY: MISC_FEATURE
<222> LOCATION: (16)..(16)
<223> OTHER INFORMATION: Xaa can be any amino acid

<400> SEQUENCE: 1

Xaa Xaa Xaa Xaa Xaa Gly Val Xaa Ala Lys Ala Gly Val Xaa Asn Xaa
1               5                   10                  15

Phe Lys Ser Glu Ser Tyr
            20

<210> SEQ ID NO 2
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: Xaa can be any amino acid and can be either
      present or absent
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (15)..(15)
<223> OTHER INFORMATION: Xaa can be any amino acid
<220> FEATURE:
<221> NAME/KEY: MISC_FEATURE
<222> LOCATION: (17)..(17)
<223> OTHER INFORMATION: Xaa can be any amino acid

<400> SEQUENCE: 2

Xaa Xaa Xaa Xaa Xaa Xaa Gly Val Xaa Ala Lys Ala Gly Val Xaa Asn
1               5                   10                  15

Xaa Phe Lys Ser Glu Ser Tyr
            20

<210> SEQ ID NO 3
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be any amino acid
<220> FEATURE:
<221> NAME/KEY: MISC_FEATURE
<222> LOCATION: (22)..(23)
<223> OTHER INFORMATION: Xaa can be either Gln, Pro, Tyr, Ile or Leu

<400> SEQUENCE: 3

Tyr Lys Xaa Leu Arg Arg Xaa Ala Pro Arg Trp Asp Xaa Pro Leu Arg
1               5                   10                  15

Asp Pro Ala Leu Arg Xaa Xaa Leu
            20

<210> SEQ ID NO 4
```

```
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (7)..(12)
<223> OTHER INFORMATION: Xaa can be any amino acid and can be either
      present or absent
<220> FEATURE:
<221> NAME/KEY: MISC_FEATURE
<222> LOCATION: (21)..(22)
<223> OTHER INFORMATION: Xaa can be either Gln, Pro, Tyr, Ile or Leu

<400> SEQUENCE: 4

Tyr Lys Xaa Leu Arg Arg Xaa Xaa Xaa Xaa Xaa Pro Leu Arg Asp
1               5                   10                  15

Pro Ala Leu Arg Xaa Xaa Leu
            20

<210> SEQ ID NO 5
<211> LENGTH: 22
<212> TYPE: PRT
<213> ORGANISM: Artificial Sequence
<220> FEATURE:
<223> OTHER INFORMATION: Synthetic Construct

<400> SEQUENCE: 5

Ile Lys Leu Ser Gly Gly Val Gln Ala Lys Ala Gly Val Ile Asn Met
1               5                   10                  15

Asp Lys Ser Glu Ser Met
            20

<210> SEQ ID NO 6
<211> LENGTH: 22
<212> TYPE: PRT
<213> ORGANISM: Artificial Sequence
<220> FEATURE:
<223> OTHER INFORMATION: Synthetic Construct

<400> SEQUENCE: 6

Ile Lys Leu Ser Gly Gly Val Gln Ala Lys Ala Gly Val Ile Asn Met
1               5                   10                  15

Phe Lys Ser Glu Ser Tyr
            20

<210> SEQ ID NO 7
<211> LENGTH: 23
<212> TYPE: PRT
<213> ORGANISM: Artificial Sequence
<220> FEATURE:
<223> OTHER INFORMATION: Synthetic Construct

<400> SEQUENCE: 7

Ile Lys Leu Ser Gly Gly Val Gln Ala Lys Ala Gly Val Ile Asn Met
1               5                   10                  15

Phe Lys Ser Glu Ser Tyr Lys
            20

<210> SEQ ID NO 8
<211> LENGTH: 17
<212> TYPE: PRT
```

```
<213> ORGANISM: Artificial Sequence
<220> FEATURE:
<223> OTHER INFORMATION: Synthetic Construct

<400> SEQUENCE: 8

Gly Val Gln Ala Lys Ala Gly Val Ile Asn Met Phe Lys Ser Glu Ser
1               5                   10                  15

Tyr

<210> SEQ ID NO 9
<211> LENGTH: 17
<212> TYPE: PRT
<213> ORGANISM: Artificial Sequence
<220> FEATURE:
<223> OTHER INFORMATION: Synthetic Construct

<400> SEQUENCE: 9

Gly Val Arg Ala Lys Ala Gly Val Arg Asn Met Phe Lys Ser Glu Ser
1               5                   10                  15

Tyr

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa is Nle

<400> SEQUENCE: 10

Gly Val Arg Ala Lys Ala Gly Val Arg Asn Xaa Phe Lys Ser Glu Ser
1               5                   10                  15

Tyr

<210> SEQ ID NO 11
<211> LENGTH: 24
<212> TYPE: PRT
<213> ORGANISM: Artificial Sequence
<220> FEATURE:
<223> OTHER INFORMATION: Synthetic Construct

<400> SEQUENCE: 11

Tyr Lys Ser Leu Arg Arg Lys Ala Pro Arg Trp Asp Ala Pro Leu Arg
1               5                   10                  15

Asp Pro Ala Leu Arg Gln Leu Leu
            20

<210> SEQ ID NO 12
<211> LENGTH: 24
<212> TYPE: PRT
<213> ORGANISM: Artificial Sequence
<220> FEATURE:
<223> OTHER INFORMATION: Synthetic Construct

<400> SEQUENCE: 12

Tyr Lys Ser Leu Arg Arg Lys Ala Pro Arg Trp Asp Ala Tyr Leu Arg
1               5                   10                  15

Asp Pro Ala Leu Arg Gln Leu Leu
            20

<210> SEQ ID NO 13
```

```
<211> LENGTH: 24
<212> TYPE: PRT
<213> ORGANISM: Artificial Sequence
<220> FEATURE:
<223> OTHER INFORMATION: Synthetic Construct

<400> SEQUENCE: 13

Tyr Lys Ser Leu Arg Arg Lys Ala Pro Arg Trp Asp Ala Tyr Leu Arg
1               5                   10                  15

Asp Pro Ala Leu Arg Pro Leu Leu
            20

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION

<400> SEQUENCE: 14

Gly Val Arg Ala Lys Ala Gly Val Arg Asn Met Phe Lys Ser Glu Ser
1               5                   10                  15

Tyr

<210> SEQ ID NO 15
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (11)..(11)
<223> OTHER INFORMATION: Xaa is Nle

<400> SEQUENCE: 15

Gly Val Arg Ala Lys Ala Gly Val Arg Asn Xaa Phe Lys Ser Glu Ser
1               5                   10                  15

Tyr

<210> SEQ ID NO 16
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION

<400> SEQUENCE: 16

Tyr Lys Ser Leu Arg Arg Lys Ala Pro Arg Trp Asp Ala Pro Leu Arg
1               5                   10                  15

Asp Pro Ala Leu Arg Gln Leu Leu
            20

<210> SEQ ID NO 17
<211> LENGTH: 24
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION

<400> SEQUENCE: 17

Tyr Lys Ser Leu Arg Arg Lys Ala Pro Arg Trp Asp Ala Tyr Leu Arg
1               5                   10                  15

Asp Pro Ala Leu Arg Gln Leu Leu
            20

<210> SEQ ID NO 18
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION

<400> SEQUENCE: 18

Tyr Lys Ser Leu Arg Arg Lys Ala Pro Arg Trp Asp Ala Tyr Leu Arg
1               5                   10                  15

Asp Pro Ala Leu Arg Pro Leu Leu
            20

<210> SEQ ID NO 19
<211> LENGTH: 23
<212> TYPE: PRT
<213> ORGANISM: Homo sapiens

<400> SEQUENCE: 19

Lys Cys Leu Arg Arg Glu Ala Pro Arg Trp Asp Ala Pro Leu Arg Asp
1               5                   10                  15

Pro Ala Leu Arg Gln Leu Leu
            20

<210> SEQ ID NO 20
<211> LENGTH: 23
<212> TYPE: PRT
<213> ORGANISM: Rattus norvegicus

<400> SEQUENCE: 20

Lys Cys Leu Arg Lys Lys Thr Pro Arg Trp Asp Ile Leu Leu Arg Asp
1               5                   10                  15

Pro Ala Pro Arg Pro Leu Leu
            20

<210> SEQ ID NO 21
<211> LENGTH: 23
<212> TYPE: PRT
<213> ORGANISM: Mus musculus

<400> SEQUENCE: 21

Lys Cys Leu Arg Lys Lys Ile Pro Arg Trp Asp Met Phe Leu Arg Asp
1               5                   10                  15

Pro Val Pro Arg Pro Leu Leu
            20
```

```
<210> SEQ ID NO 22
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa can be any amino acid

<400> SEQUENCE: 22

Xaa Leu Tyr Glu Asn Lys Pro Arg Arg Pro Tyr Ile Leu
1               5                   10
```

PEPTIDE COMPOUNDS AND PEPTIDE CONJUGATES FOR THE TREATMENT OF CANCER THROUGH RECEPTOR-MEDIATED CHEMOTHERAPY

RELATED APPLICATIONS

This present application is a continuation of Ser. No. 15/778,626 filed on May 24, 2018 that is a 35 USC 371 national stage entry of PCT/CA2016/051379 filed on Nov. 24, 2016 and which claims the benefit of priority of U.S. Patent Application Ser. No. 62/259,178 filed on Nov. 24, 2015. These documents are hereby incorporated herein by reference in their entirety.

FIELD OF THE DISCLOSURE

The present disclosure relates to peptide compounds and conjugate compounds, processes, methods and uses thereof for treating cancer.

BACKGROUND OF THE DISCLOSURE

Cancer

According to a recent World Health Organization report (February, 2014), 8.2 million patients died from cancer in 2012. Cancer is therefore a growing health problem in both developing and developed countries. It has also been estimated that the number of annual cancer cases will increase from 14 million in 2012 to 22 million within the next two decades (WHO, 2014). Currently, the classical treatments for cancer are chemotherapy, radiotherapy and surgery.

Resistance to chemotherapy remains a major cause of failure of cancer treatment. This resistance phenotype results from numerous mechanisms. The "traditional" understanding of multidrug resistance (MDR) and its driving mechanisms over-simplifies the complexity of a perturbed cellular cancer network and focuses on several pathways/gene families (Orit, 2013). From that perspective, drug resistance is rather associated with the induction of drug efflux, activation of DNA repair, variations in target proteins, decreased drug uptake, altered metabolisms, sequestration, and changes in apoptotic pathways (Fodalet, 2011; Gillet, 2010). Recently, intratumoural heterogeneity has also been inferred to be a major facilitator of drug resistance in reference to differences observed between cancer cells originating within the same tumour. Indeed, many primary human tumours have been found to contain genetically distinct cellular subpopulations reported to be mainly the result of stochastic processes and microenvironment signals. In addition to the genetic differences or heterogeneity within a tumour, therapeutic resistance can also be caused by several other non-genetic processes, such as epigenetic changes associated with chromatin modification or DNA methylation (Sanz-Moreno, 2008). One study of these processes was performed in a system with a single genetic clone, and concluded that there was functional variability among tumour cells (Kreso, 2013; Marusyk, 2013). Clearly, the integration of both genetic and nongenetic assumptions as well as heterogeneity should be included in the design of new experimental and computational models to have a better description and ultimately a solution to the problem of MDR.

Multidrug Resistance

Clinical progress in the treatment of primary tumours has been slow. One of the problems associated with the treatment of these tumours is their relatively weak response to anticancer drugs (Zhou, 2008; Silvia, 2015). The effectiveness of chemotherapy and immunotherapy has been impaired by inherent or acquired MDR phenotype by cancer cells. One of the major mechanisms involved in MDR phenotype involves the expression of P-glycoprotein (P-gp), a membrane transporter that pumps out various anticancer drugs from MDR cells. P-gp is also expressed in a large number of normal secretory tissues such as kidney, liver and intestine. In humans, it has been reported that P-gp is encoded by two MDR genes (MDR1 and MDR3). Human MDR1 confers the resistance phenotype, whereas human MDR3 does not. Thus, P-gp may be considered as a "guardian" that limits the entry of drugs by expulsing them out of cancer cells preventing them from reaching cytotoxic concentrations.

Tumour Heterogeneity

Intra- and Inter-Tumoural Heterogeneity

Cancer is a devious foe, revealing new complexities just as scientists find new ways to tackle them. A recent hope has been put in the new generation of "targeted therapeutics" that home in on specific molecular defects in cancer cells, promising more effective and less toxic therapy than imprecise chemotherapeutic agents (Fisher, 2013). However, researchers are now realizing that they may have previously under estimated one of cancer's oldest and best-known complexity: tumour heterogeneity. This, in part, explains the successes and disappointments with targeted therapeutics and should motivate a broader re-examination of current research strategies.

Tumour heterogeneity refers to the existence of subpopulations of cells, with distinct genotypes and phenotypes that may harbour divergent biological behaviours, within a primary tumour and its metastases, or between tumours of the same histopathological subtype (intra- and inter-tumour, respectively) (Corbin, 2013). With the advent of deep sequencing techniques, the extent and prevalence of intra- and inter-tumour heterogeneity is increasingly acknowledged. There are features of intra-tumour heterogeneity that form part of routine pathologic assessment, but its determination does not yet form part of the clinical decision-making process. Nuclear pleomorphism is another example of intra-tumour heterogeneity, which is accounted for in breast cancer grading, for instance. It is also readily apparent to clinicians treating cancer that there is marked variation in tumour behaviour between patients with the same tumour type, and between different tumour sites in the same patient; the latter is usually manifested as differential or mixed responses to therapy.

Clonal Evolution as a Model of Tumour Progression and Heterogeneity

A clonal evolutionary model of cancer development was first proposed by Nowell (1976) and elaborates upon Darwinian models of natural selection—that is, genetically unstable cells accumulate genetic alterations, and that selective pressures favour the growth and survival of variant subpopulations with a biological fitness advantage. Spatial and temporal heterogeneity may permit the tumour as a whole to adapt to a fluctuating tumour microenvironment. In summary, it is argued that heterogeneous tumours should be viewed as complex ecosystems or societies, in which even a minor tumour subpopulation may influence growth of the entire tumour and thereby actively maintain tumour heterogeneity (Heppner, 1984; Marusyk, 2010; Bonavia, 2011). In this model, subclones occupy various niches within the tumour microenvironment and the survival advantage of the tumour 'society' exceeds those of the individual subpopulation; relationships between subclones may be competitive, commensal, or mutualistic for this purpose.

Clinical Implications of Tumour Heterogeneity

The issue of cancer heterogeneity, including the relationships between subpopulations within and between tumour lesions, may have profound implications for drug therapy in cancer. Targeted therapy, which attempts to exploit a tumour's dependence on a critical proliferation or survival pathway, has significantly improved patient outcomes in a range of solid tumour types, but in the majority of advanced disease cases, it is also apparent that targeted therapeutics do not help all molecularly selected patients and even when clinical benefit is observed, it is often of limited duration (Gore, 2011; Diaz, 2012). Tumour heterogeneity may partly explain these clinical phenomena, and this prompts for the development of a more efficient platform that circumvents the MDR phenotype.

SUMMARY OF THE DISCLOSURE

Accordingly, a first aspect is a peptide compound having at least 80% sequence identity to a compound chosen from compounds of formula (I), formula (II), formula (III), formula (IV), formula (V), formula (VI), formula (VII), formula (VIII), formula (IX), formula (X), formula (XI) and formula (XII):

| | |
|---|---|
| $X_1X_2X_3X_4X_5GVX_6AKAGVX_7NX_8FKSESY$ (I) | (SEQ ID NO: 1) |
| $(X_9)_nGVX_{10}AKAGVX_{11}NX_{12}FKSESY$ (II) | (SEQ ID NO: 2) |
| $YKX_{13}LRRX_{14}APRWDX_{15}PLRDPALRX_{16}X_{17}L$ (III) | (SEQ ID NO: 3) |
| $YKX_{18}LRR(X_{19})_nPLRDPALRX_{20}X_{21}L$ (IV) | (SEQ ID NO: 4) |
| IKLSGGVQAKAGVINMDKSESM (V) | (SEQ ID NO: 5) |
| IKLSGGVQAKAGVINMFKSESY (VI) | (SEQ ID NO: 6) |
| IKLSGGVQAKAGVINMFKSESYK (VII) | (SEQ ID NO: 7) |
| GVQAKAGVINMFKSESY (VIII) | (SEQ ID NO: 8) |
| GVRAKAGVRNMFKSESY (IX) | (SEQ ID NO: 9) |
| GVRAKAGVRN(Nle)FKSESY (X) | (SEQ ID NO: 10) |
| YKSLRRKAPRWDAPLRDPALRQLL (XI) | (SEQ ID NO: 11) |
| YKSLRRKAPRWDAYLRDPALRQLL (XII) | (SEQ ID NO: 12) |
| YKSLRRKAPRWDAYLRDPALRPLL (XIII) | (SEQ ID NO: 13) | wherein $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{18}$ and $X_{19}$ are independently chosen from any amino acid;

$X_{16}$, $X_{17}$, $X_{20}$ and $X_{21}$ are independently chosen from Q, P, Y, I and L;

n is 0, 1, 2, 3, 4 or 5, when $X_9$ is present more than once, each of said $X_9$ is independently chosen from any amino acid;

when $X_{19}$ is present more than once, each of said $X_9$ is independently chosen from any amino acid;

and wherein at least one protecting group and/or at least one labelling agent is optionally connected to said peptide at an N- and/or C-terminal end.

In a further aspect, there is provided peptide compounds that are in fact any peptide compounds described in the present disclosure, to which about 5 or 6 amino acids have been omitted or removed.

In a further aspect, there is provided peptide compounds that are in fact compounds comprising at least 5 or at least 6 consecutive amino acids as defined in the previously presented peptide compounds.

In a further aspect, there is provided a peptide compound comprising a compound chosen from compounds of formula (I), formula (II), formula (III), formula (IV), formula (V), formula (VI), formula (VII), formula (VIII), formula (IX), formula (X), formula (XI) and formula (XII):

| | |
|---|---|
| $X_1X_2X_3X_4X_5GVX_6AKAGVX_7NX_8FKSESY$ (I) | (SEQ ID NO: 1) |
| $(X_9)_nGVX_{10}AKAGVX_{11}NX_{12}FKSESY$ (II) | (SEQ ID NO: 2) |
| $YKX_{13}LRRX_{14}APRWDX_{15}PLRDPALRX_{16}X_{17}L$ (III) | (SEQ ID NO: 3) |
| $YKX_{18}LRR(X_{19})_nPLRDPALRX_{20}X_{21}L$ (IV) | (SEQ ID NO: 4) |
| IKLSGGVQAKAGVINMDKSESM (V) | (SEQ ID NO: 5) |
| IKLSGGVQAKAGVINMFKSESY (VI) | (SEQ ID NO: 6) |
| IKLSGGVQAKAGVINMFKSESYK (VII) | (SEQ ID NO: 7) |
| GVQAKAGVINMFKSESY (VIII) | (SEQ ID NO: 8) |
| GVRAKAGVRNMFKSESY (IX) | (SEQ ID NO: 9) |
| GVRAKAGVRN(Nle)FKSESY (X) | (SEQ ID NO: 10) |
| YKSLRRKAPRWDAPLRDPALRQLL (XI) | (SEQ ID NO: 11) |
| YKSLRRKAPRWDAYLRDPALRQLL (XII) | (SEQ ID NO: 12) |
| YKSLRRKAPRWDAYLRDPALRPLL (XIII) | (SEQ ID NO: 13) | wherein $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{18}$ and $X_{19}$ are independently chosen from any amino acid;

$X_{16}$, $X_{17}$, $X_{20}$ and $X_{21}$ are independently chosen from Q, P, Y, I and L;

n is 0, 1, 2, 3, 4 or 5, when $X_9$ is present more than once, each of said $X_9$ is independently chosen from any amino acid;

when $X_{19}$ is present more than once, each of said $X_9$ is independently chosen from any amino acid;

and wherein at least one protecting group and/or at least one labelling agent is optionally connected to said peptide at an N- and/or C-terminal end.

In a further aspect disclosed herein is a conjugate compound having the formula of A-(B)$_n$, wherein n is 1, 2, 3 or 4;

A is a peptide compound as defined in the present disclosure, wherein said peptide is optionally protected by a protecting group; and B is at least one therapeutic agent, wherein B is connected to A.

In a further aspect disclosed herein is a conjugate compound having the formula of A-(B)$_n$, wherein n is 1, 2, 3 or 4;

A is a peptide compound as defined in the present disclosure, wherein said peptide is optionally protected by a protecting group; and B is at least one therapeutic agent, wherein B is connected to A at a free amine of said peptide compound, at an N-terminal position of said peptide compound, at a free —SH of said peptide compound, or at a free carboxyl of said peptide compound.

A further aspect disclosed herein is a conjugate compound having the formula of A-(B)$_n$, wherein n is 1, 2, 3 or 4;

A is a peptide compound as defined in the present disclosure, wherein said peptide is optionally protected by a protecting group; and B is at least one therapeutic agent, wherein B is connected to A at a free amine of a lysine residue of said peptide compound, optionally via a linker, or at an N-terminal position of said peptide compound, optionally via a linker.

In a further aspect, there is provided a process for preparing the conjugate compound herein disclosed, the process comprising:

reacting a linker together with said therapeutic agent so as to obtain an intermediate;

optionally purifying said intermediate;

reacting said intermediate together with said peptide compound so as to obtain said conjugate compound in which said therapeutic agent is connected to said peptide compound via said linker; and optionally purifying said conjugate compound;

wherein the therapeutic agent is connected to the peptide compound at a free amine of a lysine residue or at an N-terminal; and wherein the peptide compound comprises 1, 2, 3 or 4 therapeutic agent molecules connected thereto.

In another aspect, there is provided a method of treating a cancer comprising administrating a therapeutically effective amount of at least one compound herein disclosed to a subject in need thereof.

In another aspect, there is provided a method of treating a cancer involving sortilin expression comprising contacting at least one cancer cell expressing sortilin with at least one compound as defined herein.

In another aspect, there is provided a method of treating a disease involving sortilin expression comprising administering to a subject in need thereof a therapeutically effective amount of at least one compound as defined herein.

In another aspect, there is provided a use of a compound disclosed herein for treating a cancer.

Another aspect is a library comprising at least two of compounds herein disclosed.

Another aspect is a liposome, graphene or nanoparticle comprising at least one compound as defined in the present disclosure.

Another aspect is a liposome, graphene or nanoparticle coated with at least one compound as defined in the present disclosure.

Another aspect is a liposome, graphene or nanoparticle that is loaded with at least one of therapeutic agent or siRNA and the liposome is coated with at least one compound as defined in the present disclosure.

Another aspect relates to a drug delivery system comprising such a liposome, graphene or nanoparticle as defined in the present disclosure.

Another aspect is the use of such liposome, graphene or nanoparticle as defined in the present disclosure, in a drug delivery system.

A further aspect relates to a multimer comprising two or more compounds herein disclosed.

BRIEF DESCRIPTION OF THE FIGURES

Further features and advantages of the disclosure will become more readily apparent from the following description of specific embodiments as illustrated by way of examples in the appended figures wherein.

DETAILED DESCRIPTION OF THE DISCLOSURE

Figure 1:
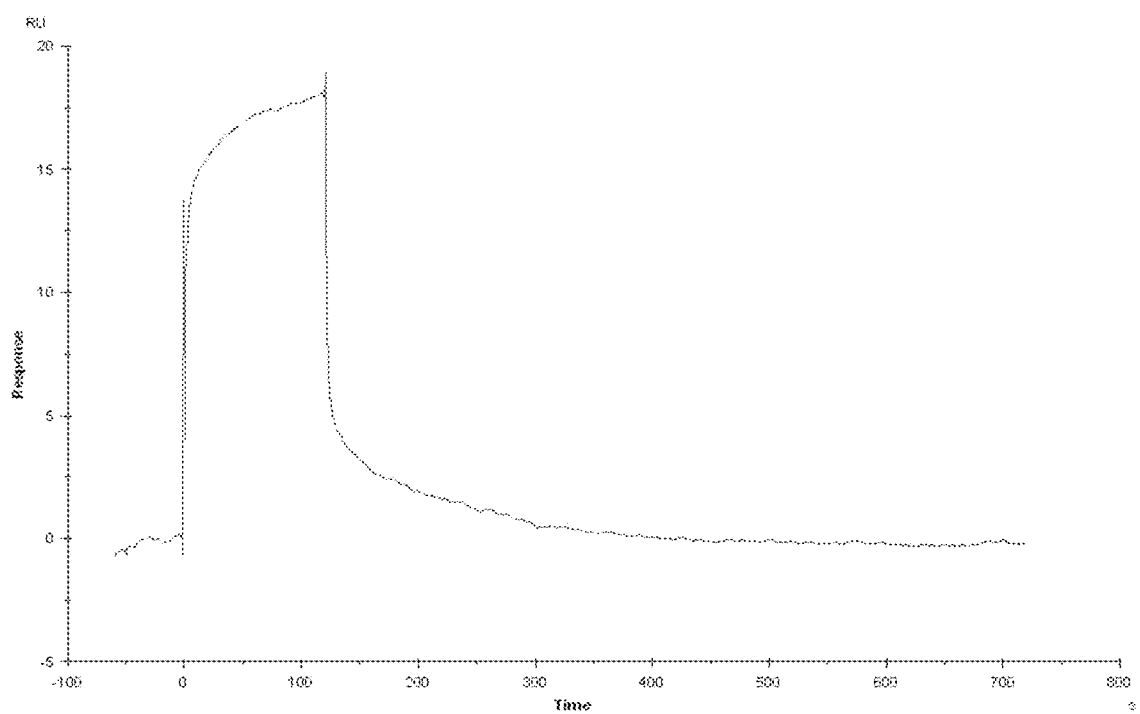
FIG. 1 shows the interaction between Katana peptide and sortilin using surface plasmon resonance. Biotinylated Katana peptide was immobilized on a streptavidin sensor chip. A. Soluble sortilin was then injected over the immobilized peptide. The surface plasmon resonance signal was then monitored over time.
Figure 2:
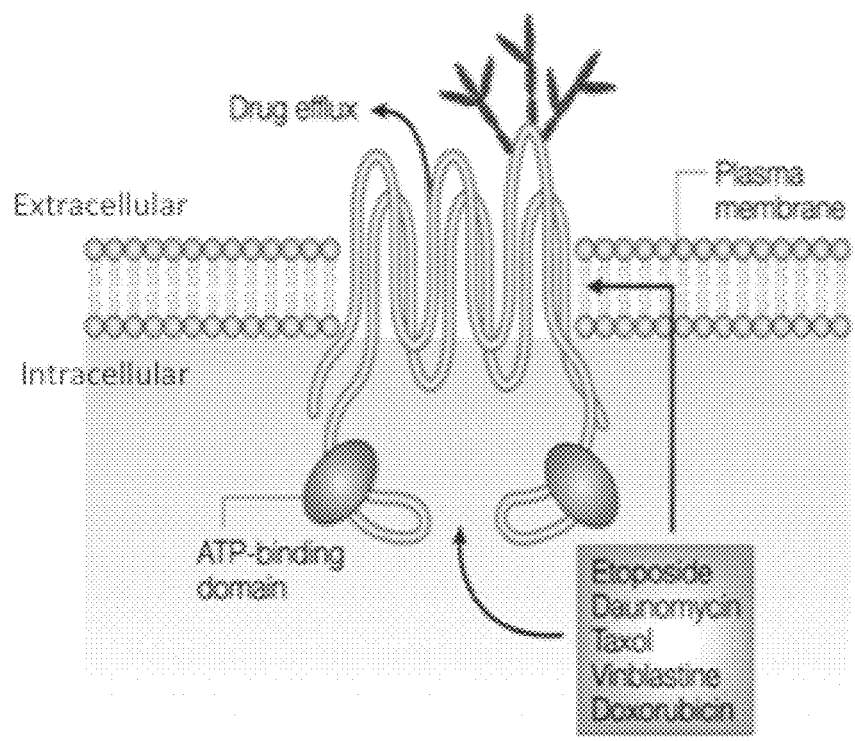
FIG. 2 is a prior art representation of the efflux pump, P-glycoprotein (P-gp or MDR1) at the cell surface. The efflux pump, P-gp or MDR1, associated with multidrug resistance is highly expressed at the cell surface of many cancer cells and various tissues.

The term "peptide compounds" or "Katana peptides", "Katana Biopharma Peptide" or "KBP" as used herein refers, for example, to peptides derived from bacterial proteins or from ligands of receptors that target receptors expressed on cancer cells including multidrug resistant cancer cells. For example, the peptide compounds can be derived from bacterial proteins involved in cell penetration or from sortilin ligands, for example progranulin and neurotensin. In certain embodiments, peptide compounds are connected (for example via a covalent bond, an atom or a linker) to at least one therapeutic agent (such as an anticancer agent or a phytochemical), thereby forming a conjugate compound that can be used, for example, for treating a cancer. In certain other embodiments, peptide compounds can be used at the surface of liposomes. For example, the peptide compounds can be used for coating liposomes or nanoparticles that can be loaded with at least one therapeutic agent (such as an anticancer agent or phytochemical, or genes or siRNA).

The term "Katana Biopharma Peptide Family 1 peptide compounds" or "KBP Family 1 peptide compounds" refers to peptide compounds derived from bacterial cell penetrant proteins. For example, KBP Family 1 peptide compounds can be derived from a protein having an amino acid sequence of IKLSGGVQAKAGVINMDKSESM (SEQ ID NO: 5). Non limiting examples of KBP Family 1 peptide compounds are shown below:

```
Amino acid sequences
KBP-101
IKLSGGVQAKAGVINMDKSESM -
Formula (V) (represented by SEQ ID NO: 5)

KBP-102
Succinyl-IKLSGGVQAKAGVINMFKSESY -
Formula (XXXVI) (comprises SEQ ID NO: 6 wherein a
succinyl group is attached at the N-terminal end)

KBP-103
IKLSGGVQAKAGVINMFKSESYK(Biotin) -
Formula (XXXVII) (comprises SEQ ID NO: 7 wherein a
biotin molecule is connected thereto at the
C-terminal end)

KBP-104
GVQAKAGVINMFKSESY -
Formula (VIII) (represented by SEQ ID NO: 8)

KBP-105
Acetyl-GVRAKAGVRNMFKSESY -
Formula (XXXVIII) (represented by SEQ ID NO: 14)

KBP-106
Acetyl-GVRAKAGVRN(Nle)FKSESY -
Formula (XXXIX) (represented by SEQ ID NO: 15)
```

As used herein, the peptide compound KBP-101 is represented by the amino acid sequence of IKLSGGVQAK-AGVINMDKSESM (SEQ ID NO: 5).

As used herein, the peptide compound KBP-102 is represented by the amino acid sequence of Succinyl-IKLSGGVQAKAGVINMFKSESY that comprises the peptide sequence of SEQ ID NO: 6 wherein a succinyl group is attached thereto at the N-terminal end.

As used herein, the peptide compound KBP-103 is represented by the amino acid sequence of IKLSGGVQAK-AGVINMFKSESYK(Biotin) that comprises the peptide sequence of SEQ ID NO: 7 wherein a biotin molecule is connected thereto at the C-terminal end.

As used herein, the peptide compound KBP-104 is represented by the amino acid sequence of GVQAK-AGVINMFKSESY (SEQ ID NO: 8).

As used herein, the peptide compound KBP-105 is represented by the amino acid sequence of Acetyl-GVRAK-AGVRNMFKSESY (SEQ ID NO: 14).

As used herein, the peptide compound KBP-106 is represented by the amino acid sequence of Acetyl-GVRAK-AGVRN(Nle)FKSESY (SEQ ID NO: 15).

The term "Katana Biopharma Peptide Family 2 peptide compounds" or "KBP Family 2 peptide compounds" refers to peptides derived from sortilin ligands, progranulin and neurotensin. For example, peptides can be derived from human, rat or mouse progranulin. For example, KBP Family 2 peptide compounds can be derived from human progranulin, for example having the amino acid sequence KCLR-REAPRWDAPLRDPALRQLL (SEQ ID NO: 19), from rat progranulin, for example having the amino acid sequence KCLRKKTPRWDILLRDPAPRPLL (SEQ ID NO: 20), from mouse progranulin, for example having the amino acid sequence KCLRKKIPRWDMFLRDPVPRPLL (SEQ ID NO: 21), or from neurotensin, for example having an amino acid sequence XLYENKPRRPYIL (SEQ ID NO: 22). Non limiting examples of KBP Family 2 peptide compounds are shown below:

```
Amino acid sequences
KBP-201
Acetyl-YKSLRRKAPRVVDAPLRDPALRQLL -
Formula (XXXX) (represented by SEQ ID NO: 16)

KBP-202
Acetyl-YKSLRRKAPRVVDAYLRDPALRQLL -
Formula (XXXXI) (represented by SEQ ID NO: 17)

KBP-203
Acetyl-YKSLRRKAPRVVDAYLRDPALRPLL -
Formula (XXXII) (represented by SEQ ID NO: 18)
```

As used herein, the peptide compound KBP-201 is represented by the amino acid sequence of Acetyl-YKSLRRKAPRWDAPLRDPALRQLL (SEQ ID NO: 16).

As used herein, the peptide compound KBP-202 is represented by the amino acid sequence of Acetyl-YKSLRRKAPRWDAYLRDPALRQLL (SEQ ID NO: 17).

As used herein, the peptide compound KBP-203 is represented by the amino acid sequence of Acetyl-YKSLRRKAPRWDAYLRDPALRPLL (SEQ ID NO: 18).

The term "sortilin" as used herein refers to a neuronal type-1 membrane glycoprotein, encoded by the SORT1 gene, belonging to the Vacuolar Protein Sorting 10 protein (Vps10) family of receptors. Sortilin (also known as the neurotensin receptor 3) is expressed abundantly in the central and peripheral nervous systems and is also expressed in other types of tissues. For example, the expression of sortilin is upregulated in a number of cancers including for example ovarian, breast, colon and prostate cancer. Sortilin can exist in two forms, a full-length form (110 kDa) and a truncated form (95 kDa), corresponding to its large luminal domain (or ectodomain), which has been previously detected in the supernatant medium from sortilin-overexpressing cells (Navarro et al., 2002) The peptide compounds and conjugate compounds herein described can have a high binding affinity to sortilin and thus can specifically target cancer cells expressing or overexpressing sortilin.

The term "compound" as used in the present document refers to compounds of formulas (I), (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII), (XXIV) (XXV), (XXVI), (XXVII), (XXVIII), (XXIX), (XXX), (XXXI), (XXXII), (XXXIII), (XXXIV), (XXXV), (XXXVI), (XXXVII), (XXXVIII), (XXXIX), (XXXX), (XXXXI) or (XXXXII) or to pharmaceutically acceptable salts, solvates, hydrates and/or prodrugs of these compounds, isomers of these latter compounds, or racemic mixtures of these latter compounds, and/or to composition(s) made with such compound(s) as previously indicated in the present disclosure. The expression "compound" also refers to mixtures of the various compounds herein disclosed.

Compounds of the present disclosure include prodrugs. In general, such prodrugs will be functional derivatives of these compounds which are readily convertible in vivo into the compound from which it is notionally derived. Prodrugs of the compounds of the present disclosure may be conventional esters formed with available hydroxy, or amino group. For example, an available OH or nitrogen in a compound of the present disclosure may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In certain instances, the prodrugs of the compounds of the present disclosure are those in which one or more of the hydroxy groups in the compounds is masked as groups which can be converted to hydroxy groups in vivo. Conventional procedures for the selection and preparation of suitable prodrugs are described, for example, in "Design of Prodrugs" ed. H. Bundgaard, Elsevier, 1985.

Compounds of the present disclosure include radiolabeled forms, for example, compounds labeled by incorporation within the structure $^{2}H$, $_{3}H$, $^{14}C$, $^{15}N$, or a radioactive halogen such as $^{125}I$. A radiolabeled compound of the compounds of the present disclosure may be prepared using standard methods known in the art.

The expression "derivative thereof" as used herein when referring to a compound means a derivative of the compound that has a similar reactivity and that could be used as an alternative to the compound in order to obtain the same desired result.

The term "cancer" as used herein means a primary or a secondary cancer and includes a non-metastatic cancer and/or a metastatic cancer. Reference to cancer includes reference to cancer cells. For example, the cancer is ovarian cancer, brain cancer, breast cancer, melanoma, colorectal cancer, glioblastoma, liver cancer, lung cancer, prostate cancer, cervical cancer, head cancer, gastric cancer, kidney cancer, endometrial cancer, testis cancer, urothelial cancer, acute lymphoblastic leukemia, acute myeloid leukemia, Hodgkin lymphoma, neuroblastoma, non-Hodgkin lymphoma, soft tissue cancer, bone sarcoma, thyroid cancer, transitional cell bladder cancer, Wilm's tumour, glioma, pancreatic cancer or spleen cancer. The term "cancer" as used herein also comprises any cancer involving expression of sortilin.

The term "therapeutic agent" as used herein means an agent capable of producing a therapeutic effect by inhibiting, suppressing or reducing a cancer (e.g., as determined by clinical symptoms or the amount of cancerous cells) in a subject as compared to a control. Examples of therapeutic agents include for example anticancer agents and phytochemicals.

The term "anticancer agent" as used herein means an agent capable of causing toxicity in cancer cells. For example, taxanes, which are derived from the bark of the Pacific yew tree *Taxus brevifolia*, can be used as anticancer agents. Taxanes include for example paclitaxel, docetaxel and cabazitaxel. Other anticancer agents include for example anthracycline compounds which work by intercalating DNA. For example, anthracyclines include doxorubicin and daunorubicin.

The term "docetaxel" or "doce" as used herein means an anticancer agent having the structure:

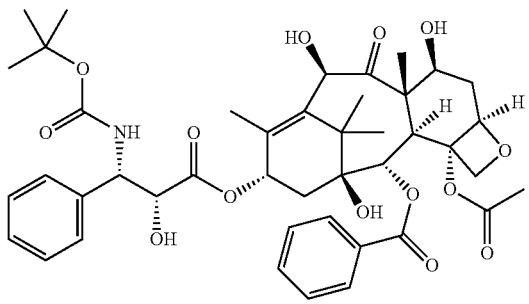

or pharmaceutically acceptable salts, solvates or prodrugs thereof as well as mixtures thereof. For example, docetaxel can be conjugated to a peptide compound of the present disclosure via the oxygen atom attached to the carbon atom at position 2 of its side chain. Docetaxel can be connected to the peptide compound directly or via a linker.

The term "doxorubicin" or "doxo" as used herein means an anticancer agent having the structure:

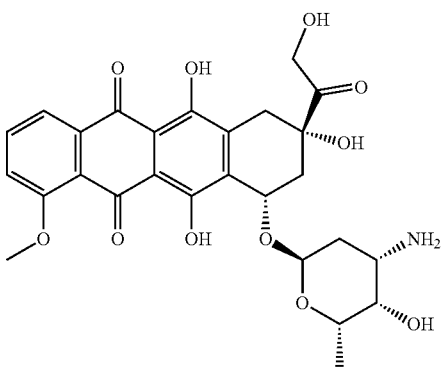 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]

or pharmaceutically acceptable salts, solvates or prodrugs thereof as well as mixtures thereof. For example, doxorubicin can be conjugated to a peptide compound of the present disclosure via the oxygen atom attached to the carbon atom at position 14. Doxorubicin can be connected to the peptide compound directly or via a linker.

The term "cabazitaxel" or "cab" as used herein means an anticancer agent having the structure:

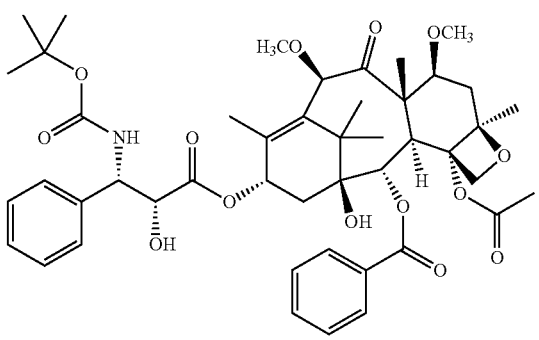 [SMILES: CO[C@H]1C(=O)[C@]2(C)[C@@H](OC)C[C@@]3(C)OC[C@@]3(OC(C)=O)[C@H]2[C@H](OC(=O)c2ccccc2)[C@]2(O)C[C@H](OC(=O)[C@H](O)[C@@H](NC(=O)OC(C)(C)C)c3ccccc3)C(C)=C1C2(C)C]

or pharmaceutically acceptable salts, solvates or prodrugs thereof as well as mixtures thereof. For example, cabazitaxel can be conjugated to a peptide compound of the present disclosure via the oxygen atom attached to the carbon atom at position 2 of its side chain. Cabazitaxel can be connected to the peptide compound directly or via a linker.

The term "phytochemical" as used herein means chemical compounds that occur naturally in plants and that can be used for treating a cancer. Examples of phytochemicals include for example Curcumin, Genistein, Resveratrol, Epigallocatechin-(3)-gallate (EGCG), Piperine, Sulforaphane, Quercetin, lupeol and ß-Carotene. Curcumin (diferuloylmethane) is a yellow pigment present in the spice turmeric (*Curcuma longa*) that has been associated with antioxidant, anti-inflammatory, anticancer, antiviral, and antibacterial activities as indicated by over 6,000 citations (Hosseini, 2015). Other phytochemicals that can be used include, without limitation, those shown below:

| | |
|---|---|
| Alkaloids | Monoterpenes |
| Chlorogenic acid | Geraniol |
| Theobromine | Limonene |
| Theophylline | Organosulfides |
| Anthocyanins | Allicin |
| Cyanidin | Glutathione |
| Malvidin | Indole-3-Carbinol |
| Carotenoids | Isothiocyanates |
| Beta-Carotene | Sulforaphane |
| Lutein | Other |
| Lycopene | Phytochemicals |
| Coumestans | Damnacanthal |
| Flavan-3-Ols | Digoxin |
| Flavonoids | Phytic acid |
| Epicatechin | Phenolic Acids |
| Catechins | Capsaicin |
| Hesperidin | Ellagic Acid |
| Isorhamnetin | Gallic acid |
| Kaempferol | Rosmarinic acid |
| Myricetin | Tannic Acid |
| Naringin | Phytosterols |
| Nobiletin | Beta-Sitosterol |
| Proanthocyanidins | Saponins |
| Quercetin | Stylbenes |
| Rutin | Pterostilbene |
| Tangeretin | Resveratrol |
| Hydroxycinnamic | Triterpenoids |
| Acids | Ursolic acid |
| Chicoric acid | Xanthophylls |
| Coumarin | Astaxanthin |
| Ferulic acid | Beta-Cryptoxanthin |
| Scopoletin | |
| Isoflavones | |
| Daidzein | |
| Genistein | |
| Lignans | |
| Silymarin | |
| Monophenols | |
| Hydroxytyrosol | |

The term "curcumin" or "cur" as used herein means a phytochemical having the structure:

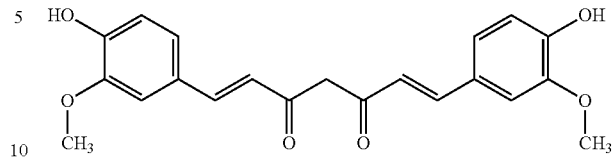

or pharmaceutically acceptable salts, solvates or prodrugs thereof as well as mixtures thereof. For example, curcumin can be conjugated to a peptide compound of the present disclosure via an oxygen atom of its phenol groups. Curcumin can be connected to the peptide compound directly or via a linker.

The term "conjugate compounds" or "peptide-drug conjugates" as used herein refers to compounds comprising a peptide compound herein disclosed connected to at least one therapeutic agent, optionally via a linker. Conjugate compounds can comprise, for example, 1, 2, 3 or 4 molecules of a therapeutic agent connected thereto. These 1-4 molecules of therapeutic agent can be the same or different i.e. up to four different therapeutic agents could be connected to the peptides. The therapeutic agent(s) are connected to the peptide via at least one covalent bond, at least one atom or at least one linker. Conjugate compounds can be used in the treatment of a cancer. Examples of conjugate compounds include, without limitation, the conjugate compounds shown below:

| Products | Amino acid sequences |
|---|---|
| | Docetaxel-conjugates |
| KBA-102 (3:1) | Succinyl-IK(docetaxel)LSGGVQAK(docetaxel)AGVINMFK(docetaxel)SESY - Formula (XIX)<br>that comprises the peptide compound having SEQ ID NO: 6 wherein each lysine residue has a docetaxel molecule connected thereto; and wherein a succinyl group is attached thereto at the N-terminal end |
| KBA-104 (2:1) | GVQAK(docetaxel)AGVINMFK(docetaxel)SESY - Formula (XV)<br>that comprises the peptide compound having SEQ ID NO: 8 wherein each lysine residue has a docetaxel molecule connected thereto; |
| KBA-105 (2:1) | Acetyl-GVRAK(docetaxel)AGVRNMFK(docetaxel)SESY - Formula (XX)<br>that comprises the peptide compound having SEQ ID NO: 14 wherein each lysine residue has a docetaxel molecule connected thereto |
| KBA-106 (2:1) | Acetyl-GVRAK(docetaxel)AGVRN(Nle)FK(docetaxel)SESY - Formula (XXI)<br>that comprises the peptide compound having SEQ ID NO: 15 wherein each lysine residue has a docetaxel molecule connected thereto |
| KBA-201 (2:1) | Acetyl-YK(docetaxel)SLRRK(docetaxel)APRWDAPLRDPALRQLL - Formula (XXII)<br>that comprises that comprises the peptide compound having SEQ ID NO: 16 wherein each lysine residue has a docetaxel molecule connected thereto |
| | Doxorubicin-conjugates |
| KBB-104 (2:1) | GVQAK(doxorubicin)AGVINMFK(doxorubicin)SESY - Formula (XXIII)<br>that comprises the peptide compound having SEQ ID NO: 8 wherein each lysine residue has a doxorubicin molecule connected thereto |
| KBB-106 (2:1) | Acetyl-GVRAK(doxorubicin)AGVRN(Nle)FK(doxorubicin)SESY - Formula (XXVI)<br>that comprises the peptide compound having SEQ ID NO: 15 wherein each lysine residue has a doxorubicin molecule connected thereto |
| KBB-201 (2:1) | Acetyl-YK(doxorubicin)SLRRK(doxorubicin)APRWDAPLRDPALRQLL - Formula (XXVII)<br>that comprises the peptide compound having SEQ ID NO: 16 wherein each lysine residue has a doxorubicin molecule connected thereto |

| Products | Amino acid sequences |
|---|---|
| | Curcumin-conjugates |
| KBC-106 (2:1) | Acetyl-GVRAK(curcumin)AGVRN(Nle)FK(curcumin)SESY - Formula (XXXV) that comprises the peptide compound having SEQ ID NO: 15 wherein each lysine residue has a curcumin molecule connected thereto |
| | Cabazitaxel-conjugates |
| KBD-105 (2:1) | Acetyl-GVRAK(cabazitaxel)AGVRNMFK(cabazitaxel)SESY - Formula (XXXI) that comprises the peptide compound having SEQ ID NO: 14 wherein each lysine residue has a cabazitaxel molecule connected thereto |
| KBD-106 (2:1) | Acetyl-GVRAK(cabazitaxel)AGVRN(Nle)FK(cabazitaxel)SESY - Formula (XXXII) that comprises the peptide compound having SEQ ID NO: 15 wherein each lysine residue has a cabazitaxel molecule connected thereto |
| KBD-201 (2:1) | Acetyl-YK(cabazitaxel)SLRRK(cabazitaxel)APRWDAPLRDPALRQLL - Formula (XXXIII) that comprises the peptide compound having SEQ ID NO: 16 wherein each lysine residue has a cabazitaxel molecule connected thereto |

The term "conjugating" au used herein, refers, for example, to the preparation of a conjugate as defined above. Such an action comprises connecting a peptide compound together with at least one therapeutic agent, optionally via a linker.

For example, the following are general chemical formulas of some conjugate compounds herein disclosed.

Docetaxel-Katana Peptide Conjugate:

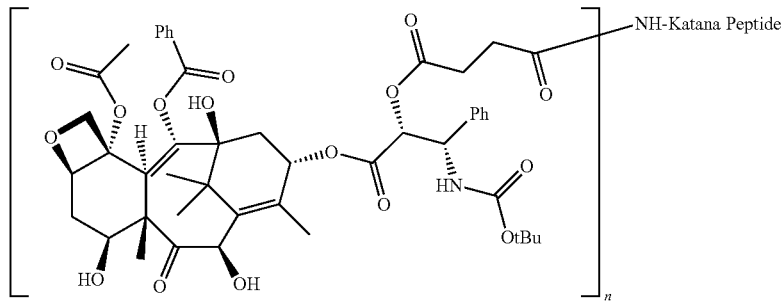

n = 1, 2, 3 or 4

Doxorubicin-Katana Peptide Conjugate:

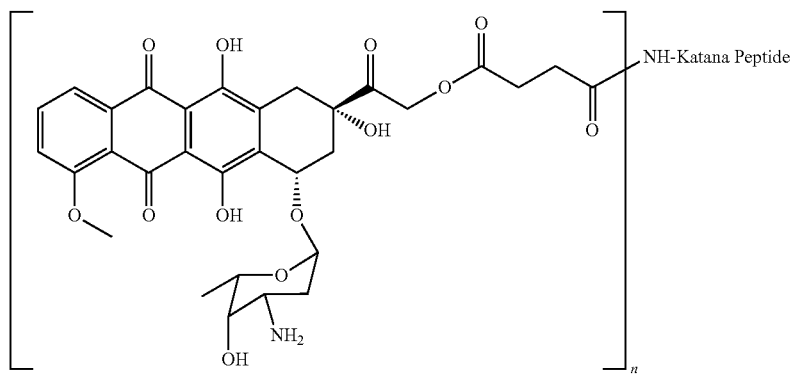

n = 1, 2, 3 or 4

Curcumin-Katana Peptide Conjugate:
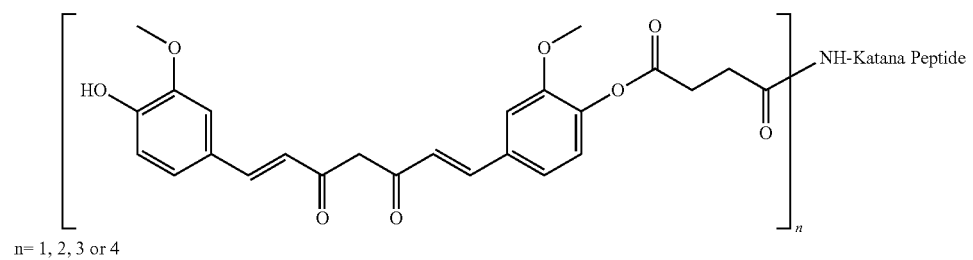
n= 1, 2, 3 or 4
For example, the following are the chemical structures of some conjugate compounds herein disclosed.

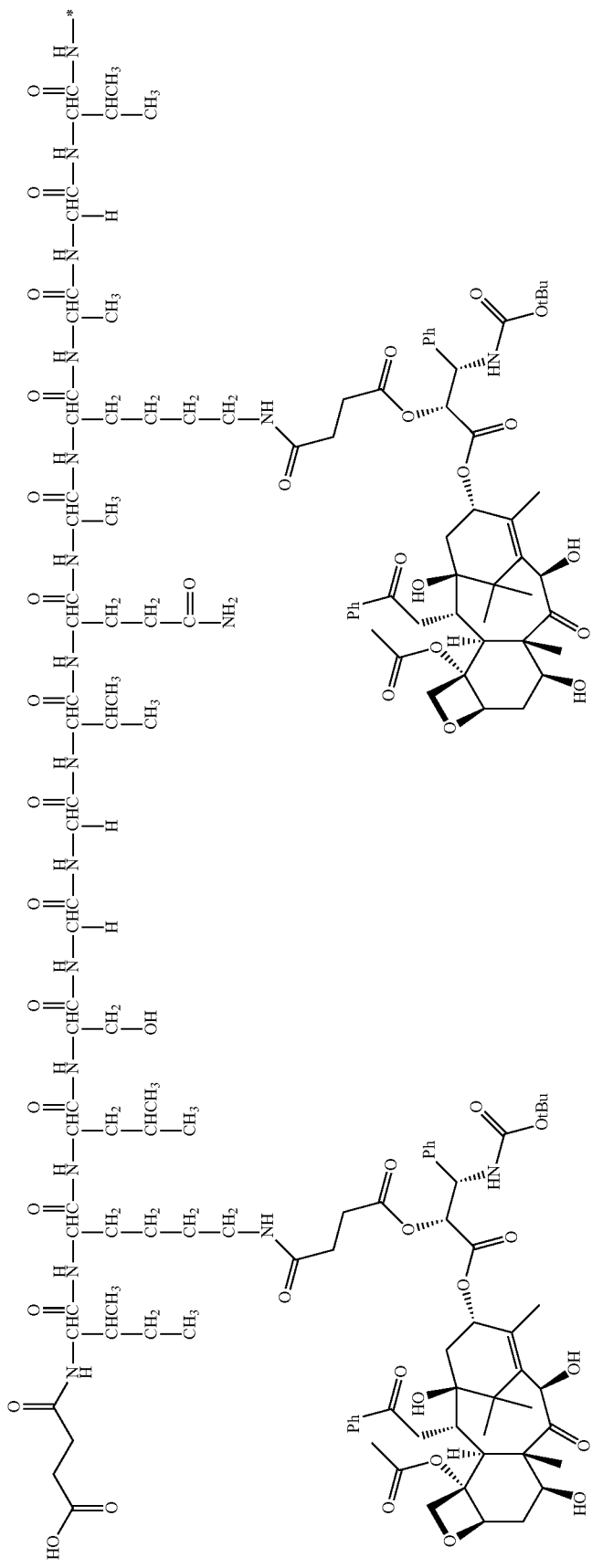

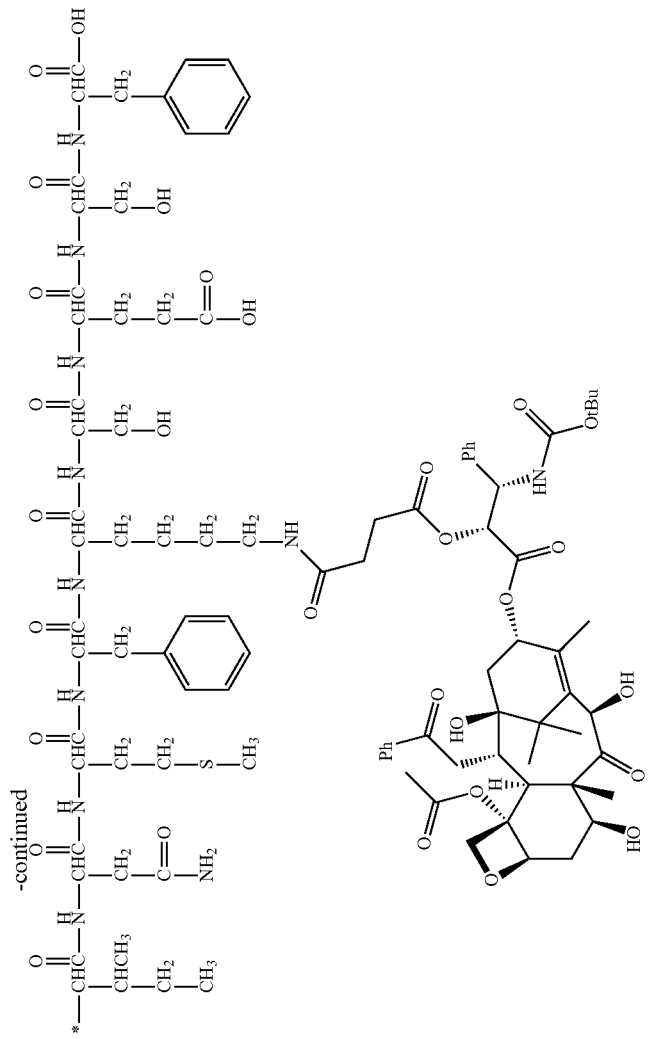
Chemical Formula: $C_{249}H_{340}N_{30}O_{82}S$
Molecular Weight: 5097.58

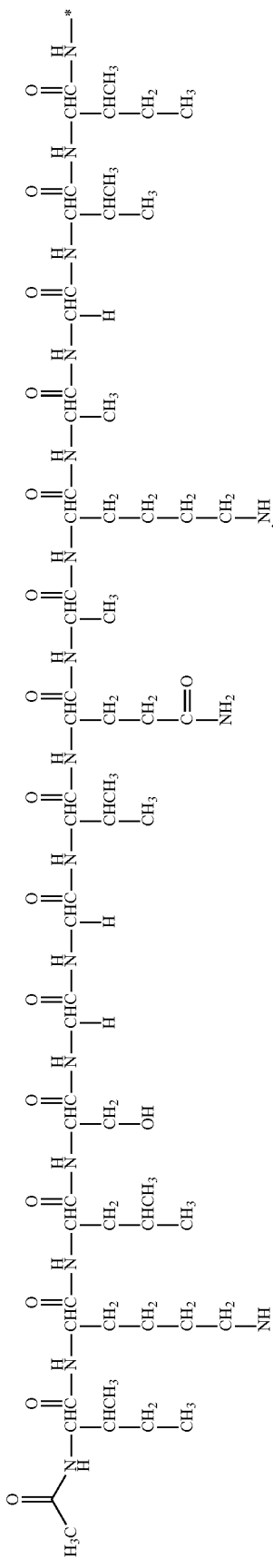
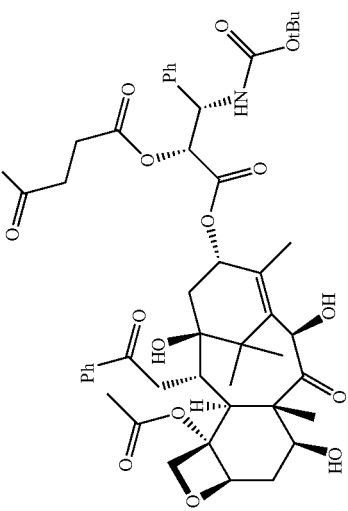
Docetaxel-KBP105 drug (2:1) or KBA-105:

-continued
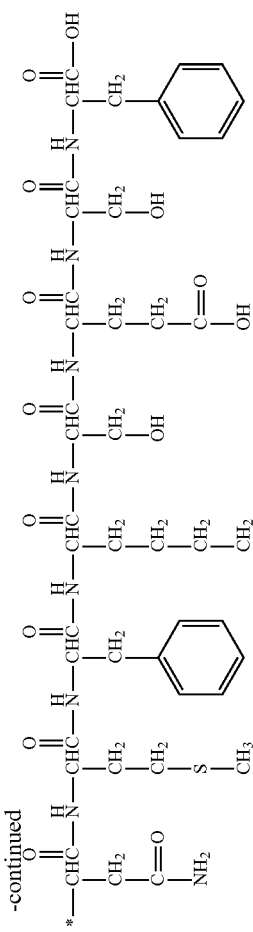
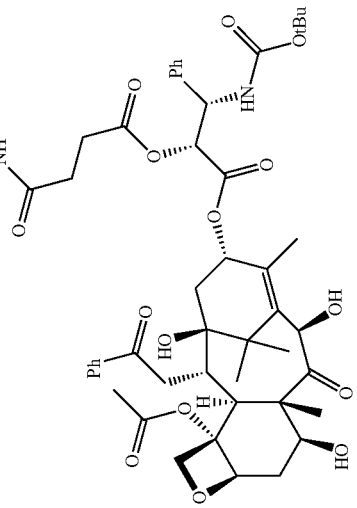
Chemical Formula: $C_{200}H_{283}N_{29}O_{64}S$
Molecular Weight: 4149.61

Curcumin-KBP-106 drug (2:1) or KBA-106:
KBC-106 - Curcumin
Ac-GVRAK(Cur)AGVRN(Nle)FK(Cur)SESY
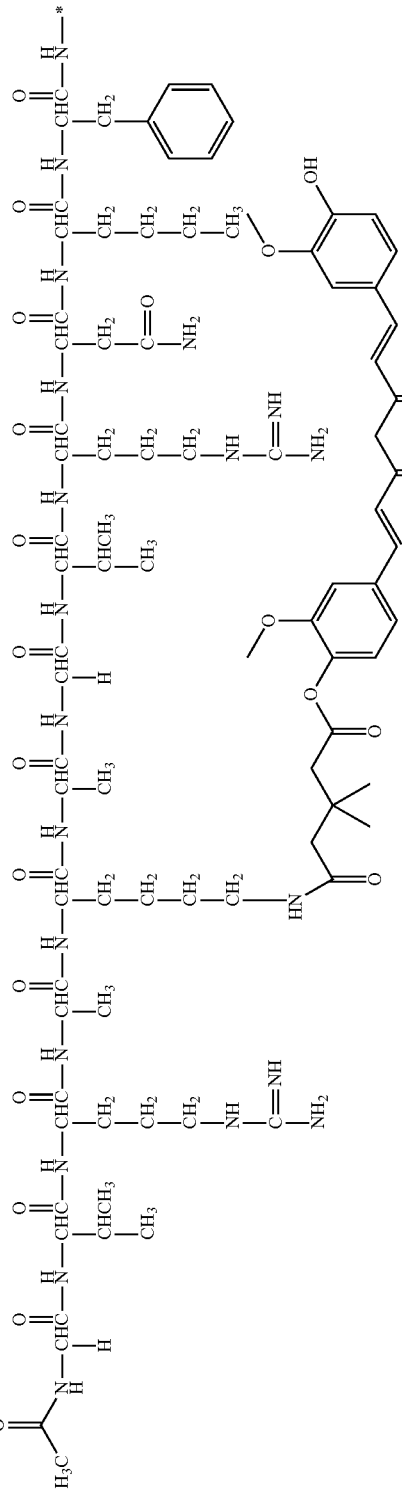
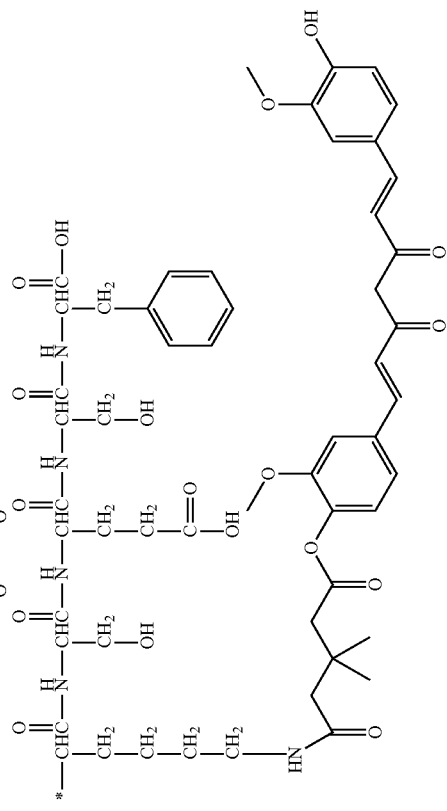
Chemical Formula: $C_{141}H_{194}N_{26}O_{41}$
Molecular Weight: 2909.24

The term "linker" as used herein means a chemical structure connecting a peptide compound herein disclosed to at least one therapeutic agent. The linker can be connected to the peptide compound at different functional groups on the peptide compounds. For example, the linker can be connected to the peptide compound at the primary amines (amines (—NH2): this group exists at the N-terminus of each polypeptide chain (called the alpha-amine) and in the side chain of lysine (Lys, K) residues (called the epsilon-amine). For example, the linker can be connected to the peptide compound at the carboxyls (—COOH): this group exists at the C-terminus of each polypeptide chain and in the side chains of aspartic acid (Asp, D) and glutamic acid (Glu, E). For example, the linker can be connected to the peptide compound at the Sulfhydryls (—SH): This group exists in the side chain of cysteine (Cys, C). Often, as part of a protein's secondary or tertiary structure, cysteines are joined together between their side chains via disulfide bonds (—S—S—). These must be reduced to sulfhydryls to make them available for crosslinking by most types of reactive groups. For example, the linker can be connected to the peptide compound at the Carbonyls (—CHO): Ketone or aldehyde groups can be created in glycoproteins by oxidizing the polysaccharide post-translational modifications (glycosylation) with sodium meta-periodate. For example, the linker can be a cleavable linker. For example, the linker can be a non-cleavable linker.

The following table summarizes the reactivity class and the chemical group of some of the principals linkers for standard chemical conjugation:

| Reactivity class | Chemical group |
|---|---|
| Carboxyl-to-amine reactive groups | Carbodiimide (e.g., EDC) |
| Amine-reactive groups | NHS ester |
| | Imidoester |
| | Pentafluorophenyl ester |
| | Hydroxymethyl phosphine |
| Sulfhydryl-reactive groups | Maleimide |
| | Haloacetyl (Bromo- or Iodo-) |
| | Pyridyldisulfide |
| | Thiosulfonate |
| | Vinylsulfone |
| Aldehyde-reactive groups i.e., oxidized sugars (carbonyls) | Hydrazide |
| | Alkoxyamine |
| Photoreactive groups | Diazirine |
| | Aryl Azide |

For example, homobifunctional and heterobifunctional crosslinkers can be used. For example, Disuccinimidyl suberate (DSS) is a homobifunctional crosslinker that has identical amine-reactive NHS-ester groups at either end of a short spacer arm. For example, Sulfosuccinimidyl 4-(N-maleimidomethyl)cyclohexane-1-carboxylate (Sulfo-SMCC) is a heterobifunctional crosslinker that has an amine-reactive sulfo-NHS-ester group at one end and a sulfhydryl reactive maleimide group at the opposite end of a cyclohexane spacer arm. This allows for sequential, two-step conjugation procedures. Among the commercially available homobifunctional cross-linkers are: BSOCOES (Bis(2-[Succinimidooxycarbonyloxy]ethyl) sulfone; DPDPB (1,4-Di-(3'-[2pyridyldithio]-propionamido) butane; DSS (disuccinimidyl suberate); DST (disuccinimidyl tartrate); Sulfo DST (sulfodisuccinimidyl tartrate); DSP (dithiobis(succinimidyl propionate); DTSSP (3,3'-Dithiobis (sulfosuccinimidyl propionate); EGS (ethylene glycol bis (succinimidyl succinate)); and BASED (Bis(p-[4-azidosalicylamido]-ethyl)disulfide iodinatable).

The polypeptides may be conjugated through a variety of linkers, e.g., sulfhydryl groups, amino groups (amines), or any appropriate reactive group. The linker can be a covalent bond. The linker group may comprise a flexible arm, e.g., 2, 3, 4, 5, 6, 7, 8, 9, 10, 11, 12, 13, 14, or 15 carbon atoms.

Exemplary linkers include, without limitation, pyridinedisulfide, thiosulfonate, vinylsulfonate, isocyanate, imidoester, diazine, hydrazine, thiol, carboxylic acid, multi-peptide linkers, and acetylene. Alternatively other linkers that can be used include $BS^3$ [Bis(sulfosuccinimidyl)suberate] (which is a homobifunctional N-hydroxysuccinimide ester that targets accessible primary amines), NHS/EDC (N-hydroxysuccinimide and 1-ethyl-3-(3-dimethylamino-propyl)carbodiimide (NHS/EDC allows for the conjugation of primary amine groups with carboxyl groups), sulfo-EMCS ([N-ε-maleimidocaproic acid]hydrazide (sulfo-EMCS are heterobifunctional reactive groups that are reactive toward sulfhydryl and amino groups), hydrazide (most proteins contain exposed carbohydrates and hydrazide is a useful reagent for linking carboxyl groups to primary amines).

To form covalent bonds, one can use as a chemically reactive group a wide variety of active carboxyl groups (e.g., esters) where the hydroxyl moiety is physiologically acceptable at the levels required to modify the peptide. Particular agents include for example N-hydroxysuccinimide (NHS), N-hydroxy-sulfosuccinimide (sulfo-NHS), maleimide-benzoyl-succinimide (MBS), gamma-maleimido-butyryloxy succinimide ester (GMBS), maleimido propionic acid (MPA), maleimido hexanoic acid (MHA), and maleimido undecanoic acid (MUA).

Primary amines are the principal targets for NHS esters; NHS esters react with primary amines to form covalent amide bonds. Accessible a-amine groups present on the N-termini of proteins and the ε-amine of lysine react with NHS esters. Thus, conjugated compounds herein disclosed can include a linker having a NHS ester conjugated to an N-terminal amino of a peptide or to an ε-amine of lysine. An amide bond is formed when the NHS ester reacts with primary amines releasing N-hydroxysuccinimide. Succinimide containing reactive groups may be referred to more simply as succinimidyl groups. In some embodiments, the functional group on the protein will be a thiol group and the chemically reactive group will be a maleimido-containing group such as gamma-maleimide-butylamide (GMBA or MPA). Such maleimide-containing groups may be referred to herein as maleido groups.

Amine-to-amine linkers include NHS esters, imidoesters, and others, examples of which are listed below.

Exemplary NHS esters:

DSG (disuccinimidyl glutarate)
DSS (disuccinimidyl suberate)
$BS^3$ (bis[sulfosuccinimidyl] suberate)
TSAT (tris-succinimidyl aminotriacetate)
Variants of bis-succinimide ester-activated compounds including a polyethylene glycol spacer such as $BS(PEG)_n$ where n is 1-20 (e.g., $BS(PEG)_5$ and $BS(PEG)_9$)
DSP (Dithiobis[succinimidyl propionate])
DTSSP (3,3'-dithiobis[sulfosuccinimidylpropionate])
DST (disuccinimidyl tartarate)
BSOCOES (bis[2-(succinimidooxycarbonyloxy)ethyl]sulfone)
EGS (ethylene glycol bis[succinimidylsuccinate])
sulfo-EGS (ethylene glycol bis[sulfosuccinimidylsuccinate])

Exemplary imidoesters:

DMA (dimethyl adipimidate•2 HCl)
DMP (dimethyl pimelimidate•2 HCl)
DMS (dimethyl suberimidate•2 HCl)
DTBP (dimethyl 3,3'-dithiobispropionimidate•2 HCl)

Other exemplary amine-to-amine linkers:

DFDNB (1,5-difluoro-2,4-dinitrobenzene)
THPP (β-[tris(hydroxymethyl) phosphino] propionic acid (betaine))

The linker may also be a sulfhydryl-to-sulfhydryl linker, such as the maleimides and pyridyldithiols listed below.

Exemplary maleimides:

BMOE (bis-maleimidoethane)
BMB (1,4-bismaleimidobutane)
BMH (bismaleimidohexane)
TMEA (tris[2-maleimidoethyl]amine)
BM(PEG)2 1,8-bis-maleimidodiethyleneglycol)
BM(PEG)$_n$, where n is 1 to 20 (e.g., 2 or 3)
BMDB (1,4 bismaleimidyl-2,3-dihydroxybutane)
DTME (dithio-bismaleimidoethane)

Another sulfhydryl linker:

HBVS (1,6-hexane-bis-vinylsulfone)

Exemplary pyridyldithiol:

DPDPB (1,4-di-[3'-(2'-pyridyldithio)-propionamido]butane)

The linker may be an amine-to-sulfhydryl linker, which includes NHS ester/maleimide compounds. Examples of these compounds are provided below.

Amine-to-sulfhydryl linkers:

AMAS (N-(α-maleimidoacetoxy)succinimide ester)
BMPS (N-[β-maleimidopropyloxy]succinimide ester)
GMBS (N-[γ-maleimidobutyryloxy]succinimide ester)
sulfo-GMBS (N-[γ-maleimidobutyryloxy]sulfosuccinimide ester)
MBS (m-maleimidobenzoyl-N-hydroxysuccinimide ester)
sulfo-MBS (m-maleimidobenzoyl-N-hydroxysulfosuccinimide ester)
SMCC (succinimidyl 4-[N-maleimidomethyl]cyclohexane-1-carboxylate)
sulfo-SMCC (Sulfosuccinimidyl 4-[N-maleimidomethyl]cyclohexane-1-carboxylate)
EMCS ([N-ε-maleimidocaproyloxy]succinimide ester)
Sulfo-EMCS ([N-ε-maleimidocaproyloxy]sulfosuccinimide ester)
SMPB (succinimidyl 4-[p-maleimidophenyl]butyrate)
sulfo-SMPB (sulfosuccinimidyl 4-[p-maleimidophenyl]butyrate)
SMPH (succinimidyl-6-[β-maleimidopropionamido]hexanoate)
LC-SMCC (succinimidyl-4-[N-maleimidomethyl]cyclohexane-1-carboxy-[6-amidocaproate])
sulfo-KMUS (N-[κ-maleimidoundecanoyloxy]sulfosuccinimide ester)
SM(PEG)$_n$ (succinimidyl-([N-maleimidopropionamido-polyethyleneglycol) ester), where n is 1 to 30 (e.g., 2, 4, 6, 8, 12, or 24)
SPDP (N-succinimidyl 3-(2-pyridyldithio)-propionate)
LC-SPDP (succinimidyl 6-(3-[2-pyridyldithio]-propionamido)hexanoate)
sulfo-LC-SPDP (sulfosuccinimidyl 6-(3'-[2-pyridyldithio]-propionamido)hexanoate)
SMPT (4-succinimidyloxycarbonyl-α-methyl-α-[2-pyridyldithio]toluene)
Sulfo-LC-SMPT (4-sulfosuccinimidyl-6-[α-methyl-α-(2-pyridyldithio)toluamido]hexanoate)
SIA (N-succinimidyl iodoacetate)
SBAP (succinimidyl 3-[bromoacetamido]propionate)
SIAB (N-succinimidyl[4-iodoacetyl]aminobenzoate)
sulfo-SIAB (N-sulfosuccinimidyl[4-iodoacetyl]aminobenzoate)

The linker can react with an amino group and a non-selective entity. Such linkers include NHS ester/aryl azide and NHS ester/diazirine linkers, examples of which are listed below.

NHS ester/aryl azide linkers:

NHS-ASA (N-hydroxysuccinimidyl-4-azidosalicylic acid)
ANB-NOS (N-5-azido-2-nitrobenzoyloxysuccinimide)
sulfo-HSAB (N-hydroxysulfosuccinimidyl-4-azidobenzoate)
sulfo-NHS-LC-ASA (sulfosuccinimidyl[4-azidosalicylamido]hexanoate)
SANPAH (N-succinimidyl-6-(4'-azido-2'-nitrophenylamino)hexanoate)
sulfo-SANPAH (N-sulfosuccinimidyl-6-(4'-azido-2'-nitrophenylamino)hexanoate)
sulfo-SFAD (sulfosuccinimidyl-(perfluoroazidobenzamido)-ethyl-1,3'-dithioproprionate)
sulfo-SAND (sulfosuccinimidyl-2-(m-azido-o-nitrobenzamido)-ethyl-1,3'-proprionate)
sulfo-SAED (sulfosuccinimidyl 2-[7-amino-4-methylcoumarin-3-acetamido]ethyl-1,3'dithiopropionate)

NHS ester/diazirine linkers:

SDA (succinimidyl 4,4'-azipentanoate)
LC-SDA (succinimidyl 6-(4,4'-azipentanamido)hexanoate)
SDAD (succinimidyl 2-([4,4'-azipentanamido]ethyl)-1,3'-dithioproprionate)
sulfo-SDA (sulfosuccinimidyl 4,4'-azipentanoate)
sulfo-LC-SDA (sulfosuccinimidyl 6-(4,4'-azipentanamido)hexanoate)
sulfo-SDAD (sulfosuccinimidyl 2-([4,4'-azipentanamido]ethyl)-1,3'-dithioproprionate)

Exemplary amine-to-carboxyl linkers include carbodiimide compounds (e.g., DCC (N,N-dicyclohexylcarbodiimide) and EDC (1-ethyl-3-[3-dimethylaminopropyl]carbodiimide)). Exemplary sulfhydryl-to-nonselective linkers include pyridyldithiol/aryl azide compounds (e.g., APDP ((N-[4-(p-azidosalicylamido)butyl]-3'-(2'-pyridyldithio)propionamide)). Exemplary sulfhydryl-to-carbohydrate linkers include maleimide/hydrazide compounds (e.g., BMPH (N-[β-maleimidopropionic acid]hydrazide), EMCH ([N-ε-maleimidocaproic acid]hydrazide), MPBH 4-(4-N-maleimidophenyl)butyric acid hydrazide), and KMUH (N-[κ-maleimidoundecanoic acid]hydrazide)) and pyridyldithiol/hydrazide compounds (e.g., PDPH (3-(2-pyridyldithio) propionyl hydrazide)). Exemplary carbohydrate-to-nonselective linkers include hydrazide/aryl azide compounds (e.g., ABH (p-azidobenzoyl hydrazide)). Exemplary hydroxyl-to-sulfhydryl linkers include isocyanate/maleimide compounds (e.g., (N-[p-maleimidophenyl]isocyanate)). Exemplary amine-to-DNA linkers include NHS ester/psoralen compounds (e.g., SPB (succinimidyl-[4-(psoralen-8-yloxy)]-butyrate)).

To generate a branch point of varying complexity in a conjugate peptide, the linker can be capable of linking 3-7 entities.

| Exemplary tri-functional linkers: | | |
|---|---|---|
| TMEA; Tris-(2-maleimidoethyl)amine) 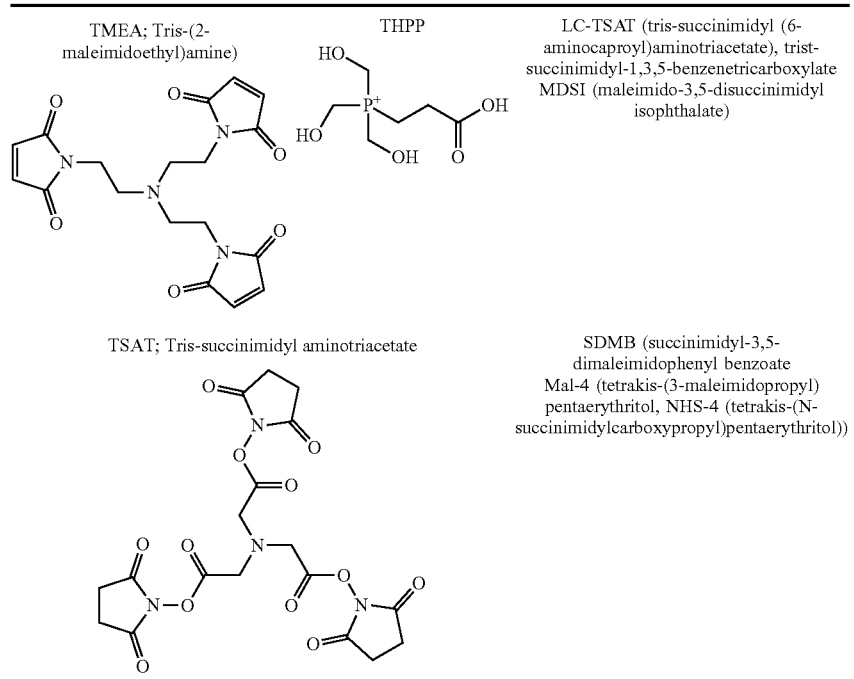 | THPP 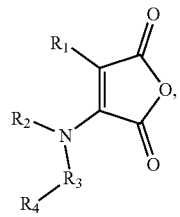 | LC-TSAT (tris-succinimidyl (6-aminocaproyl)aminotriacetate), trist-succinimidyl-1,3,5-benzenetricarboxylate MDSI (maleimido-3,5-disuccinimidyl isophthalate) |
| TSAT; Tris-succinimidyl aminotriacetate | | SDMB (succinimidyl-3,5-dimaleimidophenyl benzoate Mal-4 (tetrakis-(3-maleimidopropyl) pentaerythritol, NHS-4 (tetrakis-(N-succinimidylcarboxypropyl)pentaerythritol)) |

TMEA and TSAT reach through their maleimide groups with sulfhydryl groups. The hydroxyl groups and carboxy group of THPP can react with primary or secondary amines. Other useful linkers conform to the formula Y=C=N-Q-A-C(O)—Z, where Q is a homoaromatic or heteroaromatic ring system; A is a single bond or an unsubstituted or substituted divalent $C_{1-30}$ bridging group, Y is O or S; and Z is Cl, Br, I, $N_3$, N-succinimidyloxy, imidazolyl, 1-benzotriazolyloxy, OAr where Ar is an electron-deficient activating aryl group, or OC(O)R where R is -A-Q-N=C=Y or $C_4$-20 tertiary-alkyl (see U.S. Pat. No. 4,680,338).

Other useful linkers have the formula

where $R_1$ is H, $C_{1-6}$ alkyl, $C_{2-6}$ alkenyl, $C_{6-12}$ aryl or aralkyl or these coupled with a divalent organic —O—, —S—, or $$\diagdown_{N}\diagup^{R'}$$

where R' is $C_{1-6}$ alkyl, linking moiety; $R_2$ is H, $C_{1-12}$ alkyl, $C_{6-12}$ aryl, or $C_{6-12}$ aralkyl, $R_3$ is

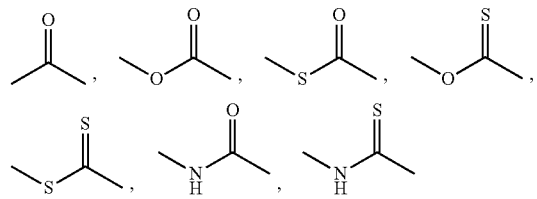

or another chemical structure that is able to delocalize the lone pair electrons of the adjacent nitrogen and $R_4$ is a pendant reactive group capable of linking $R_3$ to a peptide vector or to an agent (see for example U.S. Pat. No. 5,306,809).

The linker may include at least one amino acid residue and can be a peptide of at least or about 2, 3, 4, 5, 6, 7, 10, 15, 20, 25, 30, 40, or 50 amino acid residues. Where the linker is a single amino acid residue it can be any naturally or non-naturally occurring amino acid (e.g., Gly or Cys). Where the linker is a short peptide, it can be a glycine-rich peptide (which tend to be flexible) such as a peptide having the sequence [Gly-Gly-Gly-Gly-Ser]$_n$ where n is an integer from 1 to 6, inclusive (see U.S. Pat. No. 7,271,149) or a serine-rich peptide linker (see U.S. Pat. No. 5,525,491). Serine rich peptide linkers include those of the formula [X—X—X—X-Gly], where up to two of the X are Thr, the remaining X are Ser, and y is an integer from 1 to 5, inclusive (e.g., Ser-Ser-Ser-Ser-Gly, where y is greater than 1). Other linkers include rigid linkers (e.g., PAPAP and (PT)$_n$P, where n is 2, 3, 4, 5, 6, or 7) and a-helical linkers (e.g., A(EAAAK)$_n$A, where n is 1, 2, 3, 4, or 5).

The linker can be an aliphatic linker (e.g., with an amide bond to the polypeptide and an ester bond to the therapeutic agent). Where an aliphatic linker is used, it may vary with regard to length (e.g. $C_1$-$C_{20}$) and the chemical moieties it includes (e.g., an amino group or carbamate).

Examples of suitable amino acid linkers are succinic acid, Lys, Glu, and Asp, or a dipeptide such as Gly-Lys. When the linker is succinic acid, one carboxyl group thereof may form an amide bond with an amino group of the amino acid residue, and the other carboxyl group thereof may, for example, form an amide bond with an amino group of the peptide or substituent. When the linker is Lys, Glu, or Asp, the carboxyl group thereof may form an amide bond with an amino group of the amino acid residue, and the amino group thereof may, for example, form an amide bond with a carboxyl group of the substituent. When Lys is used as the linker, a further linker may be inserted between the ε-amino group of Lys and the substituent. The further linker may be succinic acid, which can form an amide bond with the ε-amino group of Lys and with an amino group present in the substituent. In one embodiment, the further linker is Glu or Asp (e.g., which forms an amide bond with the ε-amino group of Lys and another amide bond with a carboxyl group present in the substituent), that is, the substituent is a Nε-acylated lysine residue.

The linker can also be a branched polypeptide. Exemplary branched peptide linkers are described in U.S. Pat. No. 6,759,509.

The linker can provide a cleavable linkage (e.g., a thioester linkage) or a non-cleavable linkage (e.g., a maleimide linkage). For example, a cytotoxic protein can be bound to a linker that reacts with modified free amines, which are present at lysine residues within the polypeptide and at the amino-terminus of the polypeptide. Thus, linkers useful in the present conjugate compounds can comprise a group that is reactive with a primary amine on the polypeptide or modified polypeptide to which the therapeutic agent moiety is conjugated. More specifically, the linker can be selected from the group consisting of monofluoro cyclooctyne (MFCO), bicyclo[6.1.0]nonyne (BCN), N-succinimidyl-S-acetylthioacetate (SATA), N-succinimidyl-S-acetylthiopropionate (SATP), maleimido and dibenzocyclooctyne ester (a DBCO ester). Useful cyclooctynes, within a given linker, include OCT, ALO, MOFO, DIFO, DIBO, BARAC, DIBAC, and DIMAC.

The linker may comprise a flexible arm, such as for example, a short arm (<2 carbon chain), a medium-size arm (from 2-5 carbon chain), or a long arm (3-6 carbon chain).

Click chemistry can also be used for conjugation on a peptide (DBCO, TCO, tetrazine, azide and alkyne linkers). These families of linkers can be reactive toward amine, carboxyl and sulfhydryl groups. In addition, these linkers can also be biotinylated, pegylated, modified with a fluorescent imaging dye, or phosphoramidited for incorporation onto an oligonucleotide sequence.

The term "intermediate" as used herein refers to a therapeutic agent that has been reacted with a linker thereby forming an intermediate or an activated form of the therapeutic agent. The intermediate can be reacted with a peptide compound herein disclosed thereby forming a conjugate compound herein disclosed that can be used for treating a cancer.

The term "amino acid" refers to the common natural (genetically encoded) or synthetic amino acids and common derivatives thereof, known to those skilled in the art. When applied to amino acids, "standard" or "proteinogenic" refers to the genetically encoded 20 amino acids in their natural configuration. Similarly, when applied to amino acids, "non-standard," "unnatural" or "unusual" refers to the wide selection of non-natural, rare or synthetic amino acids such as those described by Hunt, S. in *Chemistry and Biochemistry of the Amino Acids*, Barrett, G. C., ed., Chapman and Hall: New York, 1985. Some examples of non-standard amino acids include non-alpha amino acids, D-amino acids.

Abbreviations used for amino acids and designation of peptides follow the rules of the IUPAC-IUB Commission of Biochemical Nomenclature in J. Biol. Chem. 1972, 247, 977-983. This document has been updated: Biochem. J., 1984, 219, 345-373; Eur. J. Biochem., 1984, 138, 9-37; 1985, 152, 1; Int. J. Pept. Prot. Res., 1984, 24, following p 84; J. Biol. Chem., 1985, 260, 14-42; Pure Appl. Chem. 1984, 56, 595-624; Amino Acids and Peptides, 1985, 16, 387-410; and in *Biochemical Nomenclature and Related Documents*, 2$^{nd}$ edition, Portland Press, 1992, pp 39-67. Extensions to the rules were published in the JCBN/NC-IUB Newsletter 1985, 1986, 1989; see *Biochemical Nomenclature and Related Documents*, 2$^{nd}$ edition, Portland Press, 1992, pp 68-69.

The term "antagonist" refers to a compound that reduces at least some of the effect of the endogenous ligand of a protein, receptor, enzyme, interaction, or the like.

The term "inhibitor" refers to a compound that reduces the normal activity of a protein, receptor, enzyme, interaction, or the like.

The term "inverse agonist" refers to a compound that reduces the activity of a constitutively-active receptor below its basal level.

The term "library" refers to a collection of compounds that can be used for example for drug discovery purposes. For example, the library compounds can be peptide compounds and/or conjugate compounds herein disclosed.

The term "mixture" as used herein, means a composition comprising two or more compounds. In an embodiment a mixture is a mixture of two or more distinct compounds. In a further embodiment, when a compound is referred to as a "mixture", this means that it can comprise two or more "forms" of the compounds, such as, salts, solvates, prodrugs or, where applicable, stereoisomers of the compound in any ratio. A person of skill in the art would understand that a compound in a mixture can also exist as a mixture of forms. For example, a compound may exist as a hydrate of a salt or as a hydrate of a salt of a prodrug of the compound. All forms of the compounds disclosed herein are within the scope of the present application.

The term "modulator" refers to a compound that imparts an effect on a biological or chemical process or mechanism. For example, a modulator may increase, facilitate, upregulate, activate, inhibit, decrease, block, prevent, delay, desensitize, deactivate, down regulate, or the like, a biological or chemical process or mechanism. Accordingly, a modulator can be an "agonist" or an "antagonist." Exemplary biological processes or mechanisms affected by a modulator include, but are not limited to, enzyme binding, receptor binding and hormone release or secretion. Exemplary chemical processes or mechanisms affected by a modulator include, but are not limited to, catalysis and hydrolysis.

The term "peptide" refers to a chemical compound comprising at least two amino acids covalently bonded together using amide bonds.

The term "prodrug" as used herein refers to a derivative of an active form of a known compound or composition which derivative, when administered to a subject, is gradually converted to the active form to produce a better therapeutic response and/or a reduced toxicity level. In general, prodrugs will be functional derivatives of the compounds disclosed herein which are readily convertible in vivo into the compound from which it is notionally derived. Prodrugs include, without limitation, acyl esters, carbonates, phosphates, and urethanes. These groups are exemplary and not exhaustive, and one skilled in the art could prepare other known varieties of prodrugs. Prodrugs may be, for example, formed with available hydroxy, thiol, amino or carboxyl groups. For example, the available OH and/or $NH_2$ in the compounds of the disclosure may be acylated using an activated acid in the presence of a base, and optionally, in inert solvent (e.g. an acid chloride in pyridine). Some common esters which have been utilized as prodrugs are phenyl esters, aliphatic ($C_1$-$C_{24}$) esters, acyloxymethyl esters, carbamates and amino acid esters. In certain instances, the prodrugs of the compounds of the disclosure are those in which the hydroxy and/or amino groups in the compounds is masked as groups which can be converted to hydroxy and/or amino groups in vivo. Conventional procedures for the selection and preparation of suitable prodrugs are described, for example, in "Design of Prodrugs" ed. H. Bundgaard, Elsevier, 1985.

The term "protecting group" refers to any chemical compound that may be used to prevent a potentially reactive functional group, such as an amine, a hydroxyl or a carboxyl, on a molecule from undergoing a chemical reaction while chemical change occurs elsewhere in the molecule. A number of such protecting groups are known to those skilled in the art and examples can be found in *Protective Groups in Organic Synthesis*, T. W. Greene and P. G. Wuts, eds., John Wiley & Sons, New York, 4$^{th}$ edition, 2006, 1082 pp, ISBN 9780471697541. Examples of amino protecting groups include, but are not limited to, phthalimido, trichloroacetyl, benzyloxycarbonyl, tert butoxycarbonyl, and adamantyl-oxycarbonyl. In some embodiments, amino protecting groups are carbamate amino protecting groups, which are defined as an amino protecting group that when bound to an amino group forms a carbamate. In other embodiments, amino carbamate protecting groups are allyloxycarbonyl (Alloc), benzyloxycarbonyl (Cbz), 9 fluorenylmethoxycarbonyl (Fmoc), tert-butoxycarbonyl (Boc) and α,α dimethyl-3,5 dimethoxybenzyloxycarbonyl (Ddz). For a recent discussion of newer nitrogen protecting groups see: Tetrahedron 2000, 56, 2339-2358. Examples of hydroxyl protecting groups include, but are not limited to, acetyl, tert-butyldimethylsilyl (TBDMS), trityl (Trt), tert-butyl, and tetrahydropyranyl (THP). Examples of carboxyl protecting groups include, but are not limited to, methyl ester, tert-butyl ester, benzyl ester, trimethylsilylethyl ester, and 2,2,2-trichloroethyl ester.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule of the present disclosure. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

The expression "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "solid phase chemistry" refers to the conduct of chemical reactions where one component of the reaction is covalently bonded to a polymeric material (solid support as defined below). Reaction methods for performing chemistry on solid phase have become more widely known and established outside the traditional fields of peptide and oligonucleotide chemistry (*Solid-Phase Synthesis: A Practical Guide*, F. Albericio, ed., CRC Press, 2000, 848 pp, ISBN: 978-0824703592; *Organic Synthesis on Solid Phase, 2nd* edition, Florencio Zaragoza Dörwald, Wiley-VCH, 2002, 530 pp, ISBN: 3-527-30603-X; *Solid-Phase Organic Synthesis: Concepts, Strategies, and Applications*, P. H. Toy, Y. Lam, eds., Wiley, 2012, 568 pp, ISBN: 978-0470599143).

The term "solid support," "solid phase" or "resin" refers to a mechanically and chemically stable polymeric matrix utilized to conduct solid phase chemistry. This is denoted by "Resin," "P—" or the following symbol: ◯—.

Examples of appropriate polymer materials include, but are not limited to, polystyrene, polyethylene, polyethylene glycol (PEG, including, but not limited to, ChemMatrix® (Matrix Innovation, Quebec, Quebec, Canada; J. Comb. Chem. 2006, 8, 213-220)), polyethylene glycol grafted or covalently bonded to polystyrene (also termed PEG-polystyrene, TentaGel™, Rapp, W.; Zhang, L.; Bayer, E. In Innovations and Perspectives in Solid Phase Synthesis. Peptides, Polypeptides and Oligonucleotides; Epton, R., ed.; SPCC Ltd.: Birmingham, UK; p 205), polyacrylate (CLEAR™) polyacrylamide, polyurethane, PEGA [polyethyleneglycol poly(N,N dimethyl-acrylamide) co-polymer, Tetrahedron Lett. 1992, 33, 3077-3080], cellulose, etc. These materials can optionally contain additional chemical agents to form cross-linked bonds to mechanically stabilize the structure, for example polystyrene cross-linked with divinylbenezene (DVB, usually 0.1-5%, preferably 0.5-2%). This solid support can include as non-limiting examples aminomethyl polystyrene, hydroxymethyl polystyrene, benzhydrylamine polystyrene (BHA), methylbenzhydrylamine (MBHA) polystyrene, and other polymeric backbones containing free chemical functional groups, most typically, $NH_2$ or —OH, for further derivatization or reaction. The term is also meant to include "Ultraresins" with a high proportion ("loading") of these functional groups such as those prepared from polyethyleneimines and cross-linking molecules (J. Comb. Chem. 2004, 6, 340-349). At the conclusion of the synthesis, resins are typically discarded, although they have been shown to be able to be recycled (Tetrahedron Lett. 1975, 16, 3055).

In general, the materials used as resins are insoluble polymers, but certain polymers have differential solubility depending on solvent and can also be employed for solid phase chemistry. For example, polyethylene glycol can be utilized in this manner since it is soluble in many organic solvents in which chemical reactions can be conducted, but it is insoluble in others, such as diethyl ether. Hence, reactions can be conducted homogeneously in solution, then the product on the polymer precipitated through the addition of diethyl ether and processed as a solid. This has been termed "liquid-phase" chemistry.

The expression "pharmaceutically acceptable" means compatible with the treatment of subjects such as animals or humans.

The expression "pharmaceutically acceptable salt" means an acid addition salt or basic addition salt which is suitable for or compatible with the treatment of subjects such as animals or humans.

The expression "pharmaceutically acceptable acid addition salt" as used herein means any non-toxic organic or inorganic salt of any compound of the present disclosure, or any of its intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluenesulfonic and methanesulfonic acids. Either the mono or di-acid salts can be formed, and such salts may exist in either a hydrated, solvated or substantially anhydrous form. In general, the acid addition salts of the compounds of the present disclosure are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the present disclosure, for laboratory use, or for subsequent conversion to a pharmaceutically acceptable acid addition salt.

The term "pharmaceutically acceptable basic addition salt" as used herein means any non-toxic organic or inorganic base addition salt of any acid compound of the disclosure, or any of its intermediates. Acidic compounds of the disclosure that may form a basic addition salt include, for example, where $CO_2H$ is a functional group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the isolation of the compounds of the disclosure, for laboratory use, or for subsequent conversion to a pharmaceutically acceptable acid addition salt.

The formation of a desired compound salt is achieved using standard techniques. For example, the neutral compound is treated with an acid or base in a suitable solvent and the formed salt is isolated by filtration, extraction or any other suitable method.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

The term "subject" as used herein includes all members of the animal kingdom including mammals such as a mouse, a rat, a dog and a human.

The terms "suitable" and "appropriate" mean that the selection of the particular group or conditions would depend on the specific synthetic manipulation to be performed and the identity of the molecule but the selection would be well within the skill of a person trained in the art. All process steps described herein are to be conducted under conditions suitable to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression a "therapeutically effective amount", "effective amount" or a "sufficient amount" of a compound or composition of the present disclosure is a quantity sufficient to, when administered to the subject, including a mammal, for example a human, effect beneficial or desired results, including clinical results, and, as such, a "therapeutically effective amount" or an "effective amount" depends upon the context in which it is being applied. For example, in the context of treating cancer, it is an amount of the compound or composition sufficient to achieve such treatment of the cancer as compared to the response obtained without administration of the compound or composition. The amount of a given compound or composition of the present disclosure that will correspond to an effective amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" or "effective amount" of a compound or composition of the present disclosure is an amount which inhibits, suppresses or reduces a cancer (e.g., as determined by clinical symptoms or the amount of cancerous cells) in a subject as compared to a control.

As used herein, and as well understood in the art, "treatment" or "treating" is an approach for obtaining beneficial or desired results, including clinical results. Beneficial or desired clinical results can include, but are not limited to, decrease in tumour progression, decrease in tumour size, decrease in tumour growth rate, decrease in tumor invasion and metastatic potential, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" or "treating" can also mean prolonging survival as compared to expected survival if not receiving treatment.

The term "tolerability" or "tolerated" as used herein means a degree to which a therapeutic agent may be endured or accepted by a subject treated with the therapeutic agent. For example, tolerability may be assessed by measuring different parameters such as (i) maintaining or absence of weight loss, (ii) duration of treatment withstood and (iii) decrease or absence of side effects. For example, it is well established that a therapeutic agent is tolerated by a subject when there is no weight loss observed during treatment using such a therapeutic agent.

The term "administered" or "administering" as used herein means administration of a therapeutically effective amount of a compound or composition of the application to a cell either in vitro (e.g. a cell culture) or in vivo (e.g. in a subject).

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this specification and the appended claims, the singular forms "a", "an" and "the" include plural references unless the content clearly dictates otherwise. Thus for example, a composition containing "a compound" includes a mixture of two or more compounds. It should also be noted that the term "or" is generally employed in its sense including "and/or" unless the content clearly dictates otherwise.

In compositions comprising an "additional" or "second" component, the second component as used herein is chemically different from the other components or first component. A "third" component is different from the other, first, and second components, and further enumerated or "additional" components are similarly different.

The definitions and embodiments described in particular sections are intended to be applicable to other embodiments herein described for which they are suitable as would be understood by a person skilled in the art.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

A platform allowing the transport of therapeutic agents into cancer cells for new therapies directed against primary and secondary tumours has recently been developed. This approach utilizes peptide compounds derived from bacterial proteins or from ligands of receptors expressed in cancer cells (ex. sortilins/syndecans). In the present disclosure, the conjugation of anticancer agents and phytochemicals to one of these peptide compounds is described. For example, anticancer agents, for example Docetaxel, Cabazitaxel and Doxorubicin, can be conjugated to the peptide compounds. Phytochemicals, for example curcumin, can also be conjugated to the peptide compounds. Moreover, after conjugation to Katana peptide, uptake of the conjugated Katana peptide is unaffected by the P-gp inhibitor Cyclosporine A, confirming that Katana-peptides are not substrates for efflux pumps such as P-gp. These results further indicate that these peptide-drug conjugates could be used in other applications outside of oncology. In addition to inducing greater tumour apoptosis compared to unconjugated therapeutic agent, the conjugate compounds herein described may also provide greater tolerability and reduced toxicity.

Disclosed herein are peptide compounds as well as conjugate compounds comprising at least one therapeutic agent connected to a peptide compound. Such compounds can be used for the treatment of cancer, for example a cancer involving sortilin expression.

Accordingly, a first aspect is a peptide compound having at least 80% sequence identity to a compound chosen from compounds of formula (I), formula (II), formula (III), formula (IV), formula (V), formula (VI), formula (VII), formula (VIII), formula (IX), formula (X), formula (XI), formula (XII) and formula (XIII):

$X_1X_2X_3X_4X_5GVX_6AKAGVX_7NX_8FKSESY$ (SEQ ID NO: 1)
(I)

$(X_9)_nGVX_{10}AKAGVX_{11}NX_{12}FKSESY$ (SEQ ID NO: 2)
(II)

$YKX_{13}LRRX_{14}APRWDX_{15}PLRDPALRX_{16}X_{17}L$ (SEQ ID NO: 3)
(III)

$YKX_{18}LRR(X_{19})_nPLRDPALRX_{20}X_{21}L$ (SEQ ID NO: 4)
(IV)

IKLSGGVQAKAGVINMDKSESM (SEQ ID NO: 5)
(V)

IKLSGGVQAKAGVINMFKSESY (SEQ ID NO: 6)
(VI)

IKLSGGVQAKAGVINMFKSESYK (SEQ ID NO: 7)
(VII)

GVQAKAGVINMFKSESY (SEQ ID NO: 8)
(VIII)

GVRAKAGVRNMFKSESY (SEQ ID NO: 9)
(IX)

GVRAKAGVRN(Nle)FKSESY (SEQ ID NO: 10)
(X)

YKSLRRKAPRWDAPLRDPALRQLL (SEQ ID NO: 11)
(XI)

YKSLRRKAPRWDAYLRDPALRQLL (SEQ ID NO: 12)
(XII)

YKSLRRKAPRWDAYLRDPALRPLL (SEQ ID NO: 13)
(XIII)

wherein
$X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{18}$ and $X_{19}$ are independently chosen from any amino acid;

$X_{16}$, $X_{17}$, $X_{20}$ and $X_{21}$ are independently chosen from Q, P, Y, I and L;

n is 0, 1, 2, 3, 4 or 5, when $X_9$ is present more than once, each of said $X_9$ is independently chosen from any amino acid;

when $X_{19}$ is present more than once, each of said $X_9$ is independently chosen from any amino acid and wherein at least one protecting group and/or at least one labelling agent is optionally connected to said peptide at an N- and/or C-terminal end.

For example, the peptide compound is a peptide compound that comprises:

$X_1X_2X_3X_4X_5GVX_6AKAGVX_7NX_8FKSESY$ (SEQ ID NO: 1)
(I)

$(X_9)_nGVX_{10}AKAGVX_{11}NX_{12}FKSESY$ (SEQ ID NO: 2)
(II)

$YKX_{13}LRRX_{14}APRWDX_{15}PLRDPALRX_{16}X_{17}L$ (SEQ ID NO: 3)
(III)

$YKX_{18}LRR(X_{19})_nPLRDPALRX_{20}X_{21}L$ (SEQ ID NO: 4)
(IV)

IKLSGGVQAKAGVINMDKSESM (SEQ ID NO: 5)
(V)

IKLSGGVQAKAGVINMFKSESY (SEQ ID NO: 6)
(VI)

IKLSGGVQAKAGVINMFKSESYK (SEQ ID NO: 7)
(VII)

GVQAKAGVINMFKSESY (SEQ ID NO: 8)
(VIII)

GVRAKAGVRNMFKSESY (SEQ ID NO: 9)
(IX)

GVRAKAGVRN(Nle)FKSESY (SEQ ID NO: 10)
(X)

YKSLRRKAPRWDAPLRDPALRQLL (SEQ ID NO: 11)
(XI)

YKSLRRKAPRWDAYLRDPALRQLL (SEQ ID NO: 12)
(XII)
or

YKSLRRKAPRWDAYLRDPALRPLL (SEQ ID NO: 13)
(XIII).

For example, the peptide compound is a peptide compound that consists essentially of:

$X_1X_2X_3X_4X_5GVX_6AKAGVX_7NX_8FKSESY$ (SEQ ID NO: 1)
(I)

$(X_9)_nGVX_{10}AKAGVX_{11}NX_{12}FKSESY$ (SEQ ID NO: 2)
(II)

$YKX_{13}LRRX_{14}APRWDX_{15}PLRDPALRX_{16}X_{17}L$ (SEQ ID NO: 3)
(III)

$YKX_{18}LRR(X_{19})_nPLRDPALRX_{20}X_{21}L$ (SEQ ID NO: 4)
(IV)

IKLSGGVQAKAGVINMDKSESM (SEQ ID NO: 5)
(V)

```
                               (SEQ ID NO: 6)
IKLSGGVQAKAGVINMFKSESY
(VI)

(SEQ ID NO: 7)
IKLSGGVQAKAGVINMFKSESYK
(VII)

(SEQ ID NO: 8)
GVQAKAGVINMFKSESY
(VIII)

(SEQ ID NO: 9)
GVRAKAGVRNMFKSESY
(IX)

(SEQ ID NO: 10)
GVRAKAGVRN(Nle)FKSESY
(X)

(SEQ ID NO: 11)
YKSLRRKAPRWDAPLRDPALRQLL
(XI)

(SEQ ID NO: 12)
YKSLRRKAPRWDAYLRDPALRQLL
(XII)
or (SEQ ID NO: 13)
YKSLRRKAPRWDAYLRDPALRPLL
(XIII).
```

For example, the peptide compound is a peptide compound that consists of:

```
                               (SEQ ID NO: 1)
X1X2X3X4X5GVX6AKAGVX7NX8FKSESY
(I)

(SEQ ID NO: 2)
(X9)nGVX10AKAGVX11NX12FKSESY
(II)

(SEQ ID NO: 3)
YKX13LRRX14APRWDX15PLRDPALRX16X17L
(III)

(SEQ ID NO: 4)
YKX18LRR(X19)nPLRDPALRX20X21L
(IV)

(SEQ ID NO: 5)
IKLSGGVQAKAGVINMDKSESM
(V)

(SEQ ID NO: 6)
IKLSGGVQAKAGVINMFKSESY
(VI)

(SEQ ID NO: 7)
IKLSGGVQAKAGVINMFKSESYK
(VII)

(SEQ ID NO: 8)
GVQAKAGVINMFKSESY
(VIII)

(SEQ ID NO: 9)
GVRAKAGVRNMFKSESY
(IX)

(SEQ ID NO: 10)
GVRAKAGVRN(Nle)FKSESY
(X)
```

According to another aspect, there is provided a peptide compound that comprises a compound chosen from compounds of formula (I), formula (II), formula (III), formula (IV), formula (V), formula (VI), formula (VII), formula (VIII), formula (IX), formula (X), formula (XI), formula (XII) and formula (XIII):

```
                               (SEQ ID NO: 1)
X1X2X3X4X5GVX6AKAGVX7NX8FKSESY
(I)

(SEQ ID NO: 2)
(X9)nGVX10AKAGVX11NX12FKSESY
(II)

(SEQ ID NO: 3)
YKX13LRRX14APRWDX15PLRDPALRX16X17L
(III)

(SEQ ID NO: 4)
YKX18LRR(X19)nPLRDPALRX20X21L
(IV)

(SEQ ID NO: 5)
IKLSGGVQAKAGVINMDKSESM
(V)

(SEQ ID NO: 6)
IKLSGGVQAKAGVINMFKSESY
(VI)

(SEQ ID NO: 7)
IKLSGGVQAKAGVINMFKSESYK
(VII)

(SEQ ID NO: 8)
GVQAKAGVINMFKSESY
(VIII)

(SEQ ID NO: 9)
GVRAKAGVRNMFKSESY
(IX)

(SEQ ID NO: 10)
GVRAKAGVRN(Nle)FKSESY
(X)

(SEQ ID NO: 11)
YKSLRRKAPRWDAPLRDPALRQLL
(XI)

(SEQ ID NO: 12)
YKSLRRKAPRWDAYLRDPALRQLL
(XII)

(SEQ ID NO: 13)
YKSLRRKAPRWDAYLRDPALRPLL
(XIII)
``` wherein $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{18}$ and $X_{19}$ are independently chosen from any amino acid;

$X_{16}$, $X_{17}$, $X_{20}$ and $X_{21}$ are independently chosen from Q, P, Y, I and L;

n is 0, 1, 2, 3, 4 or 5, when $X_9$ is present more than once, each of said $X_9$ is independently chosen from any amino acid;

when $X_{19}$ is present more than once, each of said $X_9$ is independently chosen from any amino acid and wherein at least one protecting group and/or at least one labelling agent is optionally connected to said peptide at an N- and/or C-terminal end.

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound chosen from peptide compounds of formula (I), formula (II), formula (III), formula (IV), formula (V), formula (VI), formula (VII), formula (VIII), formula (IX), formula (X), formula (XI), formula (XII) and formula (XIII).

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound represented by formula (I) or SEQ ID NO: 1.

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound represented by formula (II) or SEQ ID NO: 2.

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound represented by formula (III) or SEQ ID NO: 3.

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound represented by formula (IV) or SEQ ID NO: 4.

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound represented by formula (V) or SEQ ID NO: 5.

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound represented by formula (VI) or SEQ ID NO: 6.

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound represented by formula (VII) or SEQ ID NO: 7.

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound represented by formula (VIII) or SEQ ID NO: 8.

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound represented by formula (IX) or SEQ ID NO: 9.

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound represented by formula (X) or SEQ ID NO: 10.

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound represented by formula (XI) or SEQ ID NO: 11.

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound represented by formula (XII) or SEQ ID NO: 12.

For example, the peptide compound has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to a peptide compound represented by formula (XIII) or SEQ ID NO: 13.

In one embodiment, n is 0. In one embodiment, n is 1. In one embodiment, n is 2. In one embodiment, n is 3. In one embodiment, n is 4. In one embodiment, n is 5.

In an embodiment, the peptide compound is represented by formula (I) or formula (II).

In one embodiment, the peptide compound is represented by formula (I) or SEQ ID NO: 1.

In one embodiment, the peptide compound is represented by formula (II) or SEQ ID NO: 2.

In an embodiment, the peptide compound is represented by formula (V), formula (VI), formula (VII), formula (VIII), formula (IX) or formula (X).

In one embodiment, the peptide compound is represented by formula (V).

In one embodiment, the peptide compound is represented by formula (VI).

In one embodiment, the peptide compound is represented by formula (VII).

In one embodiment, the peptide compound is represented by formula (VIII).

In one embodiment, the peptide compound is represented by formula (IX).

In one embodiment, the peptide compound is represented by formula (X).

In one embodiment, the peptide compound is represented by formula (III) or formula (IV).

In one embodiment, the peptide compound is represented by formula (III).

In one embodiment, the peptide compound is represented by formula (IV).

In one embodiment, the peptide compound is represented by formula (XI), formula (XII) or formula (XIII).

In one embodiment, the peptide compound is represented by formula (XI).

In one embodiment, the peptide compound is represented by formula (XII).

In one embodiment, the peptide compound is represented by formula (XIII).

In one embodiment, the peptide is represented by the amino acid sequence of SEQ ID NO: 1. In one embodiment, the peptide is represented by the amino acid sequence of SEQ ID NO: 2. In one embodiment, the peptide is represented by the amino acid sequence of SEQ ID NO: 3. In one embodiment, the peptide is represented by the amino acid sequence of SEQ ID NO: 4. In one embodiment, the peptide is represented by the amino acid sequence of SEQ ID NO: 5. In one embodiment, the peptide is represented by the amino acid sequence of SEQ ID NO: 6. In one embodiment, the peptide is represented by the amino acid sequence of SEQ ID NO: 7. In one embodiment, the peptide is represented by the amino acid sequence of SEQ ID NO: 8. In one embodiment, the peptide is represented by the amino acid sequence of SEQ ID NO: 9. In one embodiment, the peptide is represented by the amino acid sequence of SEQ ID NO: 10. In one embodiment, the peptide is represented by the amino acid sequence of SEQ ID NO: 11. In one embodiment, the peptide is represented by the amino acid sequence of SEQ ID NO: 12. In one embodiment, the peptide is represented by the amino acid sequence of SEQ ID NO: 13.

In one embodiment, at least one protecting group is connected to said peptide at an N- and/or C-terminal end.

In one embodiment, a succinyl group is connected to the peptide compound. For example, the peptide compound has the sequence of Succinyl-IKLSGGVQAKAGVINMFKSESY, corresponding to SEQ ID NO: 6 and having a succinyl group attached thereto at the N-terminal end.

In one embodiment, an acetyl group is connected to the peptide compound. For example, the peptide compound has the sequence of Acetyl-GVRAKAGVRNMFKSESY (SEQ ID NO: 14). For example, the peptide compound has the sequence of Acetyl-GVRAKAGVRN(Nle)FKSESY (SEQ ID NO: 15). For example, the peptide compound has the sequence of Acetyl-YKSLRRKAPRWDAPLRDPALRQLL (SEQ ID NO: 16). For example, the peptide compound has the sequence of Acetyl-YKSLRRKAPRWDAYLRDPALRQLL (SEQ ID NO: 17). For example, the peptide compound has the sequence of Acetyl-YKSLRRKAPRWDAYLRDPALRPLL (SEQ ID NO: 18).

In one embodiment, at least one labelling agent is connected to said peptide at an N- and/or C-terminal end.

The person skilled in the art will understand that commonly used labelling agents can be used. For example, the labelling agent is a vitamin. For example, the labelling agent is biotin.

In one embodiment, the peptide compound is biotinylated. For example, the peptide compound has the sequence of IKLSGGVQAKAGVINMFKSESYK(Biotin), corresponding to SEQ ID NO: 7 and having a biotin molecule attached thereto at the C-terminal end.

In one embodiment, $X_{16}$ is independently chosen from Q, P, Y, I and L.

For example, $X_{16}$ is Q.
For example, $X_{16}$ is P.
For example, $X_{16}$ is Y.
For example, $X_{16}$ is I.

In one embodiment, $X_{17}$ is independently chosen from Q, P, Y, I and L.

For example, $X_{17}$ is Q.
For example, $X_{17}$ is P.
For example, $X_{17}$ is Y.
For example, $X_{17}$ is I.

In one embodiment, $X_{20}$ is independently chosen from Q, P, Y, I and L.

For example, $X_{20}$ is Q.
For example, $X_{20}$ is P.
For example, $X_{20}$ is Y.
For example, $X_{20}$ is I.

In one embodiment, $X_{21}$ is independently chosen from Q, P, Y, I and L.

For example, $X_{21}$ is Q.
For example, $X_{21}$ is P.
For example, $X_{21}$ is Y.
For example, $X_{21}$ is I.

In one embodiment, the peptide compound is chosen from:

$X_1X_2X_3X_4X_5GVX_6AKAGVX_7NX_8FKSESY$; (SEQ ID NO: 1)

$(X_9)_nGVX_{10}AKAGVX_{11}NX_{12}FKSESY$; (SEQ ID NO: 2)

$YKX_{13}LRRX_{14}APRWDX_{15}PLRDPALRX_{16}X_{17}L$; (SEQ ID NO: 3)

$YKX_{18}LRR(X_{19})_nPLRDPALRX_{20}X_{21}L$; (SEQ ID NO: 4)

IKLSGGVQAKAGVINMDKSESM; (SEQ ID NO: 5)

Succinyl-IKLSGGVQAKAGVINMFKSESY
(that comprises SEQ ID NO: 6 wherein a succinyl group is attached thereto at the N-terminal end);

IKLSGGVQAKAGVINMFKSESYK(Biotin)
(that comprises SEQ ID NO: 7 wherein a biotin molecule is attahed thereto at the C-terminal end);

GVQAKAGVINMFKSESY; (SEQ ID NO: 8)

Acetyl-GVRAKAGVRNMFKSESY; (SEQ ID NO: 14)

Acetyl-GVRAKAGVRN(Nle)FKSESY; (SEQ ID NO: 15)

Acetyl-YKSLRRKAPRWDAPLRDPALRQLL; (SEQ ID NO: 16)

Acetyl-YKSLRRKAPRWDAYLRDPALRQLL; (SEQ ID NO: 17)
and

Acetyl-YKSLRRKAPRWDAYLRDPALRPLL. (SEQ ID NO: 18)

In one embodiment, the peptide compounds can be modified at the C- and/or N-terminal by the addition of one or more amino acid residue in order to obtain or increase preferential binding sites at the peptide terminal end. For example, the amino acid can be cysteine. For example, the amino acid can be lysine.

The peptide compounds described herein can be connected, linked, mixed or conjugated to small molecules, peptides, anticancer peptides, proteins, oligonucleotides, diagnostic agents, imaging or radionuclide agents, large molecules such as monoclonal antibodies, therapeutic agents such as anticancer agents and phytochemicals or to drug delivery systems including nanoparticles, liposomes, graphene particles loaded with a therapeutic agent, imaging agent, gene, siRNA. The resulting conjugate compounds can be used as mono- or combined therapies for example for treating cancer.

Accordingly, a second aspect disclosed herein is a conjugate compound having the formula of A-(B)$_n$,
wherein
n is 1, 2, 3 or 4;
A is a peptide compound as defined in any one of claims 1 to 14, wherein said peptide is optionally protected by a protecting group; and
B is at least one therapeutic agent, wherein B is connected to A.

A third aspect disclosed herein is a conjugate compound having the formula of A-(B)$_n$,
wherein
n is 1, 2, 3 or 4;
A is a peptide compound as defined herein; and
B is at least one therapeutic agent, wherein B is connected to A at a free amine of a lysine residue of said peptide compound, optionally via a linker, or at an N-terminal position of said peptide compound, optionally via a linker.

In an embodiment, B is connected to A via a linker, optionally a cleavable linker.

Anticancer agents that can be used include for example alkylating agents, for example nitrogen mustards (Melphalan, Cyclophosphamide, Ifosfamide), Nitrosoureas, Alkylsulfonates, Ethyleneimines, Triazene, Methyl Hydrazines and Platinum Coordination complexes such as Cisplatin, Carboplatin, Oxaliplatin.

For example, antimetabolites such as folate antagonists (such as methotrexate), purine antagonists and pyrimidine antagonists (such as 5-Fluorouracil and cytabarine) can be used as anticancer agents.

For example, natural products can be used as anticancer agents. Such natural products include plant products, for example, vinca alkaloids (such as vincristine, vinblastine), taxanes (such as paclitaxel, docetaxel and cabazitaxel), toxins, epipodopyllotoxins (such as etoposide) and camtothecins (such as irinotecan) and microorganism products for example antibiotics (such as doxorubicin and bleomycin, and enzymes such as L-asparaginase.

Other anticancer agents that can be used include for example Maytansine, Auristatin, Dolastin, Chalicheamicin, Emtansine, Amanitin, Pyrrolobenzodiazepines, Tubulysins, Hydroxyurea, Imatinib Mesylate, Rituximab, Epirubicin, Bortezomib, Zoledronic Acid, Geftinib, Leucovorin, Pamidronate and Gemcitabine.

For example, hormones and antagonists such as Corticosteroids (Prednisone, Dexamethasone), Estrogens (Ethinyloestradiol), Antiestrogens (Tamoxifen), Progesteron derivatives (Megestrol Acetate), Androgen (Testosterone propionate), Antiandrogen (Flutamide, Bicalutamide), Aromatase inhibitors (Letrozole, Anastrazole), 5-alpha reductase inhibitor (Finasteride), GnRH Analogues (Leuprolide, Buserelin) and Growth Hormone, glucagon and insulin inhibitor (Octreotide) can be used as anticancer agents.

For example, the compounds disclosed herein may be connected to anticancer agents used for targeted cancer therapy including for example tyrosine kinase inhibitors (TKI) (for example imatinib mesylate, gefitinib, erlotinib, sorafenib, sunitinib, dasatinib, lapatinib, nilotinib and bortezomib), antibodies, monoclonal antibodies (mABs) (for example rituximab, trastuzumab, alemtuzumab, cetuximab, bevacizumab and ipilimumab), mechanistic target of rapamycin (mTOR) inhibitors and antibody-drug conjugates (for example trastuzumab emtansine (T-M D1).

For example, the compounds disclosed herein may be connected to peptides used for peptide-based cancer therapy such as for example buserelin, gonadorelin, goserelin, histrelin, leuprolide, nafarelin, triptorelin, abarelix, cetrorelix, degarelix and ganirelix.

In an embodiment, the therapeutic agent is an anticancer agent.

For example, the anticancer agent is docetaxel, cabazitaxel, paclitaxel, doxorubicin and daunomycin.

In an embodiment, the anticancer agent is docetaxel.

In an embodiment, the conjugate compound is chosen from compounds of formula (XIV), formula (XV), formula (XVI), formula (XVII) and formula (XVIII):

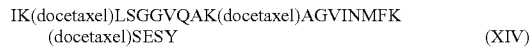

IK(docetaxel)LSGGVQAK(docetaxel)AGVINMFK(docetaxel)SESY  (XIV)

that comprises the peptide compound having SEQ ID NO: 6 wherein each lysine residue has a docetaxel molecule connected thereto;

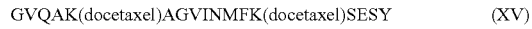

GVQAK(docetaxel)AGVINMFK(docetaxel)SESY  (XV)

that comprises the peptide compound having SEQ ID NO: 8 wherein each lysine residue has a docetaxel molecule connected thereto;

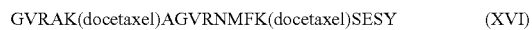

GVRAK(docetaxel)AGVRNMFK(docetaxel)SESY  (XVI)

that comprises the peptide compound having SEQ ID NO: 9 wherein each lysine residue has a docetaxel molecule connected thereto;

GVRAK(docetaxel)AGVRN(Nle)FK(docetaxel)S-
    ESY  (XVII)

that comprises the peptide compound having SEQ ID NO: 10 wherein each lysine residue has a docetaxel molecule connected thereto; and

YK(docetaxel)SLRRK(docetaxel)APRWDAPLRD-
    PALRQL  (XVIII)

that comprises the peptide compound having SEQ ID NO: 11 wherein each lysine residue has a docetaxel molecule connected thereto.

In an embodiment, the conjugate compound is represented by formula (XIV).
In an embodiment, the conjugate compound is represented by formula (XV).
In an embodiment, the conjugate compound is represented by formula (XVI).
In an embodiment, the conjugate compound is represented by formula (XVII).
In an embodiment, the conjugate compound is represented by formula (XVIII).
In another embodiment, the conjugate compound is chosen from:

Succinyl-IK(docetaxel)LSGGVQAK(docetaxel)
    AGVINMFK(docetaxel)SESY  (XIX)

that comprises the peptide compound having SEQ ID NO: 6 wherein each lysine residue has a docetaxel molecule connected thereto; and wherein a succinyl group is attached at the N-terminal end;

Acetyl-GVRAK(docetaxel)AGVRNMFK(docetaxel)SESY (XX)

that comprises the peptide compound having SEQ ID NO: 14 wherein each lysine residue has a docetaxel molecule connected thereto;

Acetyl-GVRAK(docetaxel)AGVRN(Nle)FK(docetaxel)SESY (XXI)

that comprises the peptide compound having SEQ ID NO: 15 wherein each lysine residue has a docetaxel molecule connected thereto; and Acetyl-YK(docetaxel)SLRRK(docetaxel)APRWDAPLRDPALRQLL (XXII)

that comprises the peptide compound having SEQ ID NO: 16 wherein each lysine residue has a docetaxel molecule connected thereto.

In an embodiment, the conjugate compound is represented by formula (XIX).

In an embodiment, the conjugate compound is represented by formula (XX).

In an embodiment, the conjugate compound is represented by formula (XXI).

In an embodiment, the conjugate compound is represented by formula (XXII).

In yet another embodiment, the anticancer agent is doxorubicin.

In an embodiment, the conjugate compound is chosen from compounds of formula (XXIII), formula (XXIV) and formula (XXV):

GVQAK(doxorubicin)AGVINMFK(doxorubicin)SESY (XXIII)

that comprises the peptide compound having SEQ ID NO: 8 wherein each lysine residue has a doxorubicin molecule connected thereto;

GVRAK(doxorubicin)AGVRN(Nle)FK(doxorubicin)SESY (XXIV)

that comprises the peptide compound having SEQ ID NO: 10 wherein each lysine residue has a doxorubicin molecule connected thereto; and YK(doxorubicin)SLRRK(doxorubicin)APRWDAPLRDPALRQLL (XXV)

that comprises the peptide compound having SEQ ID NO: 11 wherein each lysine residue has a doxorubicin molecule connected thereto.

In an embodiment, the conjugate compound is represented by formula (XXIII).

In an embodiment, the conjugate compound is represented by formula (XXIV).

In an embodiment, the conjugate compound is represented by formula (XXV).

For example, the conjugate compound can be chosen from

Acetyl-GVRAK(doxorubicin)AGVRN(Nle)FK(doxorubicin)SESY (XXVI)

that comprises the peptide compound having SEQ ID NO: 15 wherein each lysine residue has a doxorubicin molecule connected thereto; and Acetyl-YK(doxorubicin)SLRRK(doxorubicin)APRWDAPLRDPALRQLL (XXVII)

that comprises the peptide compound having SEQ ID NO: 16 wherein each lysine residue has a doxorubicin molecule connected thereto.

In an embodiment, the conjugate compound is represented by formula (XXVI).

In an embodiment, the conjugate compound is represented by formula (XXVII).

In an embodiment, the anticancer agent is cabazitaxel.

In an embodiment, the conjugate compound is chosen from compounds of formula (XXVIII), formula (XXIX) and (XXX):

GVRAK(cabazitaxel)AGVRNMFK(cabazitaxel)SESY (XXVIII)

that comprises the peptide compound having SEQ ID NO: 9 wherein each lysine residue has a cabazitaxel molecule connected thereto;

GVRAK(cabazitaxel)AGVRN(Nle)FK(cabazitaxel)SESY (XXIX)

that comprises the peptide compound having SEQ ID NO: 10 wherein each lysine residue has a cabazitaxel molecule connected thereto;

andYK(cabazitaxel)SLRRK(cabazitaxel)APRWDAPLRDPALRQL (XXX)

that comprises the peptide compound having SEQ ID NO: 9 wherein each lysine residue has a cabazitaxel molecule connected thereto. In an embodiment, the conjugate compound is represented by formula (XXVIII).

In an embodiment, the conjugate compound is represented by formula (XXIX).

In an embodiment, the conjugate compound is represented by formula (XXX).

For example, the conjugate compound can be chosen from compounds of formula (XXXI), formula (XXXII) and (XXXIII):

Acetyl-GVRAK(cabazitaxel)AGVRNMFK(cabazitaxel)SESY (XXXI)

that comprises the peptide compound having SEQ ID NO: 14 wherein each lysine residue has a cabazitaxel molecule connected thereto;

Acetyl-GVRAK(cabazitaxel)AGVRN(Nle)FK(cabazitaxel)SESY (XXXII)

that comprises the peptide compound having SEQ ID NO: 15 wherein each lysine residue has a cabazitaxel molecule connected thereto; and Acetyl-YK(cabazitaxel)SLRRK(cabazitaxel)APRWDAPLRDPALRQLL (XXXIII)

that comprises the peptide compound having SEQ ID NO: 16 wherein each lysine residue has a cabazitaxel molecule connected thereto.

In an embodiment, the conjugate compound is represented by formula (XXXI).

In an embodiment, the conjugate compound is represented by formula (XXXII).

In an embodiment, the conjugate compound is represented by formula (XXXIII).

Other therapeutic agents that can be used include phytochemicals.

In an embodiment, the phytochemical is curcumin.

In an embodiment, the conjugate compound is represented by formula (XXXIV):

GVRAK(curcumin)AGVRN(Nle)FK(curcumin)SESY (XXXIV)

that comprises the peptide compound having SEQ ID NO: 10 wherein each lysine residue has a curcumin molecule connected thereto.

For example, the conjugate compound can is represented by formula (XXXV):

Acetyl-GVRAK(curcumin)AGVRN(Nle)FK(curcumin)SESY (XXXV)

that comprises the peptide compound having SEQ ID NO: 15 wherein each lysine residue has a curcumin molecule connected thereto.

In an embodiment, B, the at least one therapeutic agent, is connected to A, the peptide compound, at said free amine of said lysine residue of said peptide compound, via a linker.

In an embodiment, B, the at least one therapeutic agent, is connected to A, the peptide compound, at said N-terminal position of said peptide compound, via a linker.

In an embodiment, the linker is chosen from succinic acid and dimethyl glutaric acid linker.

For example, the linker is a cleavable linker.

For example, the linker is a non-cleavable linker.

As shown in Example 2, the conjugate compound can comprise a cleavable linker connected the at least one therapeutic agent to the peptide compound. For example, the at least one therapeutic agent can be released from the peptide compound by the action of esterases on the ester bond.

Figure 4:
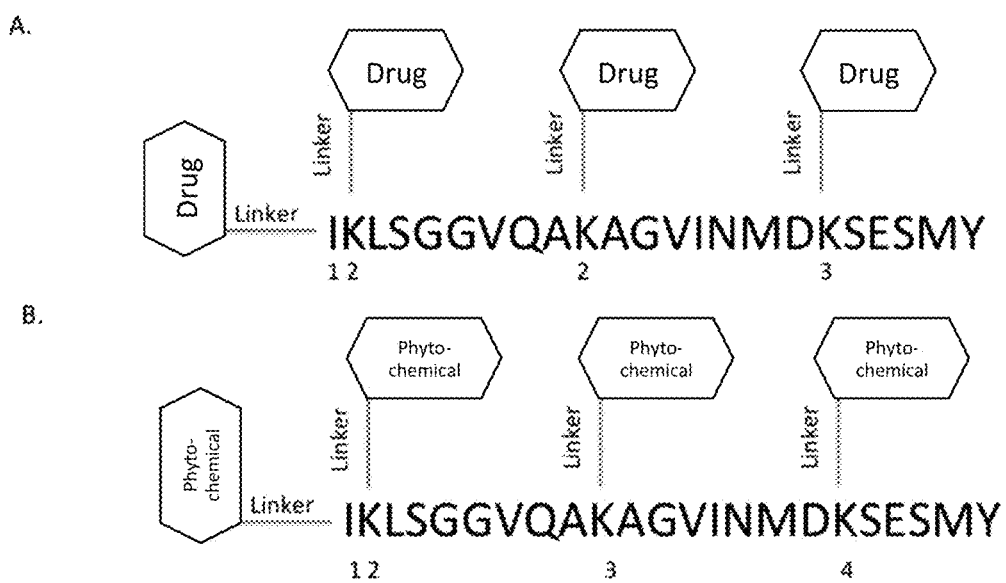
FIG. 4 is a schematic representation of (A) an anticancer drug conjugated to the Katana peptide and (B) a phytochemical conjugated to the Katana peptide.

For example, as shown in Example 2 and in FIG. 4, a therapeutic agent can be conjugated to the peptide compound on free amines available on the peptide, at the lysine or amino-terminal, by forming a bond such as a peptide bond.

In an embodiment, the conjugate compound comprises 1 molecule of the therapeutic agent connected to the peptide compound.

In an embodiment, the conjugate compound comprises 2 molecules of the therapeutic agent connected to the peptide compound.

In an embodiment, the conjugate compound comprises 3 molecules of the therapeutic agent connected to the peptide compound.

In an embodiment, the conjugate compound comprises 4 molecules of the therapeutic agent connected to the peptide compound.

In one embodiment, the conjugation of a therapeutic agent to a peptide compound, thereby forming a conjugate compound, does not alter the potency of the therapeutic agent.

For example, as shown in Table 4, $IC_{50}$ values for the Docetaxel-Katana peptide conjugate is similar to $IC_{50}$ values for unconjugated docetaxel in ovary, breast and skin cancer cells.

Conjugate compounds herein disclosed can also be used to transport therapeutic agents into the cell as they are not a substrate of efflux pumps such as the P-glycoprotein membrane transporter pump which pumps out other therapeutic agents from multi resistant drug cells.

Figure 6:
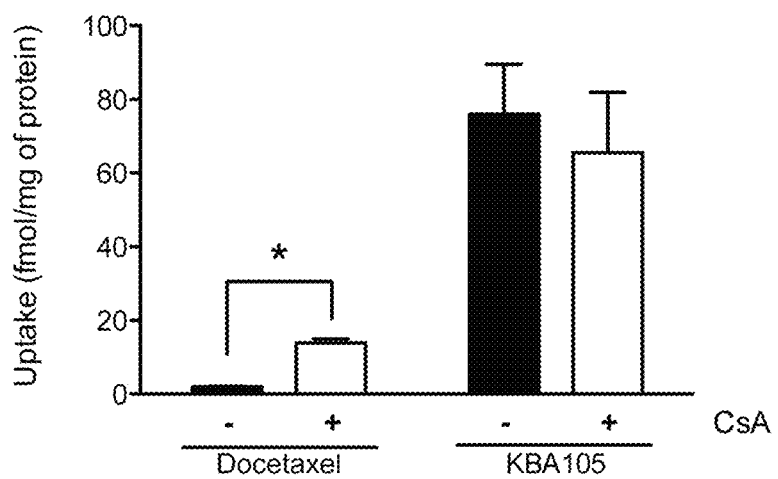
FIG. 6 shows the uptake of unconjugated drugs and of Katana-peptide drug conjugates in MDCK cells transfected with MDR1. 6A. MDCK-MDR1 cells were incubated with 50 nM of either [$^3$H]-Docetaxel or [$^{125}$I]-Katana peptide-Docetaxel conjugate (KBA105) for 1 hr at 37° C. in the presence or absence of the P-gp (MDR1) inhibitor Cyclosporin A (CsA) (10 µM). 6B. MDCK-MDR1 cells were incubated with 50 nM of either [$^{14}$C]-Doxorubicin or [$^{125}$I]-Katana peptide-Doxorubicin conjugate (KBB106) for 1 hr at 37° C. in the presence or absence of CsA (10 µM). After the incubation, cells were washed and radioactivity accumulated in cells was quantified. The results were expressed in terms of uptake fmol/mg of protein.
Figure 6:
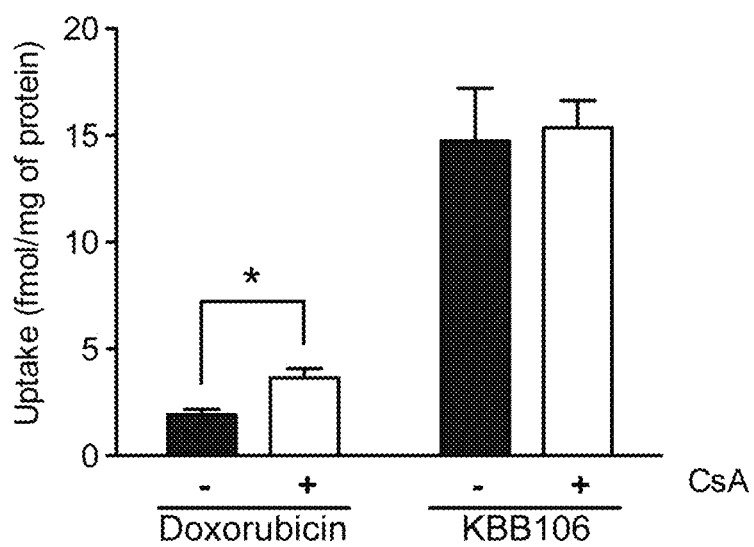

For example, as shown in FIG. 6, the docetaxel-conjugate uptake in MDCK-MDR cells, kidney epithelial cells transfected with human multidrug resistant gene MDR1, is faster and accumulates at higher concentrations compared to unconjugated docetaxel.

In a further aspect, there is provided a process for preparing the conjugate compound herein disclosed, the process comprising:
  reacting a linker together with said therapeutic agent so as to obtain an intermediate;
  optionally purifying said intermediate;
  reacting said intermediate together with said peptide compound so as to obtain said conjugate compound; and
  optionally purifying said conjugate compound;
wherein the therapeutic agent is connected to the peptide compound at a free amine of a lysine residue or an N-terminal; and wherein the peptide compound comprises 1, 2, 3 or 4 therapeutic agent molecules connected thereto.

For example, the peptide compound comprises 1 therapeutic agent molecule connected thereto. For example, the peptide compound comprises 2 therapeutic agent molecules connected thereto. For example, the peptide compound comprises 3 therapeutic agent molecules connected thereto. For example, the peptide compound comprises 4 therapeutic agent molecules connected thereto.

For example, the linker is succinic acid.

For example, the linker is a dimethyl glutaric acid linker.

In an embodiment, the peptide compound is protected at said N-terminal prior to reacting with said intermediate.

Examples of the synthesis of conjugate compounds are shown in Examples 11 and 12.

For example, a protecting group such as FMOC can be added as a protecting group to a free amine on the therapeutic agent prior to incorporation with a linker. After its synthesis, the conjugate compound can undergo deprotection from the protecting group. For example, the conjugate compound comprising the protecting agent FMOC can be deprotected using piperidin. The person skilled in the art would readily understand that other known chemical reagents may be used for deprotection of conjugate compounds.

For example, the N-terminal of the therapeutic agent and/or the peptide compound can be capped by its acetylation, thereby providing a non-reversible protecting group at the N-terminal.

In an embodiment, the intermediate is activated prior to reacting with said peptide compound.

For example, the intermediate is activated prior to reacting with said compound with a coupling agent, optionally chosen from N,N,N',N'-Tetramethyl-O-(benzotriazol-1-yl)uronium tetrafluoroborate (TBTU), (2-(1H-benzotriazol-1-yl)-1,1,3,3-tetramethyluronium hexafluorophosphate) (HBTU), and (1-[Bis(dimethylamino)methylene]-1H-1,2,3-triazolo[4,5-b]pyridinium 3-oxid hexafluorophosphate) (HATU).

For example, the intermediate comprising a therapeutic agent connected to a linker can be activated with TBTU, a peptide coupling reagent, prior to conjugation with the peptide compound.

In one embodiment, the conjugate compound is purified following its synthesis.

Compounds disclosed herein may also be used in the context of fusion proteins. For example, a fusion protein can be engineered by fusing a compound herein disclosed, for example a peptide compound, to one or more proteins, or parts thereof such as functional domains. Fusion proteins can be engineered for example by recombinant DNA technology and expressed using a protein expression system such as a bacterial or mammalian protein expression system. In some embodiments, peptide linkers are added between proteins. In other embodiment, the fusion proteins do not comprise linkers connecting the proteins.

Commonly used protein expression systems include those derived from bacteria, yeast, baculovirus/insect, plants and mammalian cells and more recently filamentous fungi such as the *Myceliophthora thermophile*.

In addition, in some embodiments, the compound herein described can be associated, linked, or connected to one or more other compounds to form a multimer such as a dimer, a trimer or a tetramer, as well as branched peptides. Such compounds can be connected together, for example via a covalent bond, an atom or a linker. For example, the multimer comprises more than one peptide compound and/or more than one conjugate compound. Methods for making multimeric (e.g. dimeric, trimeric) forms of compounds are described in U.S. Pat. No. 9,161,988 which is incorporated herein by reference in its entirety.

Another aspect of the disclosure includes a method of treating a disease comprising administrating a therapeutically effective amount of at least one compound herein disclosed to a subject in need thereof.

For example, there is provided herein a method of treating a cancer involving sortilin expression comprising contacting at least one cancer cell expressing sortilin with at least one compound herein disclosed.

For example, there is provided herein a method of treating a disease involving sortilin expression comprising administering to a subject in need thereof a therapeutically effective amount of at least one compound herein disclosed.

For example, there is provided herein a method of treating a cancer involving expression of at least one receptor chosen from vacuolar protein sorting 10 (Vps10) family of receptors comprising contacting at least one cancer cell expressing the at least one receptor with at least one compound herein disclosed.

For example, there is provided herein a method of treating a disease involving expression of at least one receptor chosen from vacuolar protein sorting 10 (Vps10) family of receptors comprising administering to a subject in need thereof a therapeutically effective amount of at least one compound herein disclosed.

For example, the at least one receptor is chosen from sortilin, SorL1, SorCS1, SorCS2, and SorCS3.

For example, the at least one receptor plays pleiotropic functions in protein trafficking and intracellular and intercellular signaling in neuronal and non-neuronal cells.

For example, in a method of a medical treatment involving a therapeutic agent, the improvement wherein the method comprises increasing tolerability of the therapeutic agent administered to a subject in need thereof by administering the therapeutic agent with at least one compound herein disclosed.

For example, in a method of a medical treatment involving a therapeutic agent, the improvement wherein the method comprises increasing tolerability of the therapeutic agent administered to a subject in need thereof by administering the therapeutic agent conjugated to at least one compound herein disclosed.

For example, there is provided herein a method of increasing tolerability of a therapeutic agent, comprising:
  obtaining the conjugate compound herein disclosed, wherein the conjugate compound comprises the therapeutic agent, and
  administering a therapeutically effective amount of the conjugate compound to a subject in need thereof.

For example, there is provided herein a method of increasing tolerability of a therapeutic agent, comprising:
  conjugating the therapeutic agent with the peptide compound herein disclosed to obtain a conjugate compound, and
  administering a therapeutically effective amount of the conjugate compound to a subject in need thereof.

For example, there is provided herein a method of increasing anti-proliferation activity of a therapeutic agent, comprising:
  obtaining the conjugate compound herein disclosed, wherein the conjugate compound comprises the therapeutic agent, and
  administering a therapeutically effective amount of the conjugate compound to a subject in need thereof.

For example, there is provided herein a method of increasing anti-proliferation activity of a therapeutic agent, comprising:
  conjugating the therapeutic agent with the peptide compound herein disclosed to obtain a conjugate compound, and
  administering a therapeutically effective amount of the conjugate compound to a subject in need thereof.

For example, the anti-proliferation activity is increased at least 10-fold, at least 20-fold, at least 30-fold, at least 40-fold, at least 50-fold, at least 60-fold, at least 70-fold, at least 80-fold, at least 90-fold or at least 100-fold compared to an unconjugated therapeutic agent.

For example, the cancer is ovarian cancer, brain cancer, breast cancer, melanoma, colorectal cancer, glioblastoma, liver cancer, lung cancer, prostate cancer, cervical cancer, head cancer, gastric cancer, kidney cancer, endometrial cancer, testis cancer, urothelial cancer, acute lymphoblastic leukemia, acute myeloid leukemia, Hodgkin lymphoma, neuroblastoma, non-Hodgkin lymphoma, soft tissue cancer, bone sarcoma, thyroid cancer, transitional cell bladder cancer, Wilm's tumour, glioma, pancreatic cancer or spleen cancer.

For example, the cancer is a cancer involving sortilin expression.

For example, there is provided herein a method of increasing cellular internalization of a therapeutic agent, comprising:
  obtaining the conjugate compound herein disclosed, wherein the conjugate compound comprises the therapeutic agent, and
  administering a therapeutically effective amount of the conjugate compound to a subject in need thereof.

For example, there is provided herein a method of increasing cellular internalization of a therapeutic agent, comprising:
  conjugating the therapeutic agent with the peptide compound herein disclosed to obtain a conjugate compound, and
  administering a therapeutically effective amount of the conjugate compound to a subject in need thereof.

For example, there is provided herein a method of increasing cellular internalization of a therapeutic agent, comprising:
  conjugating the therapeutic agent with the peptide compound herein disclosed to obtain a conjugate compound, and
  contacting at least one cell with the conjugate compound.

Another aspect includes a use of at least one compound herein disclosed for treating a disease.

A further aspect includes one or more compound herein disclosed for treating a disease.

In one embodiment, the disease is a cancer.

Another aspect provided is a method of treating a cancer comprising administrating a therapeutically effective amount of at least one compound herein disclosed to a subject in need thereof.

Another aspect includes a use of at least one compound herein disclosed for treating a cancer.

Yet another aspect includes one or more compound herein disclosed for treating a cancer.

In one embodiment, the compound is a conjugate compound herein disclosed.

Cancers that can be treated using the compounds herein disclosed include, but are not limited to, hematological cancers and solid cancers, including for example tumours of the ovary, endometrial, skin, brain, spine, breast, colon, small intestine, liver, lung, prostate, head, neck, stomach, bone, thyroid, bladder, kidney, pancreas and spleen.

In one embodiment, the cancer is ovarian cancer.

In one embodiment, the cancer is breast cancer.

In one embodiment, the cancer is brain cancer.

In one embodiment, the cancer is lung cancer.

In one embodiment, the cancer is skin cancer.

In an embodiment, the cancer is a hematological cancer.

In an embodiment, the hematological cancer is a leukemia such as acute myeloid leukemia (AML), acute lymphocytic leukemia (ALL), chronic lymphocytic leukemia (CLL) and chronic myelogenous leukemia (CML). In another embodiment, the hematological cancer is a myeloma. In an embodiment, the hematological cancer is a lymphoma such as non-Hodgkin lymphoma and Hodgkin lymphoma.

In an embodiment, the cancer is a brain cancer. In an embodiment, the brain cancer is a glioblastoma.

In an embodiment, the cancer is liver cancer. In an embodiment, the liver cancer is hepatocellular adenocarcinoma.

In an embodiment, the cancer is lung cancer. In an embodiment, the lung cancer non-small cell lung cancer.

In an embodiment, the cancer is kidney cancer. In an embodiment, the kidney cancer is Wilm's tumour.

In an embodiment, the cancer is bladder cancer. In an embodiment, the bladder cancer is transitional cell bladder cancer.

In an embodiment, the cancer is chosen from breast cancer, melanomas, colorectal cancer, glioblastoma and hepatocellular adenocarcinoma.

In one embodiment, the conjugate compound induces apoptosis on cancer cells.

For example, Katana-drug conjugates induce apoptosis in cancer cells such as for example ovarian cancer cells, melanoma cancer cells and breast cancer cells.

Figure 10:
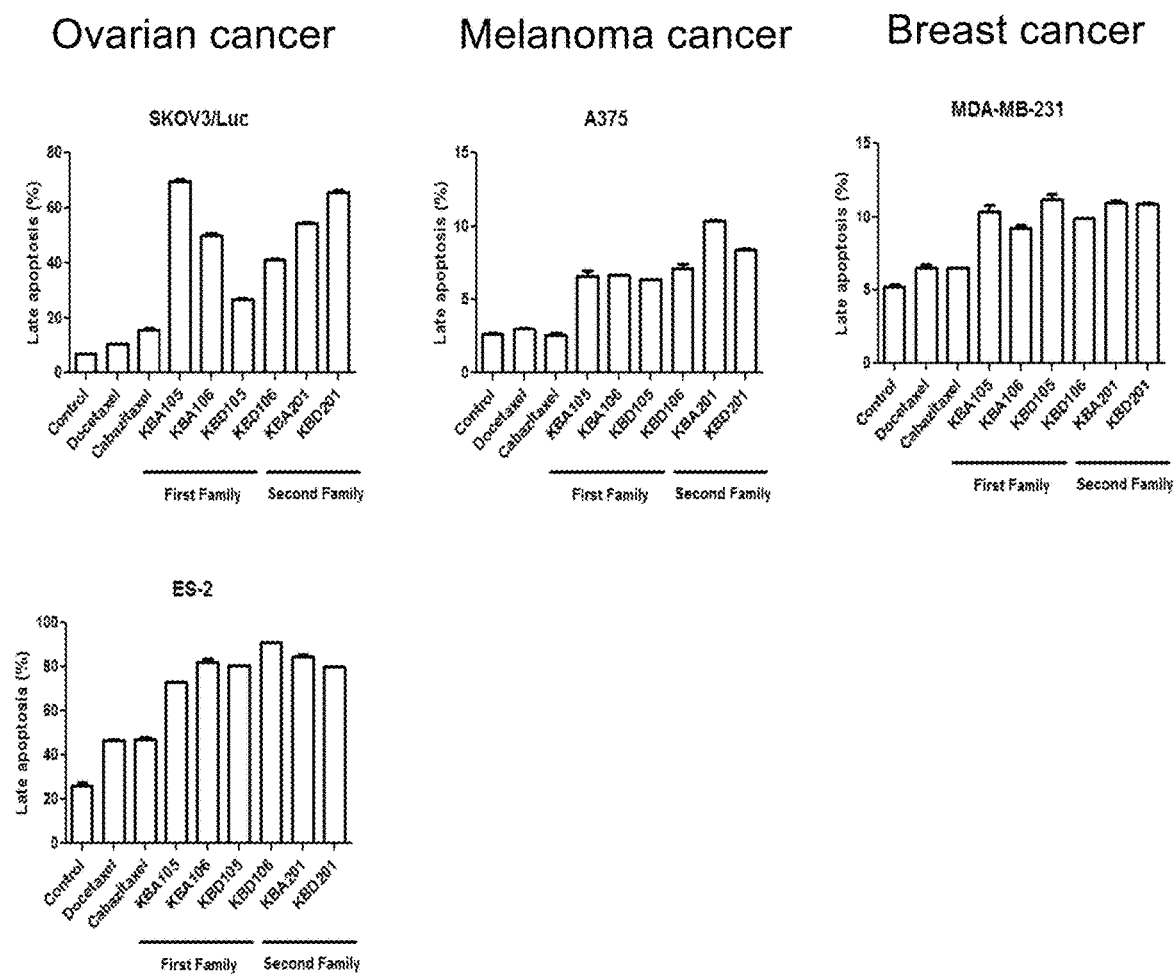
FIG. 10 shows the effect of Katana-drug conjugates on ovarian, skin and breast cancer cells apoptosis. Cancer cells were incubated for 5 hrs with 2 µM of Katana-drug conjugates or unconjugated Docetaxel or Cabazitaxel. After incubation, cells were washed and stained for Annexin V. Results are expressed in terms of apoptosis percentage for the different drugs.
Figure 30:
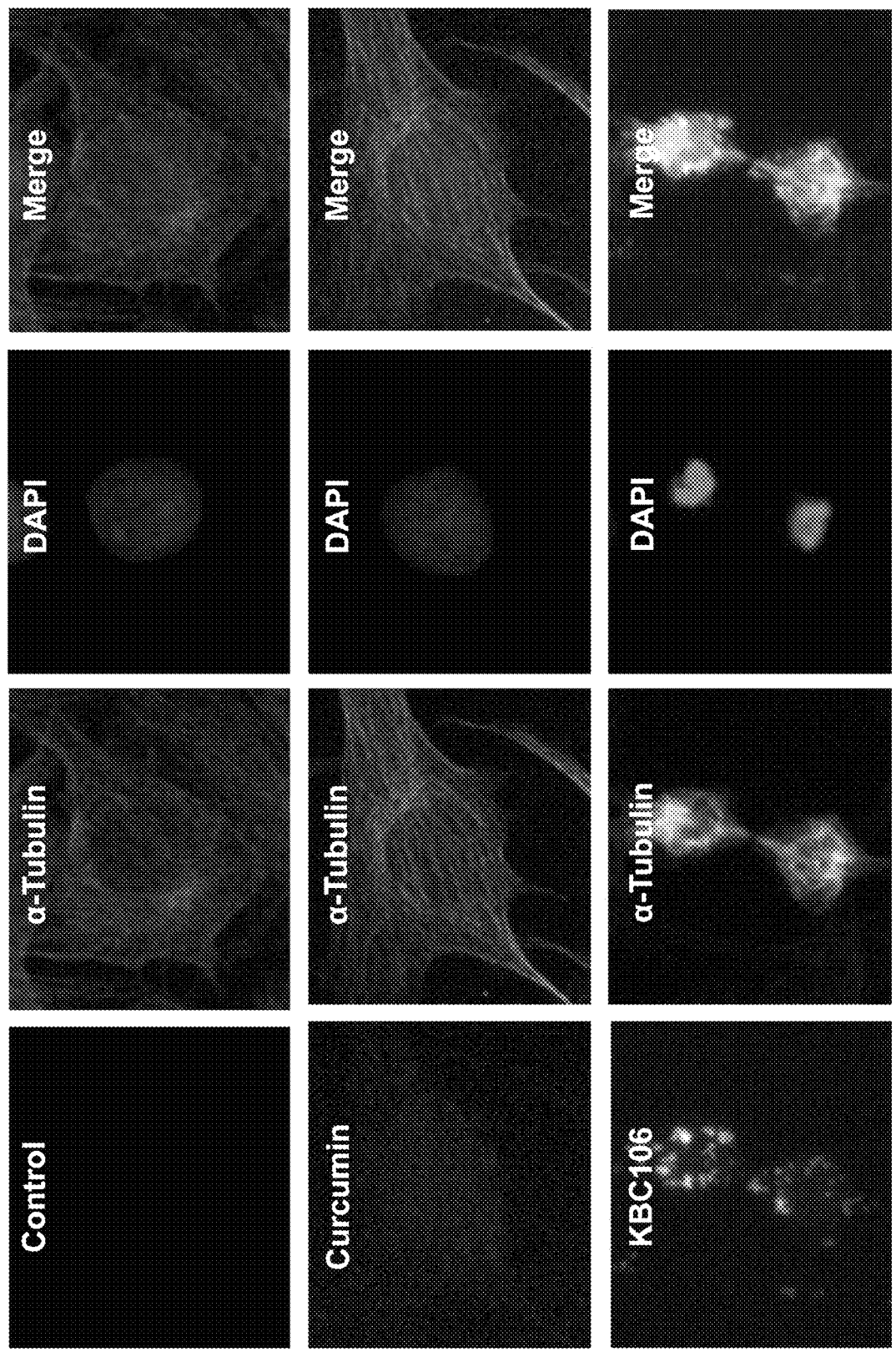
FIG. 30 is a demonstration that the Curcumin conjugate (KBC106) induces cancer cell apoptosis.

As shown in FIG. 10, docetaxel-conjugates and cabazitaxel conjugates are more potent than unconjugated docetaxel and cabazitaxel in inducing apoptosis in cancer cells. Similarly, as shown in FIG. 30, the curcumin conjugate induces greater apoptosis in cancer cells compared to non-conjugated curcumin.

In one embodiment, Katana-drug conjugates are also more potent than unconjugated therapeutic agent in inducing tumor suppression.

In one embodiment, the compounds disclosed herein can be used to treat cancer, for example in multidrug resistant cancer.

As shown in FIG. 6, the conjugate compounds were accumulated in MDCK-transfected cells with human multidrug resistant gene MDR1 at a faster rate and at higher concentrations in docetaxel conjugates compared to unconjugated docetaxel.

In one embodiment, the compounds disclosed herein also decrease migratory capacity of cancer cells.

Figure 16:
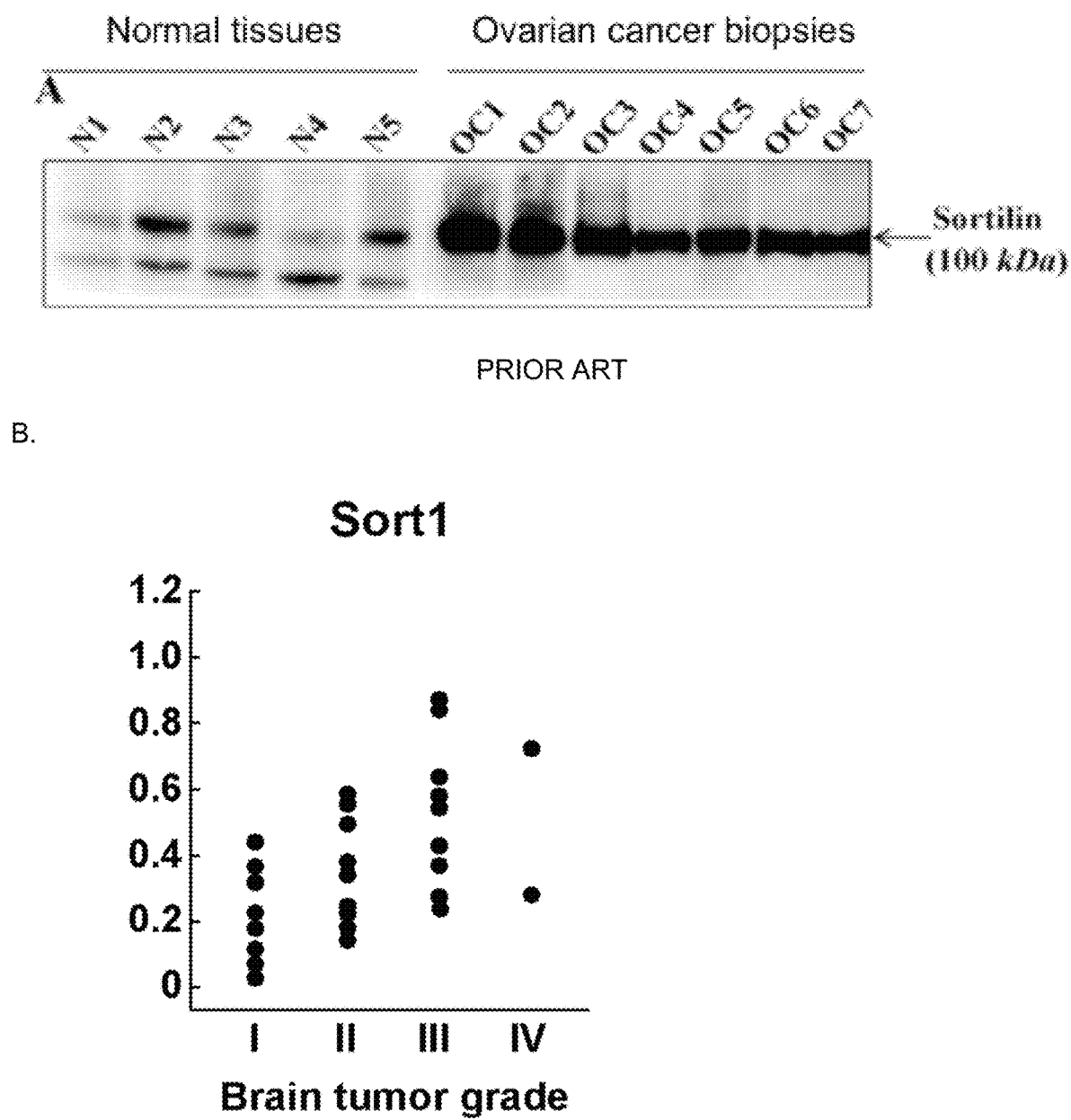
FIG. 16 is a representation of relative sortilin expression in ovarian cancers and brain tumors. 16A. Sortilin was detected by Western blot in human normal tissues and ovarian cancer biopsies (from Ghaemimanesh et al. 2014). Results show sortilin is overexpressed in ovarian cancer biopsies compared to normal tissues. Sortilin gene levels were estimated in cDNA samples (Origene; Rockville, Md., USA) from patients with different brain (16B) and ovarian (16C) tumor grades.
Figure 16:
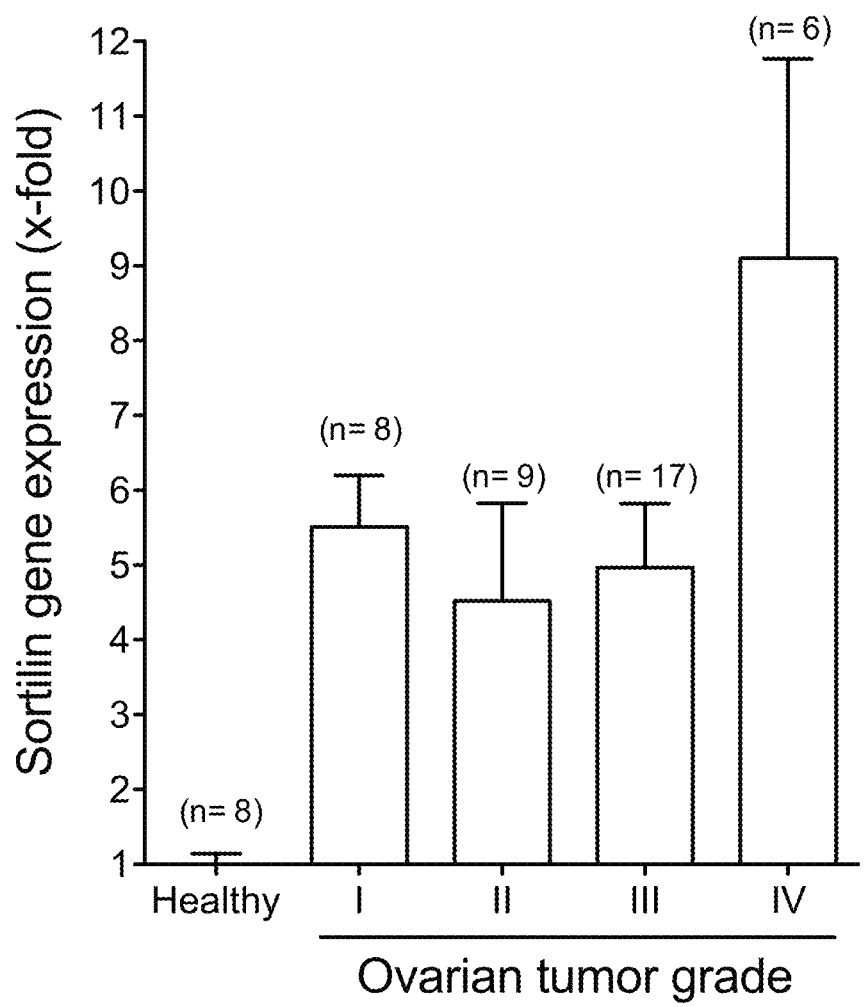

For example, as shown in FIG. 16, cell migration was evaluated in cancer cells incubated with conjugate compounds. The results show that Katana-drug conjugates strongly decreased the capacity of the cancer cells to migrate.

In one embodiment, the compounds disclosed herein can be used to reduce tumour growth.

As demonstrated in Example 4, Katana drug conjugates are more effective than unconjugated compounds in reducing tumour growth, as measured by quantitating tumour luminescence in a mouse xenograft tumour model.

The compounds disclosed herein may be used to treat diseases where sortilin/syndecan receptors are expressed and/or involved.

For example, the compounds herein disclosed may be used to treat inflammatory disease (Mortensen, 2014), lysosomal disorders (Coutinho, 2012, Prabakaran, 2012) and cardiovascular disease (Kjolby, 2015).

For example, there is provided a use of a conjugate compound herein disclosed for increasing cellular internalization of the at least one therapeutic agent.

For example, there is provided a use of at least one compound herein disclosed for treating a disease involving sortilin expression.

For example, the use is for treating a disease involving expression of at least one receptor chosen from vacuolar protein sorting 10 (Vps10) family of receptors.

For example, the at least one receptor is chosen from sortilin, SorL1, SorCS1, SorCS2, and SorCS3.

For example, the at least one receptor plays pleiotropic functions in protein trafficking and intracellular and intercellular signaling in neuronal and non-neuronal cells.

For example, there is provided a use of at least one compound herein disclosed for treating a cancer.

For example, there is provided a use of a compound herein disclosed in the manufacture of a medicament for treating cancer.

For example, the cancer is a cancer involving sortilin expression.

For example, the cancer is ovarian cancer, brain cancer, breast cancer, melanoma, colorectal cancer, glioblastoma, liver cancer, lung cancer, prostate cancer, cervical cancer, head cancer, gastric cancer, kidney cancer, endometrial cancer, testis cancer, urothelial cancer, acute lymphoblastic leukemia, acute myeloid leukemia, Hodgkin lymphoma, neuroblastoma, non-Hodgkin lymphoma, soft tissue cancer, bone sarcoma, thyroid cancer, transitional cell bladder cancer, Wilm's tumour, glioma, pancreatic cancer or spleen cancer.

For example, there is provided a use of a compound herein disclosed for selectively targeting cells expressing sortilin.

It is well known that certain anticancer agents are effective however are associated with adverse effects. Doxorubicin for example is associated with cardiotoxicity in a dose-dependent manner. In humans, the maximum cumulative dose of doxorubicin 550 mg/m$^2$. A cumulative dose exceeding this threshold is linked to an increased rate of cardiotoxicity. As mentioned herein, the compounds described herein selectively target cells expressing sortilin. As such, they offer selective delivery of anticancer agents to cancer cells expressing sortilin, thus decreasing general cellular toxicity caused by anticancer agents, such as doxorubicin.

For example, there is provided a use of a compound herein disclosed, in a drug delivery system.

For example, there is provided a use of a compound herein disclosed, in the context of a fusion protein, optionally wherein the fusion protein is engineered by using an expression system, optionally an expression system derived from bacteria, yeast, baculovirus/insect, plant cells, mammalian cells and filamentous fungi, optionally *Myceliophthora thermophila* fungi.

For example, there is provided a use of a compound herein disclosed, in the manufacture of a medicament for treating a disease that involves sortiin expression.

For example, there is provided a use of a compound herein disclosed, for increasing tolerability of a therapeutic agent.

For example, there is provided a use of a compound herein disclosed, for increasing tolerability of a therapeutic agent.

For example, there is provided a use of a compound herein disclosed, for increasing anti-proliferation activity of a therapeutic agent.

Another aspect is a library comprising at least two of compounds herein disclosed.

Yet another aspect is the use of a library herein described for identifying compounds that modulate a biological target.

As previously mentioned, the compounds herein disclosed may be used in the context of drug delivery systems. For example, the compounds may be connected, linked, mixed, adsorbed to the surface of nanoparticles, liposomes, graphene particles loaded with a therapeutic agent For example, the compounds can also be connected to the surface via a linker, an atom or a bond.

An aspect herein disclosed is a liposome, graphene or nanoparticle comprising at least one compound disclosed herein.

Another aspect is a liposome, graphene or nanoparticle coated with at least one compound disclosed herein.

Another aspect is a liposome, graphene or nanoparticle loaded with at least one therapeutic agent, gene or siRNA; and the liposome or nanoparticle is coated with at least one compound herein defined. For example, the at least one compound can be connected to the surface of the liposome or nanoparticle.

In one embodiment, the at least one compound is a peptide compound herein disclosed. In one embodiment, the at least one compound is a conjugate compound herein disclosed.

Different embodiments of liposomes or nanoparticles can be envisaged by the person skilled in the art. For example the liposome or nanoparticle can comprise at least one peptide compound herein disclosed coated on the surface of the liposome or nanoparticle and a therapeutic agent, for example an anticancer agent, within the liposome or nanoparticle. For example, the liposome or nanoparticle can comprise at least one conjugate compound herein disclosed coated on the surface of the liposome or nanoparticle and a therapeutic agent, for example an anticancer agent, within the liposome or nanoparticle.

For example, there is provided herein a multimer comprising two or more compounds herein disclosed.

For example, the two or more compounds herein disclosed are connected to each other directly or indirectly.

For example, the two or more compounds are directly connected via a covalent bond.

For example, the two or more compounds are indirectly connected via a linker.

For example, the multimer is a dimer, a trimer or a tetramer.

Further embodiments of the present disclosure will now be described with reference to the following Examples. It should be appreciated that these Examples are for the purposes of illustrating embodiments of the present disclosure, and do not limit the scope of the disclosure.

Example 1

Generation of Peptide Compounds

One of the major goals is to determine whether the Katana receptor-mediated platform could be efficacious against cancer cells by using peptide-drug conjugate that are aimed towards receptors expressed on these cells. The first family of Katana peptides is derived from bacterial cell penetrant protein whereas the second family is based on the sortilin ligands, progranulin and neurotensin (Table 1).

TABLE 1

Amino acid sequences of Katana peptides of sortilin-binding peptides derived from a baterial protein (family 1) and from progranulin and neurotensin, two sortilin ligands (family 2)

| Amino acid sequence | Amino acid length |
|---|---|
| Katana Biopharma Peptide (KBP) Family 1: | |
| KBP-101: IKLSGGVQAKAGVINMDKSESM (SEQ ID NO: 5) | 22 |
| KBP-102: Succinyl-IKLSGGVQAKAGVINMFKSESY (that comprises SEQ ID NO: 6 with a succinyl group attached at the N-terminal end) | 22 |
| KBP-103: IKLSGGVQAKAGVINMFKSESYK(Biotin) that comprises SEQ ID NO: 7 with biotin connected thereto at the C-terminal end) | 23 |
| KBP-104: GVQAKAGVINMFKSESY (SEQ ID NO: 8) | 17 |
| KBP-105: Acetyl-GVRAKAGVRNMFKSESY (SEQ ID NO: 14) | 17 |
| KBP-106 Acetyl-GVRAKAGVRN(Nle)FKSESY (SEQ ID NO: 15) | 17 |

TABLE 1-continued

Amino acid sequences of Katana peptides of sortilin-binding peptides derived from a baterial protein (family 1) and from progranulin and neurotensin, two sortilin ligands (family 2)

| Amino acid sequence | Amino acid length |
|---|---|
| Katana Biopharma Peptide (KBP) Family 2: | |
| KBP-201: YKSLRRKAPRVVDAPLRDPALRQLL (SEQ ID NO: 11) | 24 |
| KBP-202: YKSLRRKAPRVVDAYLRDPALRQLL (SEQ ID NO: 12) | 24 |
| KBP-203: YKSLRRKAPRVVDAYLRDPALRPLL (SEQ ID NO: 13) | 24 |

Surface plasmon resonance (SPR) was first used to investigate whether these peptides could be recognized by sortilin. For this approach, biotin was added on the C-terminal end of the Katana-Biopharma peptide during peptide synthesis. The biotinylated-peptide (KBP-103) was then immobilized on a streptavidin sensor chip using recommended procedures from the manufacturer. Increasing concentrations of a soluble form of sortilin was then injected over the sensor chip. Interactions between immobilized KBP-103 and the receptor sortilin was then monitored in real time. A representative interaction curve is shown in FIG. 1, and from the sensorgram curves the affinity constant as well as Ka and Kd were determined and are indicated in Table 2. Affinity constants ($K_D$, $K_a$ and $K_d$) were extracted from various injections using the BIA evaluation software. Affinity constant ($K_D$) of the Katana peptide for sortilin is in the low nM range indicating that the peptide has a high affinity for this receptor.

TABLE 2

Affinity constants $K_D$, $K_a$ and $K_d$

| $K_D$ | $k_a$ | $k_d$ |
|---|---|---|
| 2.55*10$^{-8}$ M | 6.829*10$^5$ M$^{-1}$ s$^{-1}$ | 0.0174 s$^{-1}$ |

Figure 3:
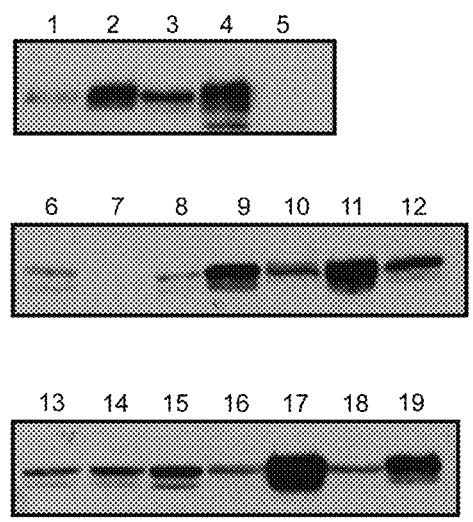
FIG. 3 shows the immunodetection of sortilin in human cancer cell lines. Equal amounts of protein from human cancer cell lysates were separated by gel electrophoresis. After electrophoresis, the proteins were transferred to PVDF membrane and sortilin was immunodetected using a monoclonal antibody directed against this sortilin receptor. Sortilin could be visualized by a secondary antibody directed against mouse IgG linked to horseradish peroxidase and chemiluminescent reagents. 1. Glioblastoma (U-87 MG), 2. Glioblastoma (U-251), 3. Medulloblastoma (Daoy), 4. Hepatocellular carcinoma (Hep G2), 5. Osteosarcoma (MG-63), 6. Lung adenocarcinoma (Calu-3), 7. Large cell lung carcinoma (NCI-H460), 8. Lung carcinoma (A-549), 9. Breast adenocarcinoma (MDA-MB-231), 10. Breast ductal carcinoma (MDA-MB-435s), 11. Breast adenocarcinoma (MCF-7), 12. Breast ductal carcinoma (ZR-75-1), 13. Ovary adenocarcinoma (SK-OV-3), 14. Cervix adenocarcinoma (Hela), 15. Uterine sarcoma (MES-SA), 16. Prostate adenocarcinoma (PC-3), 17. Malignant melanoma (SK-MEL-28), 18. Malignant melanoma (A-375), 19. Colorectal adenocarcinoma (HT-29).

The expression of sortilin in various cancer cells by Western blots was also investigated. Results show that sortilin can be detected in most of the cancer cells tested. In some cases, the expression levels of this receptor were very high. High expression was found in many breast cancer cells, melanomas, colorectal, glioblastoma and hepatocellular adenocarcinoma (FIG. 3). This is in agreement with the literature since sortilin has been reported to be expressed in different solid tumours including breast, colorectal, lung, prostate and ovarian cancers (Roseli, 2015; Ghaemimanesh, 2014; Hammati, 2009).

Example 2

Generation of Katana-Peptide Drug Conjugates

Docetaxel and Doxorubicin were first chosen for the proof of principle for anticancer agents, whereas curcumin was selected among phytochemicals. Docetaxel is a semi-synthetic analogue of paclitaxel, an extract from the bark of the rare Pacific yew tree *Taxus brevifolia*. This drug has been approved by the FDA (National Cancer Institute) for the treatment of locally advanced or metastatic breast cancer, head and neck cancer, gastric cancer, hormone-refractory prostate cancer and non small-cell lung cancer. Docetaxel can be used as a single agent or in combination with other chemotherapeutic drugs depending of specific cancer type and stage. Cabazitaxel (previously XRP-6258, trade name Jevtana™) is a semi-synthetic derivative of a natural taxoid. It is a microtubule inhibitor that was developed by Sanofi-Aventis. It was approved by the U.S. FDA for the treatment of hormone-refractory prostate cancer on Jun. 17, 2010. Doxorubicin is an anthracycline antitumour antibiotic (note: in this context, this does not mean it is used to treat bacterial infections) closely related to the natural product Daunomycin and, like all anthracyclines, works by intercalating DNA, with the most serious adverse effect being life-threatening heart damage (National Cancer Institute). It is approved to be used alone or with other drugs to treat: acute lymphoblastic leukemia (ALL), acute myeloid leukemia (AML), breast cancer, gastric (stomach) cancer, Hodgkin lymphoma, neuroblastoma, non-Hodgkin lymphoma, ovarian cancer, small cell lung cancer, soft tissue and bone sarcomas, thyroid cancer, transitional cell bladder cancer and Wilm's tumour. Curcumin (diferuloylmethane) is a yellow pigment present in the spice turmeric (*Curcuma longa*) that has been associated with antioxidant, anti-inflammatory, anticancer, antiviral, and antibacterial activities as indicated by over 6,000 citations (Hosseini, 2015).

Figure 5:
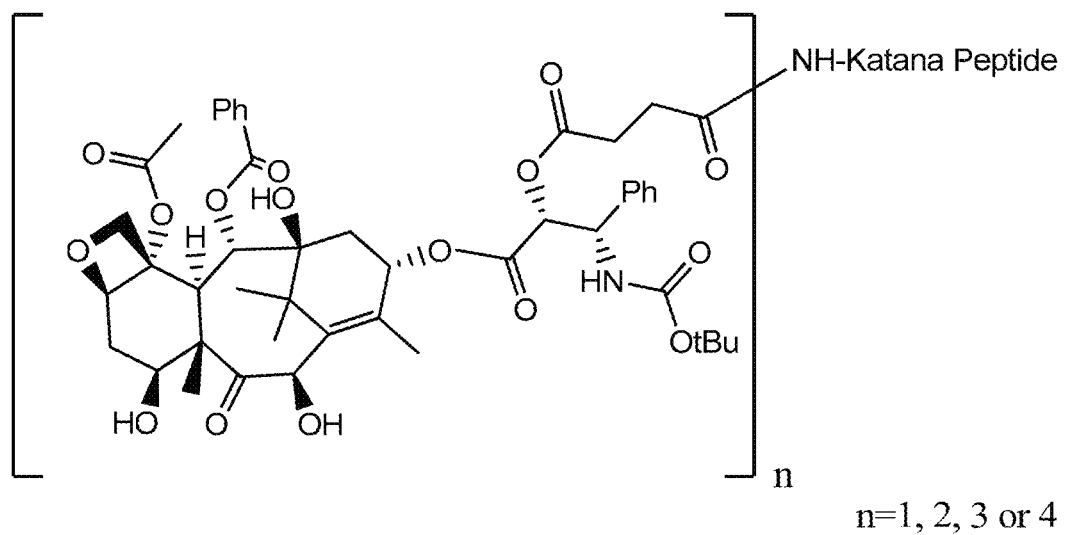
FIG. 5 shows the structures of drug-Katana peptide conjugates. Examples of Katana peptide conjugates with docetaxel (A) and doxorubicin (B) and of a phytochemical-Katana peptide conjugate with curcumin (C). Different numbers (n=1 to 4) of anticancer agent or phytochemical molecules can be incorporated on the N-terminal and lysines of the Katana peptide.
Figure 5:
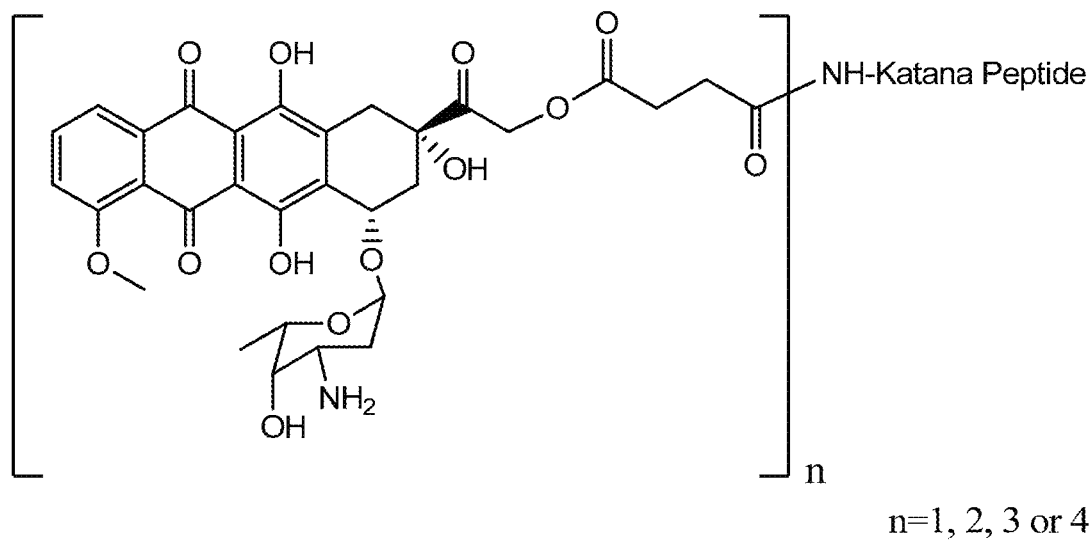
Figure 5:
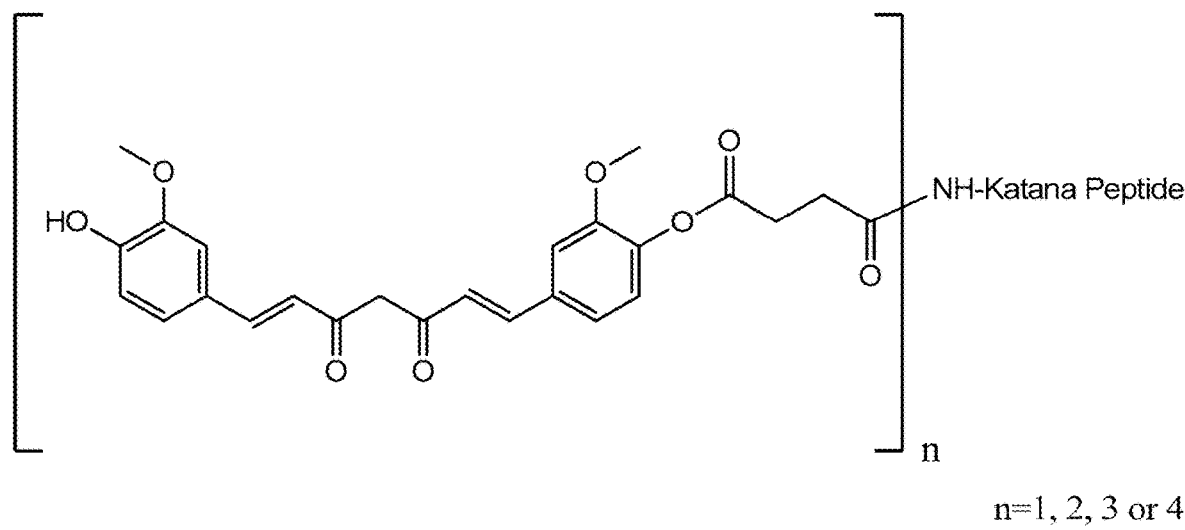

Anticancer agents (e.g. Docetaxel, Cabazitaxel, Doxorubicin) or phytochemicals (e.g. curcumin) can be conjugated on the peptide using amine conjugation strategies. Briefly, Docetaxel can be conjugated to Katana peptide(s) on free amines available on the peptide (lysine or amino-terminal) by forming a peptide bond (amide bond) with activated-Docetaxel. In KBP-101, 4 free amines are available for the conjugation, the N-terminal and 3 lysines. Different conjugates can therefore be generated by the addition of 1, 2, 3 and 4 Docetaxel to the peptide. Similar conjugation strategies can be used with Doxorubicin and curcumin (FIGS. 4 and 5).

For example, the following strategy has been used for the conjugation of drug to Katana's peptide. The N-terminal was blocked and all the 3 other conjugation sites were saturated with Docetaxel, thereby forming a peptide drug conjugate of 3 molecules of Docetaxel per peptide molecule. The whole conjugation was analyzed by HPLC and conjugates were confirmed by Mass spectra (MALDI-TOF). Docetaxel could be released by the cleavage of the ester bond by esterases.

Anticancer agents (ex. Docetaxel, Doxorubicin) and phytochemicals (ex. curcumin) are conjugated using a cleavable linker. The native drug could then be released from the vector by the action of esterases on the ester bond. Examples for structures of 2 Katana-anticancer agent conjugates (A and B) and one phytochemical-Katana drug conjugate (C) are presented in FIG. 5.

Different conjugates between Docetaxel, Doxorubicin, Curcumin Cabazitaxel and Katana peptides have been generated. These conjugates are summarized in Table 3 below.

TABLE 3

| Products | Amino acid sequences |
|---|---|
| Docetaxel-conjugates | |
| KBA102 (3:1) | Succinyl-IK(Doce)LSGGVQAK(Doce)AGVINMFK(Doce)SESY |
| KBA104 (2:1) | GVQAK(Doce)AGVINMFK(Doce)SESY |
| KBA105 (2:1) | Acetyl-GVRAK(Doce)AGVRNMFK(Doce)SESY |
| KBA106 (2:1) | Acetyl-GVRAK(Doce)AGVRN(Nle)FK(Doce)SESY |
| KBA201 (2:1) | Acetyl-YK(Doce)SLRRK(Doce)APRWDAPLRDPALRQLL |
| Doxorubicin-conjugates | |
| KBB104 (2:1) | GVQAK(Doxo)AGVINMFK(Doxo)SESY |
| KBB106 (2:1) | Acetyl-GVRAK(Doxo)AGVRN(Nle)FK(Doxo)SESY |
| KBB201 (2:1) | Acetyl-YK(Doxo)SLRRK(Doxo)APRWDAPLRDPALRQLL |
| Curcumin-conjugates | |
| KBC106 (2:1) | Acetyl-GVRAK(Cur)AGVRN(Nle)FK(Cur)SESY |
| Cabazitaxel-conjugates | |
| KBD105 (2:1) | Acetyl-GVRAK(Cab)AGVRNMFK(Cab)SESY |
| KBD106 (2:1) | Acetyl-GVRAK(Cab)AGVRN(Nle)FK(Cab)SESY |
| KBD201 (2:1) | Acetyl-YK(Cab)SLRRK(Cab)APRWDAPLRDPALRQLL |

Example 3

In Vitro Effects of Conjugate Compounds

The effect of the Docetaxel-Katana peptide conjugate on various cell line proliferations was evaluated and compared to unconjugated Docetaxel (Table 4). IC50 values obtained for the Docetaxel-Katana peptide conjugate were very similar to those of Docetaxel in the cancer cells tested. Overall, these results show that the potency of Docetaxel-Katana peptide conjugate to block cell proliferation in vitro is similar to unconjugated Docetaxel indicating that the potency of anticancer agents remains unaltered upon their conjugation.

In order to determine whether the anticancer drug-Katana-peptide conjugates could also be P-gp substrates, MDCK-transfected cells with human MDR1 were used (MDCK-MDR1). As shown in FIG. 6, the accumulation of the P-gp substrate [$^3$H]-Docetaxel increased by 2-fold in the presence of cyclosporin A (CsA), a P-gp competitive inhibitor. However, the lack of CsA effect on the accumulation of [$^{125}$I]-Docetaxel-Katana peptide conjugate indicates that upon its conjugation to KBP, the drug moiety is not recognized anymore by P-gp. The latter results confirm that Katana conjugates bypass efficiently the efflux action of P-gp.

In addition, the uptake of radiolabeled [$^{125}$I]-Katana conjugate (KBA-105) was compared to that of unconjugated

TABLE 4

Effect of Katana-drug conjugates on cell proliferation using the [$^3$H[-Thymidine incorporation assay. IC50 (nM) obtained from anti-proliferation curves are presented.

Figure 7:
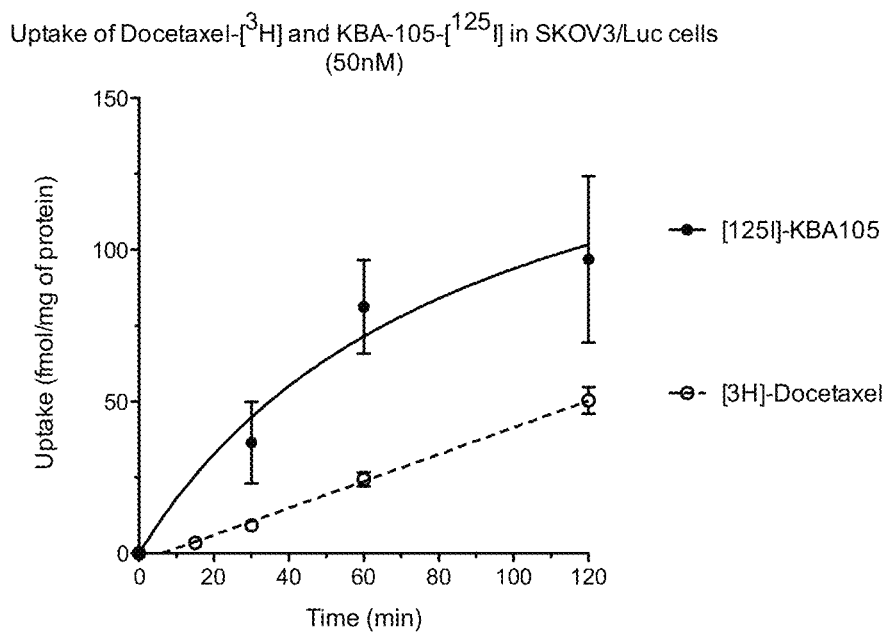
FIG. 7 shows the uptake of radiolabeled Docetaxel and Katana conjugate (KBA105) in SKOV3 (FIG. 7A) and SK-MEL28 (FIG. 7B) cancer cells. Cells were incubated for up to 2 hrs with radiolabeled compounds. After incubation, cells were washed 3-times with PBS and accumulated radioactivity was then quantified. Results were expressed in terms of uptake (fmol/mg of protein) as function of time.
Figure 7:
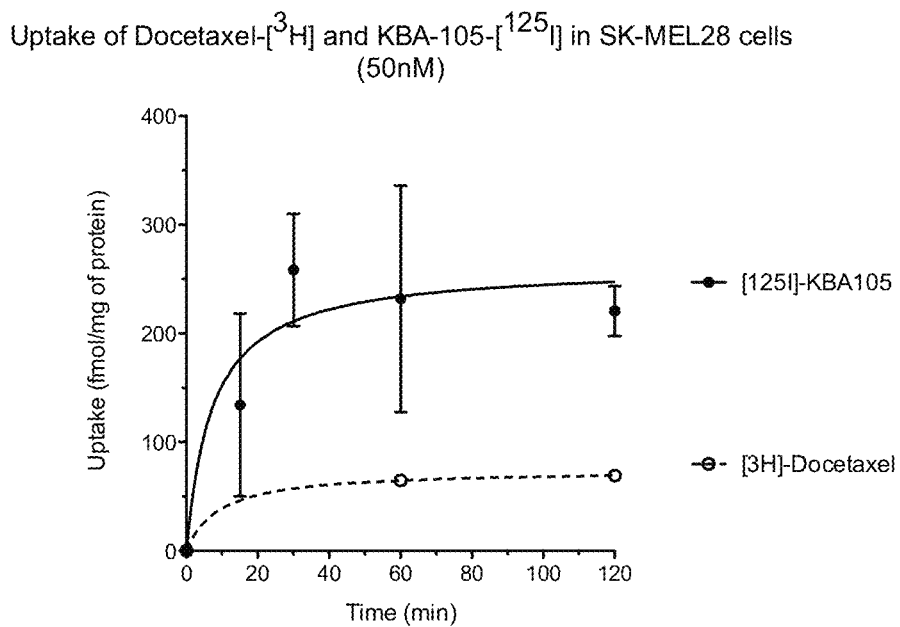

| | | IC50 (nM) | | | | | |
|---|---|---|---|---|---|---|---|
| Tissues | Cells | Docetaxel | | Cabazitaxel | | Doxorubicin | |
| Ovary | ES-2 | Docetaxel: | 1.30 | Cabazitaxel: | 0.66 | Doxorubicin: | 73.5 |
| | | KBA-105: | 0.70 | KBD-105: | 0.66 | KBB-106: | 66.1 |
| | | KBA-106: | 1.27 | KBD-106: | 0.24 | KBB-201: | 83.3 |
| | | KBA-201: | 3.48 | KBD-201: | 0.70 | | |
| Breast | MDA-MB-231 | Docetaxel: | 0.68 | Cabazitaxel: | 0.44 | Doxorubicin: | 9.7 |
| | | KBA-105: | 1.03 | KBD-105: | 0.60 | KBB-106: | 15.9 |
| | | KBA-106: | 0.38 | KBD-106: | 0.45 | KBB-201: | 17.3 |
| | | KBA-201: | 0.77 | KBD-201: | 0.89 | | |
| Skin | SK-MEL-28 | Docetaxel: | 0.69 | Cabazitaxel: | 0.12 | Doxorubicin: | 79.3 |
| | | KBA-105: | 0.09 | KBD-105: | 0.86 | KBB-106: | 68.7 |
| | | KBA-106: | 0.07 | KBD-106: | 0.04 | KBB-201: | 81.0 |
| | | KBA-201: | 0.43 | KBD-201: | 0.26 | | |
| | A-375 | Docetaxel: | 0.92 | Cabazitaxel: | 0.34 | Doxorubicin: | 11.8 |
| | | KBA-105: | 0.43 | KBD-105: | 0.45 | KBB-106: | 13.8 |
| | | KBA-106: | 0.13 | KBD-106: | 0.42 | KBB-201: | 14.2 |
| | | KBA-201: | 0.81 | KBD-201: | 0.41 | | | radiolabeled [³H]-Docetaxel in the ovarian SKOV3 cancer cells and in SKMEL-28 melanoma cancer cells in FIG. 7. Results demonstrate that the conjugate uptake in SKOV3 (FIG. 7A) as well as in SKMEL-28 cells (FIG. 7B) is faster and accumulates at higher concentrations than the unconjugated Docetaxel.

Figure 8:
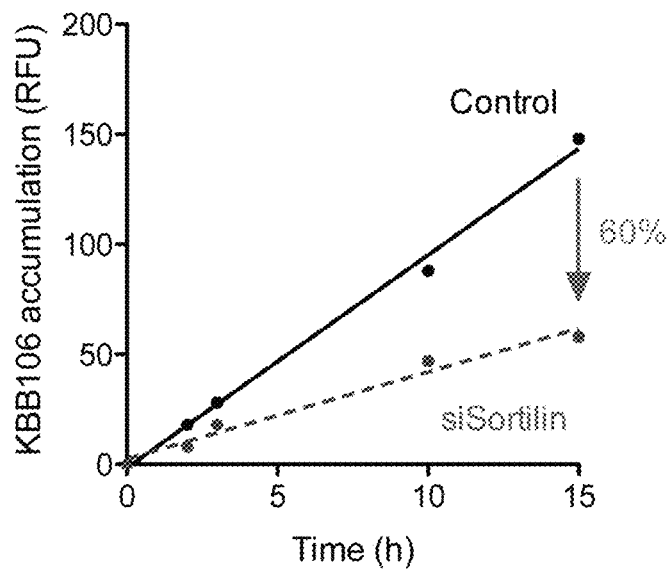
FIG. 8 shows the uptake of Katana Doxorubicin conjugate (KBB106) is reduced in cells where sortilin expression is reduced or by sortilin ligands. A. Ovarian cancer cells were transfected with sortilin siRNA (siSortilin) for 24 hrs and then incubated with KBB106. Accumulation of KBB106 was monitored by the released of fluorescent Doxorubicin as a function of time. B. Ovarian cancer cells were incubated with KBB106 in the presence or absence of sortilin ligand (Katana peptide, progranulin). KBB106 accumulation was estimated by the released of fluorescent Doxorubicin.
Figure 8:
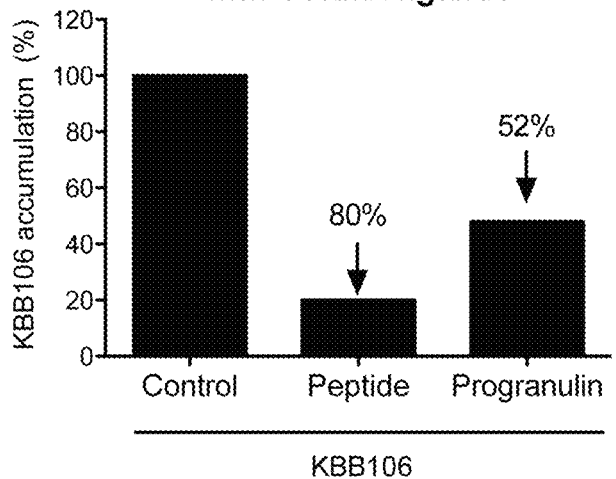

The uptake of the Katana conjugate is increased in cells expressing the sortilin receptor. As shown in FIG. 8, the uptake of the Katana Doxorubicin conjugate (KBB106) was reduced in cells where sortilin expression was reduced. For example, FIG. 8A shows decreased uptake of KBB106 in ovarian cancer cells transfected with sortilin siRNA and FIG. 8B shows decreased uptake of KBB106 in ovarian cancer cells due to pharmacological inhibition with sortilin ligands, namely the Katana peptide and progranulin.

Figure 9:
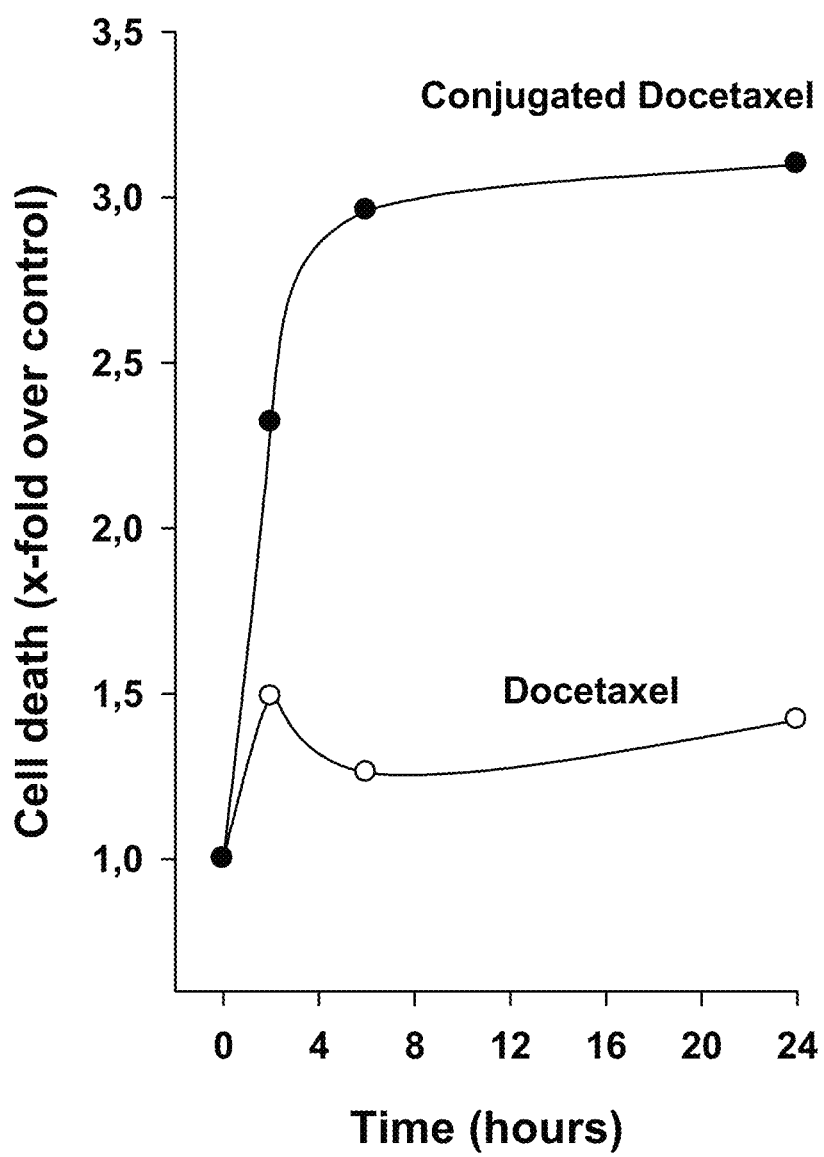
FIG. 9 shows that the conjugated-Docetaxel induces a better and sustained cell death of ovarian cancer cells. 9A. Effect of KBA105 on ovarian (SKOV3) cancer cells apoptosis was compared to that of Docetaxel. After incubation, cells were washed and stained for Annexin V. 9B. Conjugated Docetaxel induces a stronger apoptosis than unconjugated Docetaxel. This level of apoptosis is similar to that measure for Docetaxel in the presence of the P-gp (MDR1) inhibitor Cyclosporine A (CsA). 9C. Dose-dependent increased apoptotic potential by KBA015 compared to Docetaxel. Cells were incubated for 5 hrs with increasing concentration of KBA105 or Docetaxel and levels of apoptosis was then determined. Results are expressed in terms of apoptosis percentage as a function of drug concentration.
Figure 9:
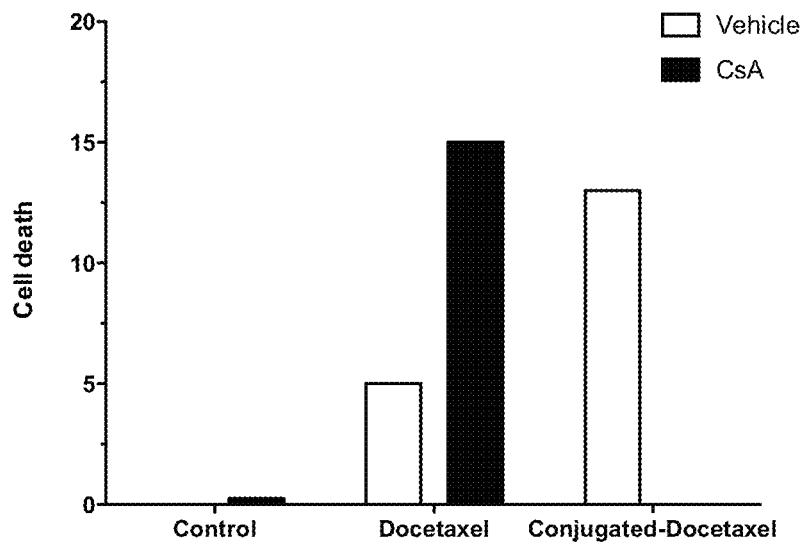
Figure 9:
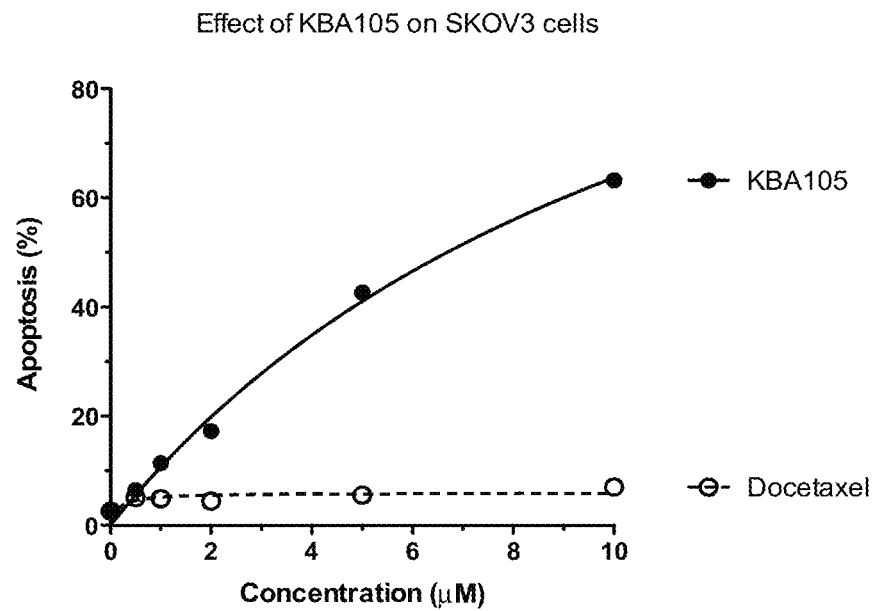

The effect of Docetaxel and conjugated Docetaxel on KB-peptide on ovarian cancer cell death was also evaluated by flow cytometry analysis using Annexin V/PI staining (FIG. 9). Results indicate that conjugated Docetaxel induced a higher and sustained cell death compared to the free drug (FIG. 9A). In order to induce a similar cell death, addition of the P-gp inhibitor Cyclosporine A (CsA) is required (FIG. 9B). These results show that the KBP-Docetaxel conjugate is more potent, in part through its ability to bypass the P-gp efflux pump.

The effect of increasing concentration of the Docetaxel-Katana peptide conjugate (KBA-105) or Docetaxel concentration on apoptosis of ovarian SKOV3 cancer cells (FIG. 9) after 5 hours of exposure to the drugs was also assessed. Results show that the KBA-105 conjugate induces apoptosis of these cancer cells after a relatively short incubation time.

This apoptosis assay was used to screen the conjugates on various cancer cells (FIG. 10). Results indicate that after 5 hours, all Katana-drug conjugates induce apoptosis of the tested cancer cell models. Most of them are also more potent than the unconjugated parent drugs, Docetaxel or Cabazitaxel.

Figure 11:
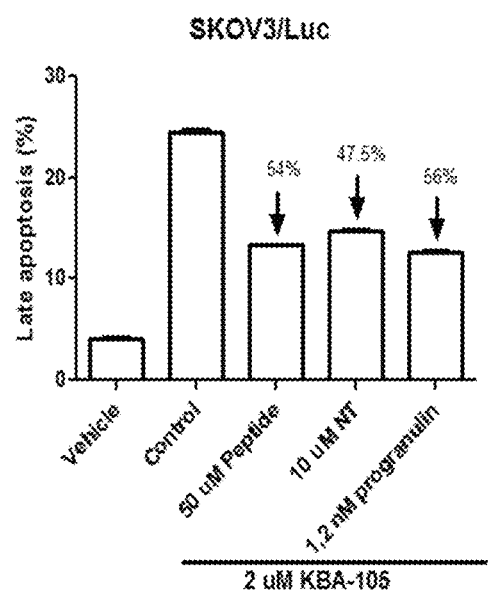
FIG. 11 shows the reversal of Katana-drug conjugate effect on cancer cell apoptosis by unconjugated peptide and sortilin ligands. Ovarian (SKOV3) cancer cells were incubated for 5 hrs with 2 µM of Docetaxe Katana-drug conjugates KBA-105 (11A) and KBA-201 (11B) in the absence or presence of free peptide, neurotensin (NT) and progranulin. After incubation, cells were washed and stained for Annexin V. Results are expressed in terms of apoptosis percentage of SKOV3 cancer cells.
Figure 11:
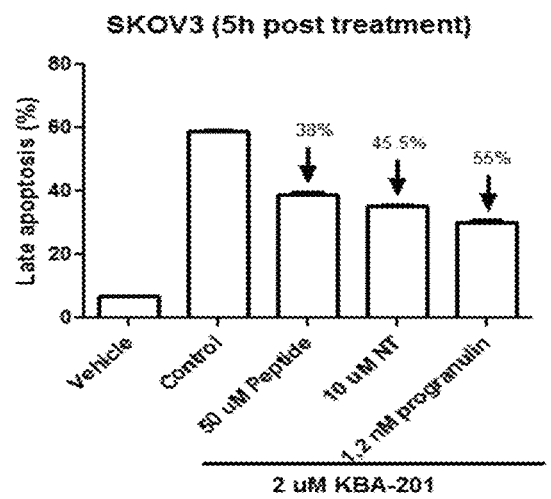

In order to determine whether the apoptosis induced by the Katana-drug conjugates was associated to receptor-mediated endocytosis, the assay was performed in the absence or presence of an excess of free peptide and two sortilin ligand neurotensin (NT) or Progranulin (FIG. 11). The addition of the free peptide reversed the apoptosis of SKOV3 (FIG. 11A) and SK-MEL28 (FIG. 11B) induced by the conjugate, indicating that induction of these cells by KBA-105 is receptor-mediated. Furthermore, the two sortilin ligands, neurotensin and progranulin also inhibit the apoptosis induced by the Katana-drug conjugate, suggesting that sortilin is involved in this receptor-mediated induction of apoptosis.

Figure 12:
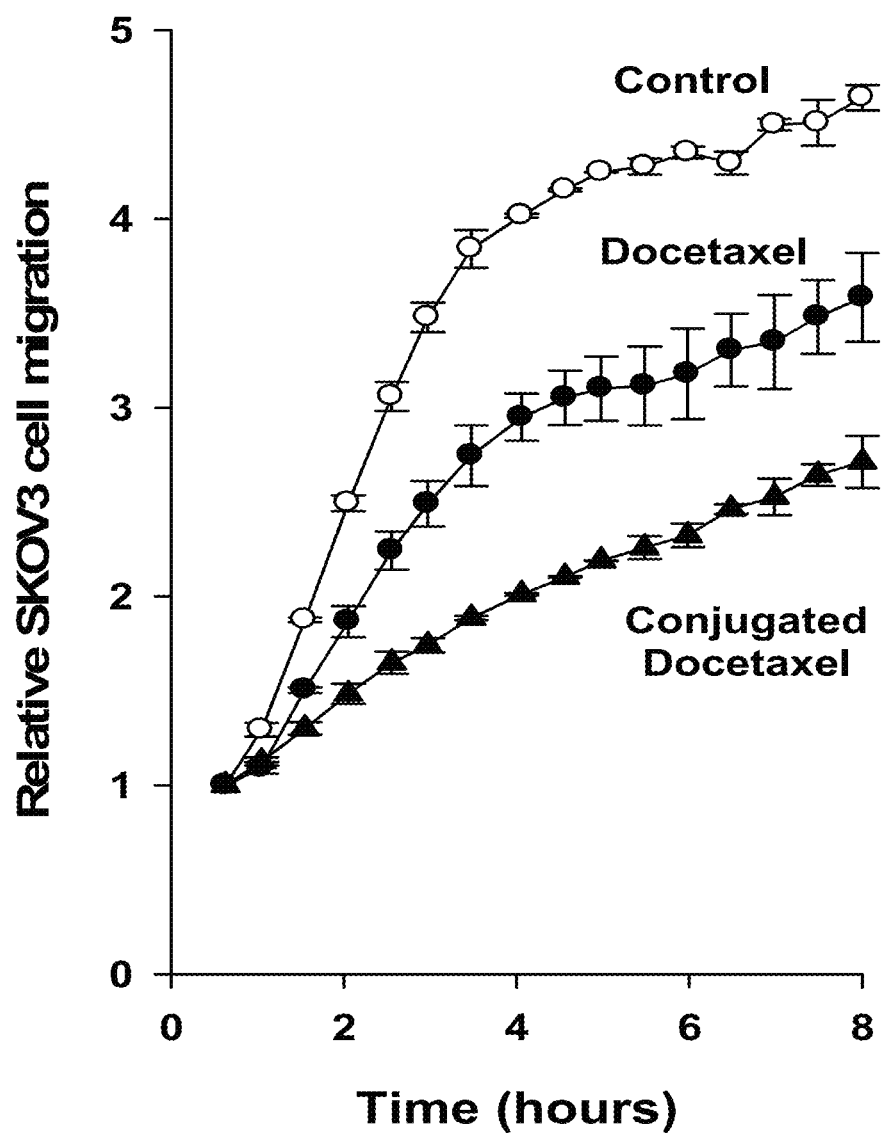
FIG. 12 shows increased anti-migratory effects of Docetaxel conjugated to the Katana-peptide on ovarian cancer cells.

The impact of KBP products on the migration of SKOV3 ovarian cancer cells. These cancer cells were incubated for 2 hours with either free docetaxel or a Katana-docetaxel conjugate and cell migration was then measured in real time as a function of time using xCELLigence biosensor system. This assay reflects the cellular effects of these molecules on SKOV3 ovarian cancer cell functions. As shown in FIG. 12, the Katana-Docetaxel conjugate has a stronger effect on SKOV3 cells, resulting in a stronger inhibition of their migration when compared to free Docetaxel. Stronger inhibition of cancer cell migration by the conjugated Docetaxel is an indication that the invasion or metastatic potential of these cancer cells will be more affected by the conjugate than by unconjugated Docetaxel.

Figure 13:
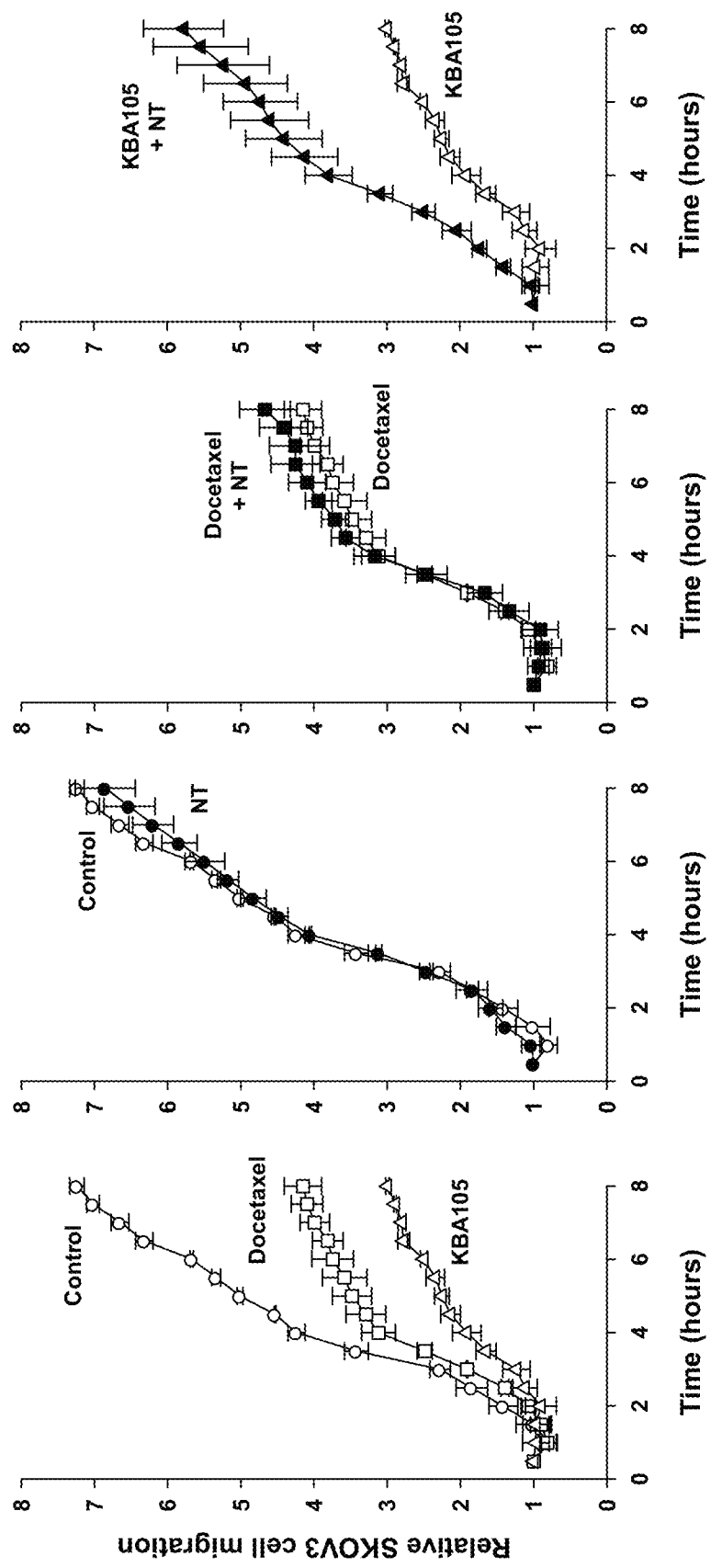
FIG. 13 is a series of graphs providing validation of the Katana platform delivery and evidence for receptor-mediated internalization of conjugated-Docetaxel in ovarian cancer cells. Co-incubation of neurotensin (13A) or the Katana-peptide (free peptide) (13B) with docetaxel does not alter the effect of docetaxel on cell migration. In contrast, the addition of the free peptide or neurotensin to Katana-docetaxel conjugate reverses its effects on SKOV3 migration. 13C. Results show that sortilin gene silencing with specific sortilin siRNA reverses the effect of the Docetaxel conjugate (KBA105) on ovarian cancer cells migration.
Figure 13:
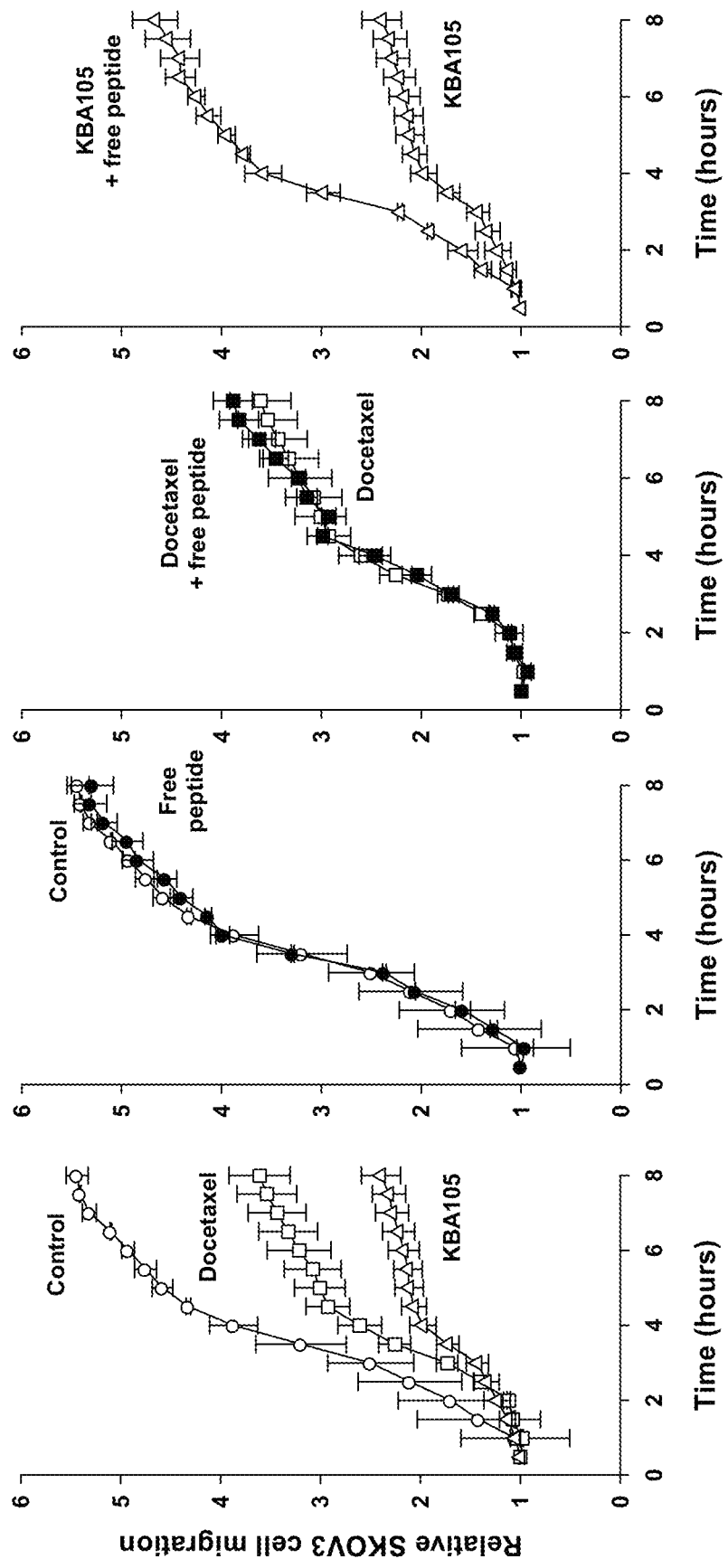
Figure 13:
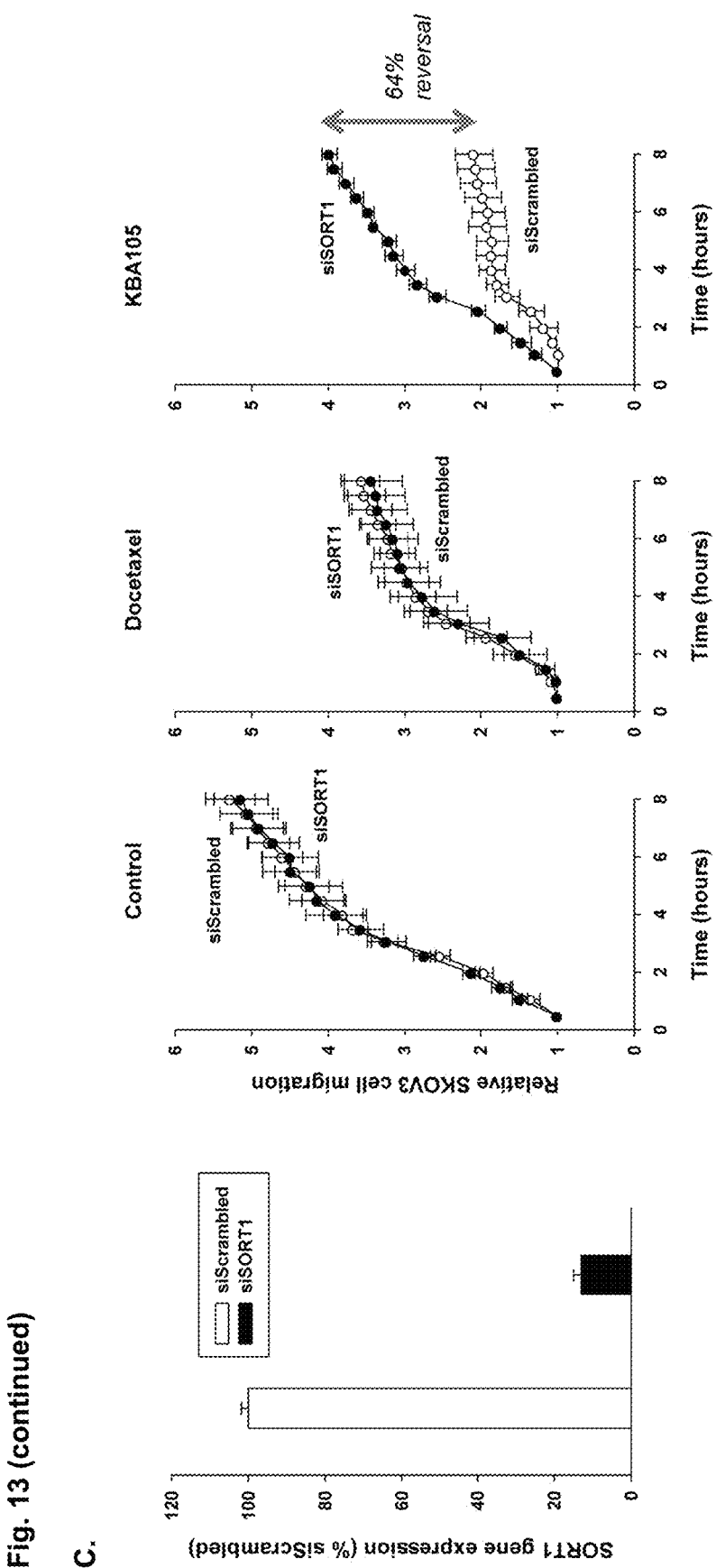

Interestingly, addition of either an excess of free Katana peptide (FIG. 13A) or neurotensin (FIG. 13B) strongly reversed the migratory effect of the Katana-Docetaxel conjugate. The reduction in cancer cell migration by free Docetaxel was unaffected by either free Katana-peptide or neurotensin. In addition, it was found that sortilin gene silencing with specific sortilin siRNA reversed the effect of the Katana-Docetaxel conjugate on cancer cell migration (FIG. 13C). These results support the concept that the Katana-Docetaxel conjugate has a distinct mechanism of action, different from that of the free drug. The fact that the sortilin ligand neurotensin significantly reversed the cellular effect of the conjugate further supports the implication of a receptor member of the sortilin family in the conjugate internalization or mechanism of action.

Figure 14:
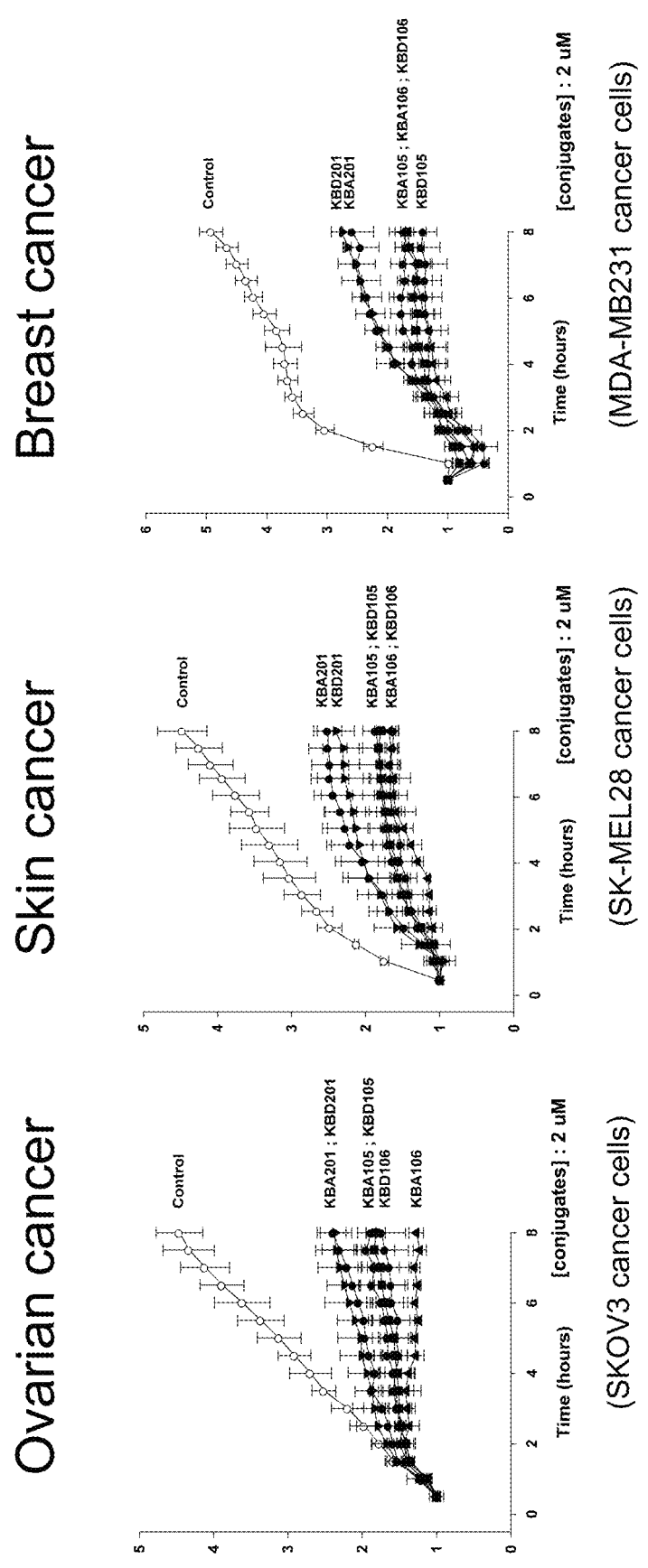
FIG. 14 shows the effect of Katana-drug conjugates on ovarian, skin and breast cancer cell migration. The cells were incubated for 2 hrs with different Katana Taxane conjugates and cell migration was then performed. All conjugates strongly affected the migration of the various cancer cells.

The effect of Docetaxel and KBP-Docetaxel on cell migration after gene silencing of sortilin using specific siRNA or a scrambled siRNA sequence was evaluated. Under the experimental conditions used, sortilin gene expression was reduced by about 80%. Results in FIG. 14 clearly show that the effect of the free Docetaxel on SKOV3 cell migration was unaffected by the reduction of sortilin expression. In contrast, the effect of the conjugated-Docetaxel is strongly reduced when sortilin expression is low. Reduction of sortilin expression using specific siRNAs reversed the conjugated-Docetaxel cytotoxic effects, but not that of free Docetaxel in ovarian cancer cells.

Figure 15:
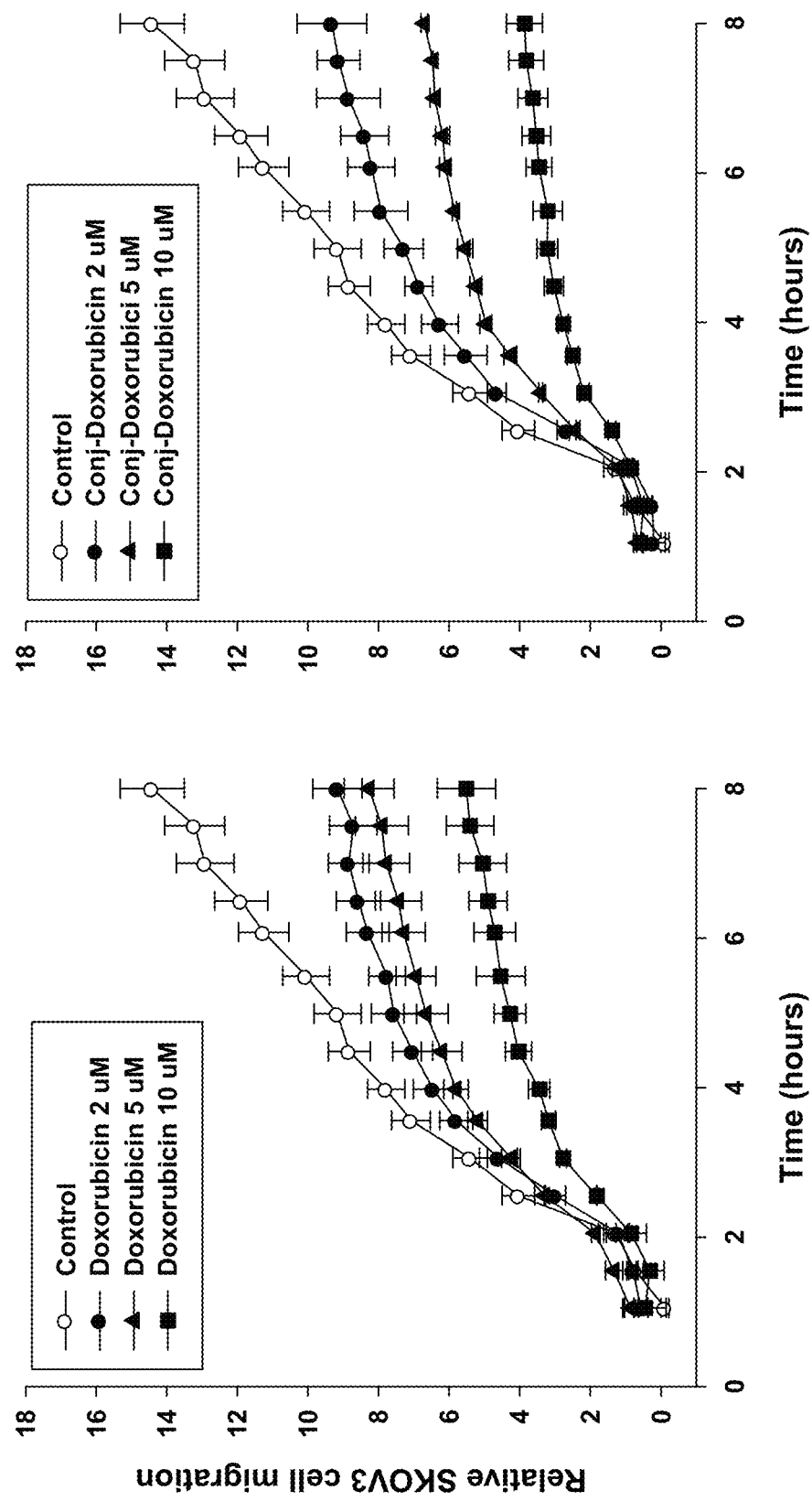
FIG. 15 shows of the effect of Katana-drug conjugates on ovarian cancer cell migration. 15A. Cells were incubated for 2 hrs with increasing concentration of Doxorubicin or conjugated Doxorubicin (KBB106) and cell migration was performed. 15B. Results show that Neurotensin (NT) and the Katana peptide (KBP106) reversed the effect of KBB106 on ovarian cancer cell (ES-2) migration. 15C. Progranulin (PGR), a sortilin ligand, also reversed the effect of the Doxorubicin conjugate (KBB106) on ovarian cancer cell (ES-2) migration.
Figure 15:
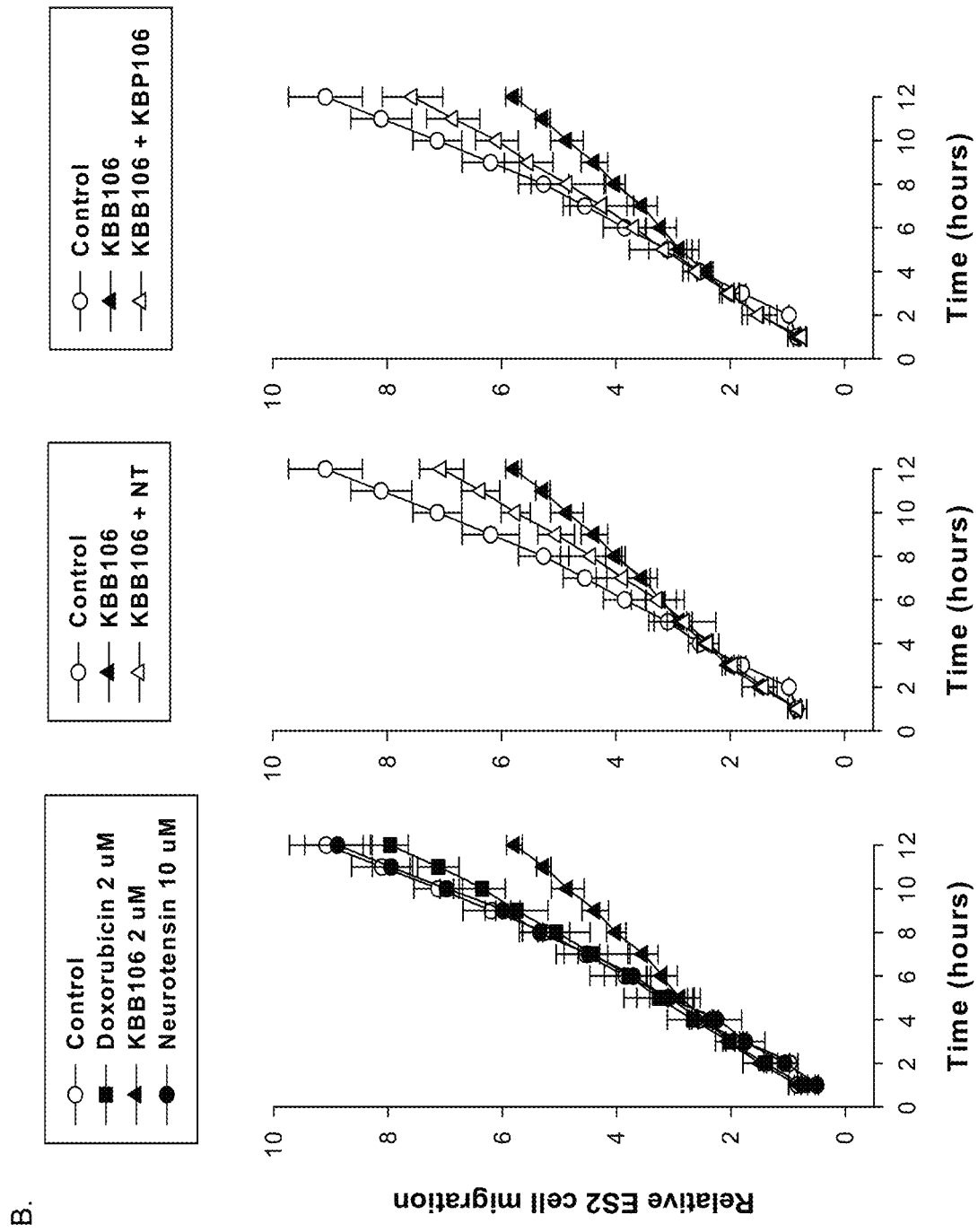
Figure 15:
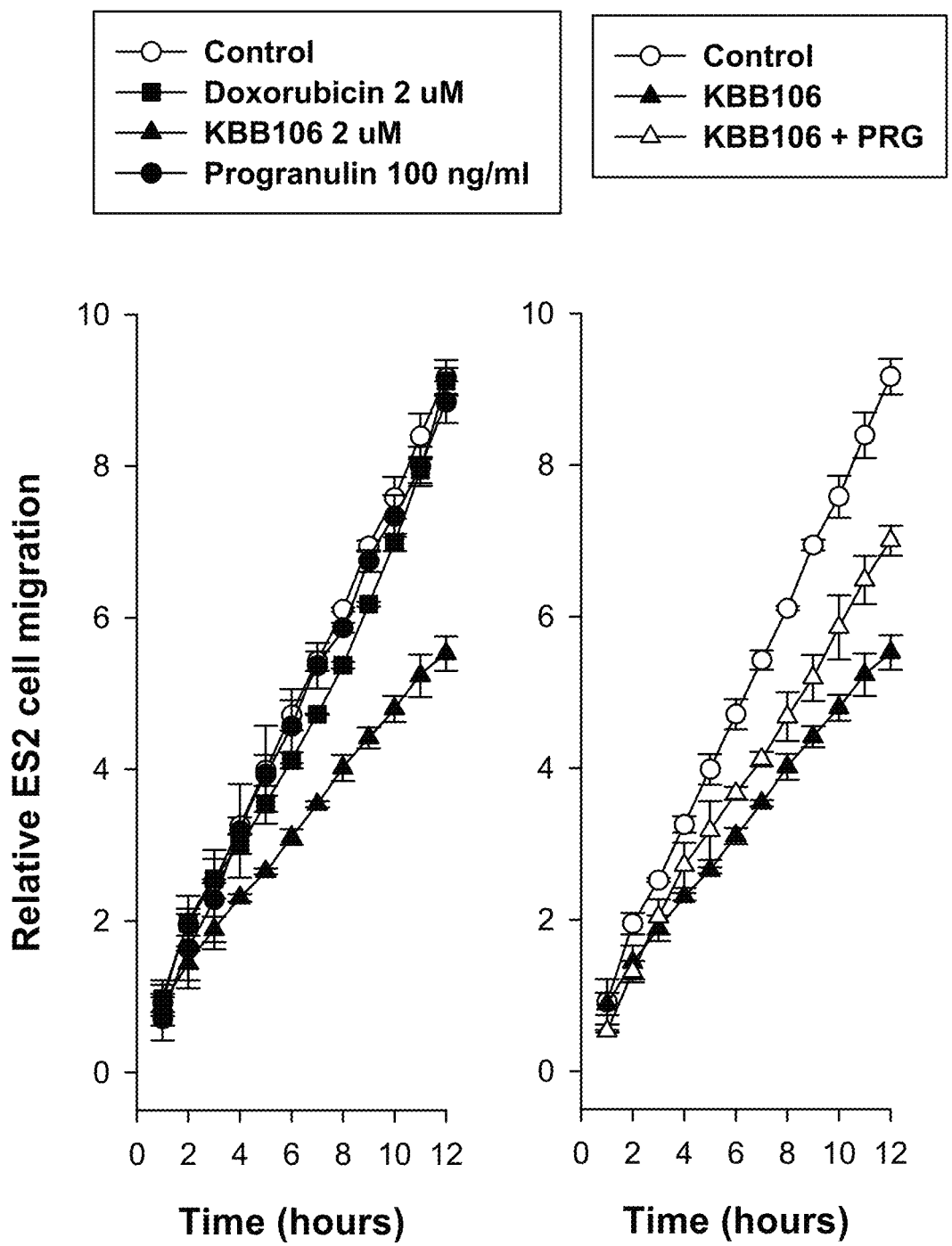

This second cellular assay was also used to screen the different Katana-drug conjugates (FIG. 15). As shown in FIG. 15A, ovarian (SKOV3 and ES-2) cancer cells were incubated for 2 hours with the Doxorubicin or conjugated Doxorubicin (KBB106) (2 µM), washed and then cell migration was performed. Results show that Katana-drug conjugates strongly affected the capacity of these cancer cells to migrate. For example, KBA-106 almost completely abolished the cellular capacity of these cells to migrate indicating that Katana-drug conjugates exert a strong effect against cancer invasion or dispersion of metastases. However, as shown in FIGS. 15B and 15C, when the cancer cells were incubated with conjugated Doxorubicin (KBB106) in the presence of a sortilin ligand (Neurotensin, Katana peptide or progranulin), the migratory effect of the Doxorubicin conjugate was reversed.

Surface plasmon resonance, apoptosis and migration results provided evidences that Katana-peptide and conjugate interact with or require the sortilin receptor. Interestingly, the sortilin receptor has been reported to be overexpressed in ovarian cancers as compared to normal ovarian tissue (FIG. 16A) (Hemmati 2009, Ghaemimanesh 2014). Sortilin was also shown to be expressed in various human solid tumours such as colon, prostate, pancreatic and lung. Furthermore, sortilin expression has been associated with the aggressiveness of breast cancer (Roseli, 2015). Here, it was also observed that this receptor is expressed in various human brain tumours from grade I to grade IV (FIG. 16B) and in various human ovarian cancers from grade I to grade IV (FIG. 16C). Overall, since sortilin is involved in the transport of Katana-peptide, these results indicate that Docetaxel-Katana peptide conjugates could target tumours which express the sortilin receptor.

Figure 17:
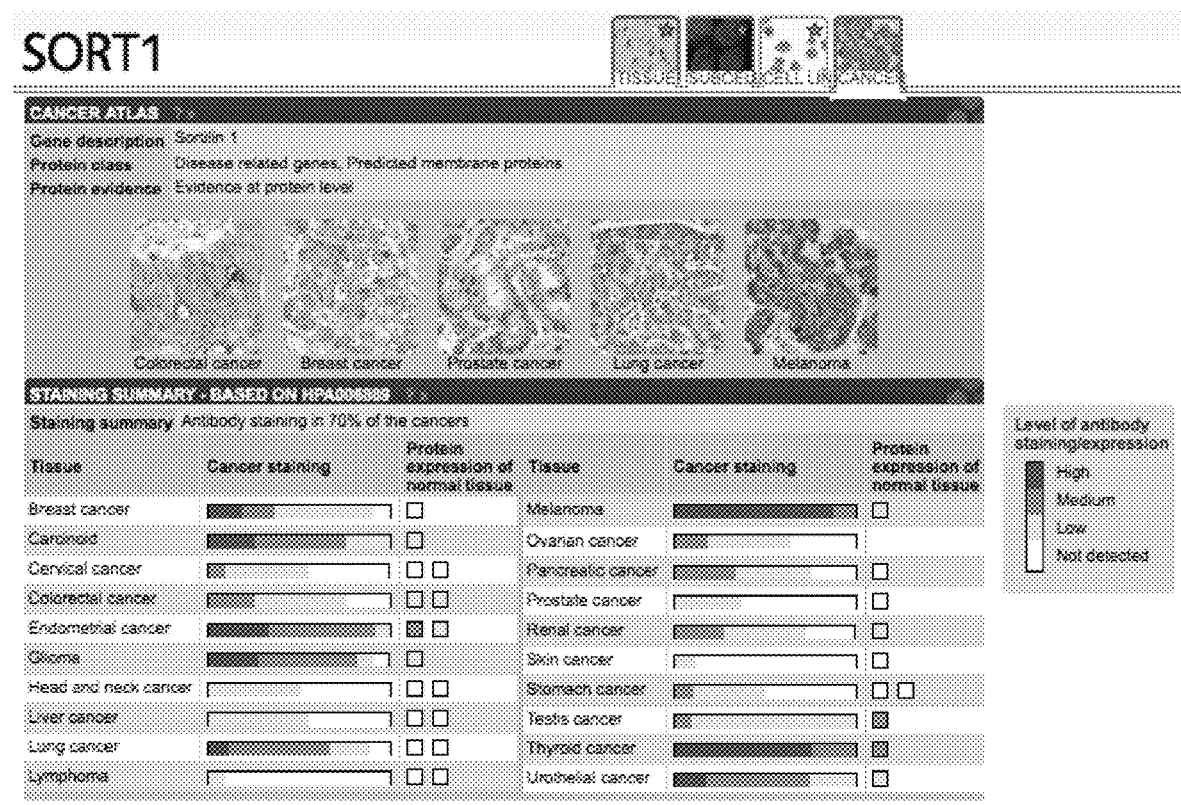
FIG. 17 is a prior art representation of sortilin (SORT1) expression in human cancers from the Human Protein Atlas website (http://www.proteinatlast.org).

In addition to these results on sortilin expression in ovarian and brain tumours, high levels of sortilin have been reported in various human cancers in the "Human protein atlas". FIG. 17, taken from the website http://www.protein-atlas.org/clearly demonstrates that high sortilin expression has been detected in biopsies of human cancers including melanoma, breast cancer, endometrial and lung cancers.

Example 4

In Vivo Effects of Conjugate Compounds

Figure 18:
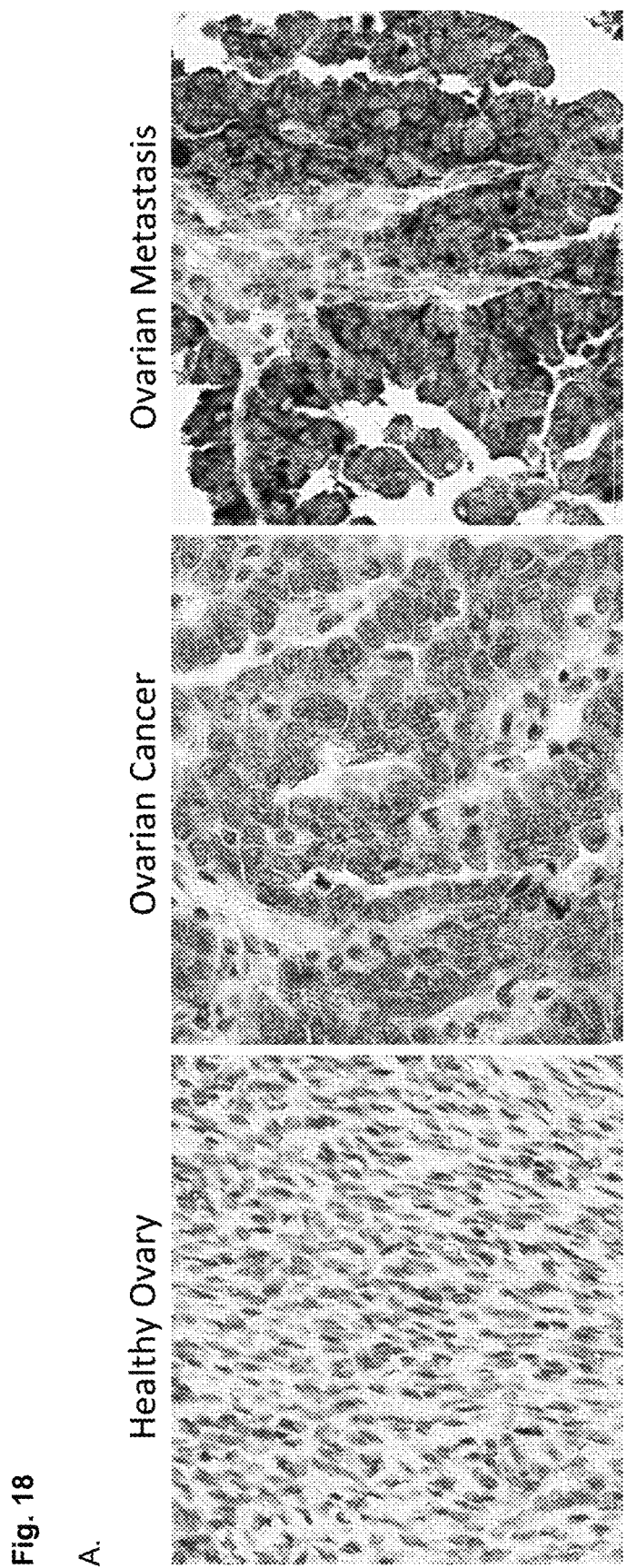
FIG. 18 shows the expression of sortilin in ovarian tissues by immunohistochemistry (IHC). 18A. Sortilin is overexpressed in primary ovarian tumor and in ovarian metastasis and almost undetectable in non-malignant healthy ovarian tissue. 18B. Sortilin was also detected by IHC in a series of normal ovarian tissue, benign tumors, borderline tumors, malignant tumors as well as in metastases from ovarian cancers. Results indicate that sortilin expression increased as a function of their malignant phenotypes and is higher in ovarian metastases.
Figure 18:
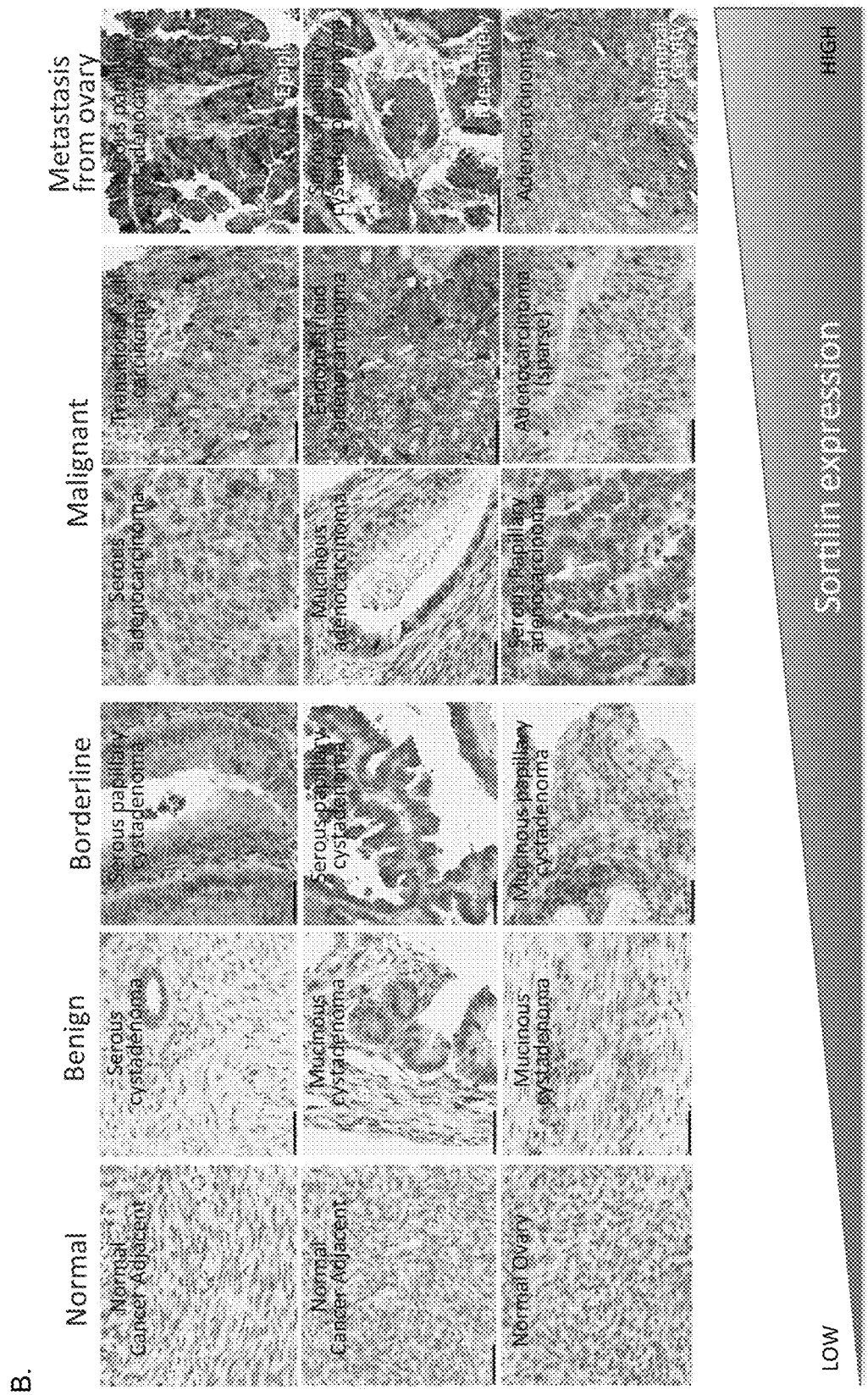

Sortilin is overexpressed in cancer tissue but nearly undetectable in health tissue. As demonstrated in FIGS. 18A and 18B, sortilin expression in tissues increases as a function of the malignant tissue phenotype. In particular, sortilin expression is higher in ovarian metastases.

a) Docetaxel

Figure 19:
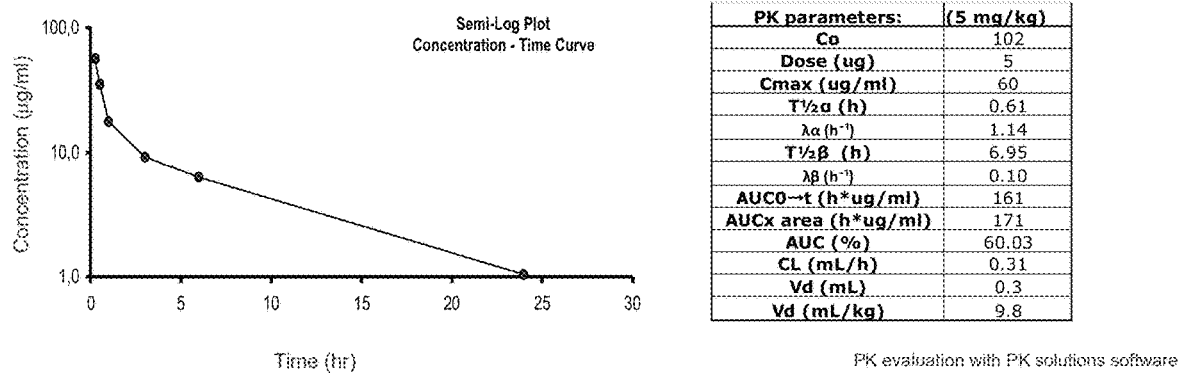
FIG. 19 is a representation of pharmacokinetics of the Docetaxel-Katana peptide conjugate (KBA-105). Mice were injected with radiolabeled conjugate at 5 mg/kg. Plasma was collected at different time points, radioactivity was counted and plasma levels were plotted as a function of time. Pharmacokinetic parameters were then extracted from the curve using the «PK solutions» software.
Figure 20:
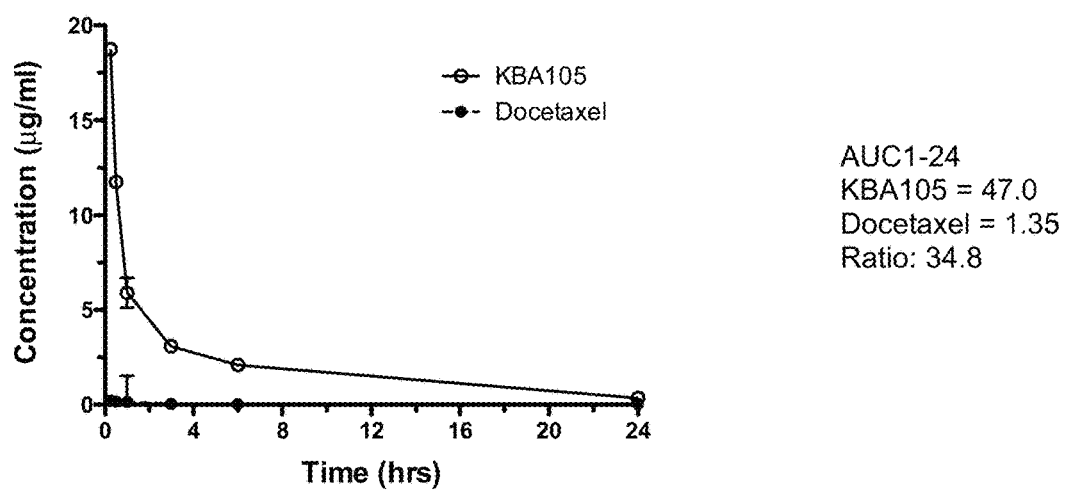
FIG. 20 is a graph showing concentration of unconjugated and conjugated Docetaxel as a function of time. Mice were injected iv with radiolabeled [$^3$H]-Docetaxel or radiolabeled [$^{125}$I]-KBA105 at an equivalent dose of Docetaxel (Docetaxel=2.2 mg/kg; KBA105=5 mg/kg). Plasma samples were collected at different time points and radioactivity quantified. Results are expressed in terms of KBA105 or Docetaxel concentration in plasma as a function of time. Area under the curve for the time period (AUC1-24) was estimated for KBA105 and Docetaxel using GraphPad Prism software. Ratio between AUC1-24 for KBA105 and Docetaxel was calculated to be around 35.

To evaluate the impact of the drug conjugation to Katana Biopharma peptide on drug pharmacokinetics and tissue distribution, mice were injected with [$^{125}$I]-Docetaxel-Katana peptide conjugate. Plasma was collected at different times (FIG. 19A). Radioactivity associated with plasma was quantified and pharmacokinetic parameters were determined. As indicated in the FIG. 19, the half-life of the conjugated Docetaxel is 6 hours. This plasmatic half-life is significantly higher than the 1 hr half-life reported in the literature for free Docetaxel (Assessment report for Docetaxel Teva from the European Medicines Agency). In FIG. 20, plasma concentration of Docetaxel-Katana peptide conjugate was compared to that of unconjugated Docetaxel after iv bolus injection. Results indicate a much higher area under the curve for the Docetaxel-Katana peptide conjugate compared to that of unconjugated Docetaxel.

Figure 21:
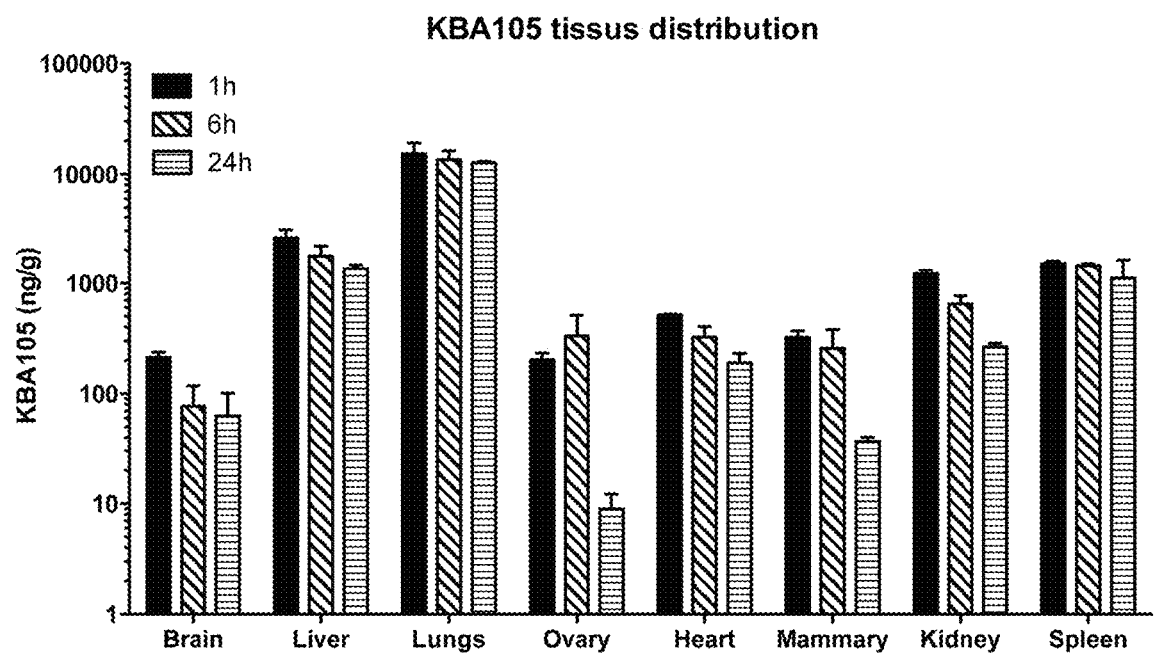
FIG. 21 shows the tissue distribution of [$^{125}$I]-Katana peptide-Docetaxel. CD-1 mice were injected with the radiolabeled conjugate at 5 mg/kg via iv bolus injections (21A) or 2.2 mg of radiolabeled Docetaxel (21B). At the indicated times (1 h, 6 h, 24 h) mice were sacrificed and perfused with saline for 8 min. Tissues were then collected and radioactivity was measured. Results are expressed in terms of ng/g of tissue.
Figure 21:
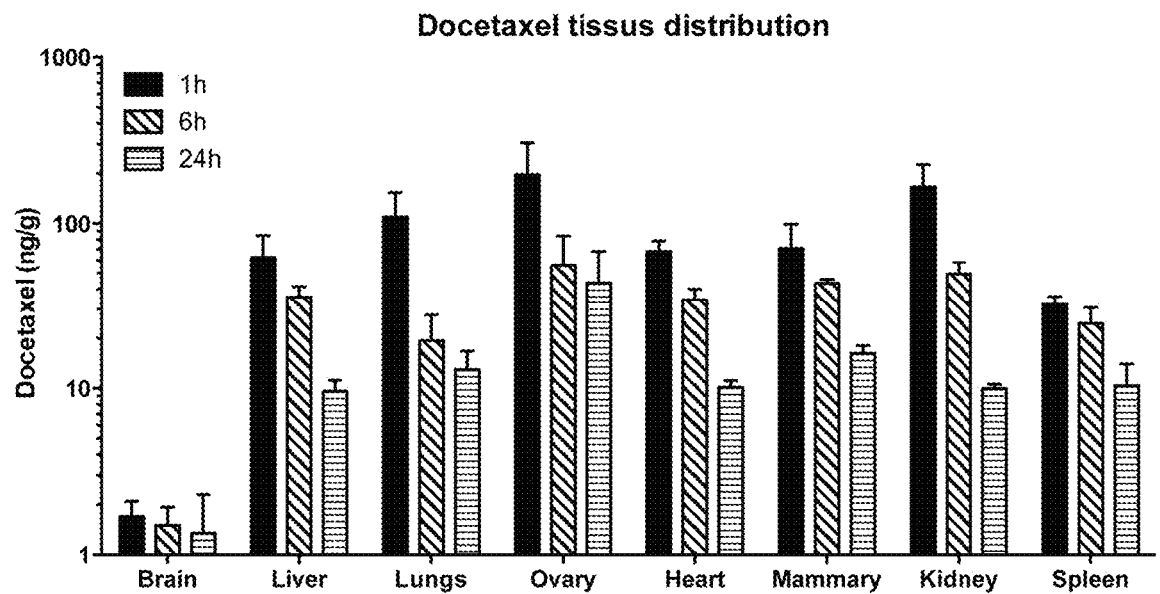

For tissue distribution, radiolabeled Katana-drug conjugate (KBA-105) and Docetaxel were administered by iv bolus injections at an equivalent dose of Docetaxel (FIG. 21). At the indicated times (1, 6 and 24 hours), whole body perfusion was performed for 8 min with saline at a flow rate of 8 ml/min after 2, 6 and 24 hours iv bolus injections. Tissues were then collected and the radioactivity quantified and levels of the radiolabeled conjugate (KBA-105) were quantified. Results show high accumulation of the conjugate in the lung, liver, spleen and kidney tissues. Furthermore, levels measured for KBA-105 were higher than those of Docetaxel in most tissues. To further characterize the difference in levels of both radiolabeled compounds, AUC1-24 values were calculated for the different tissues and compared in Table 5. AUC1-24 ratio between KBA-105 and Docetaxel indicate that the Katana-drug conjugates could accumulate in higher levels than unconjugated Docetaxel.

TABLE 5

Area under the curve (AUC1-24) for radiolabeled Docetaxel and Katana-drug conjugate (KBA-105) from FIG. 21 tissue distribution results.

| Tissue | Docetaxel (ng-hr/ml) | KBA105 (ng-hr/ml) | Estimated Docetaxel (ng-hr/ml) | Ratio KBA105/ Docetaxel | Ratio (Estimated Docetaxel/ Docetaxel) |
|---|---|---|---|---|---|
| Brain | 34 | 1643 | 723 | 48.3 | 21.3 |
| Liver | 652 | 39058 | 17186 | 60 | 26.4 |
| Lung | 614 | 309075 | 135993 | 500 | 221 |
| Ovary | 1523 | 2431 | 1070 | 1.6 | 0.7 |
| Heart | 656 | 6754 | 2972 | 10.3 | 4.5 |
| Mammary | 823 | 2719 | 1196 | 3.3 | 1.5 |
| Kidney | 1072 | 12911 | 5681 | 12.0 | 5.3 |
| Spleen | 457 | 25911 | 11401 | 24.9 | 25.0 |

To further evaluate the in vivo efficacy of the Katana-drug conjugate, SKOV3 cancer cells expressing luciferase were implanted in the mouse flank. Mice with similar tumours were treated with either Docetaxel or the Katana-drug conjugate KBA-105 at an equivalent dose of Docetaxel (10 mg/kg/week). Mice treated with Docetaxel received 3 treatments and mice treated with KBA-105 received 5 treatments. Tumour imaging was performed on different days by injecting the luciferase substrate luciferin and by using the Xtreme imaging system from Carestream.

Figure 22:
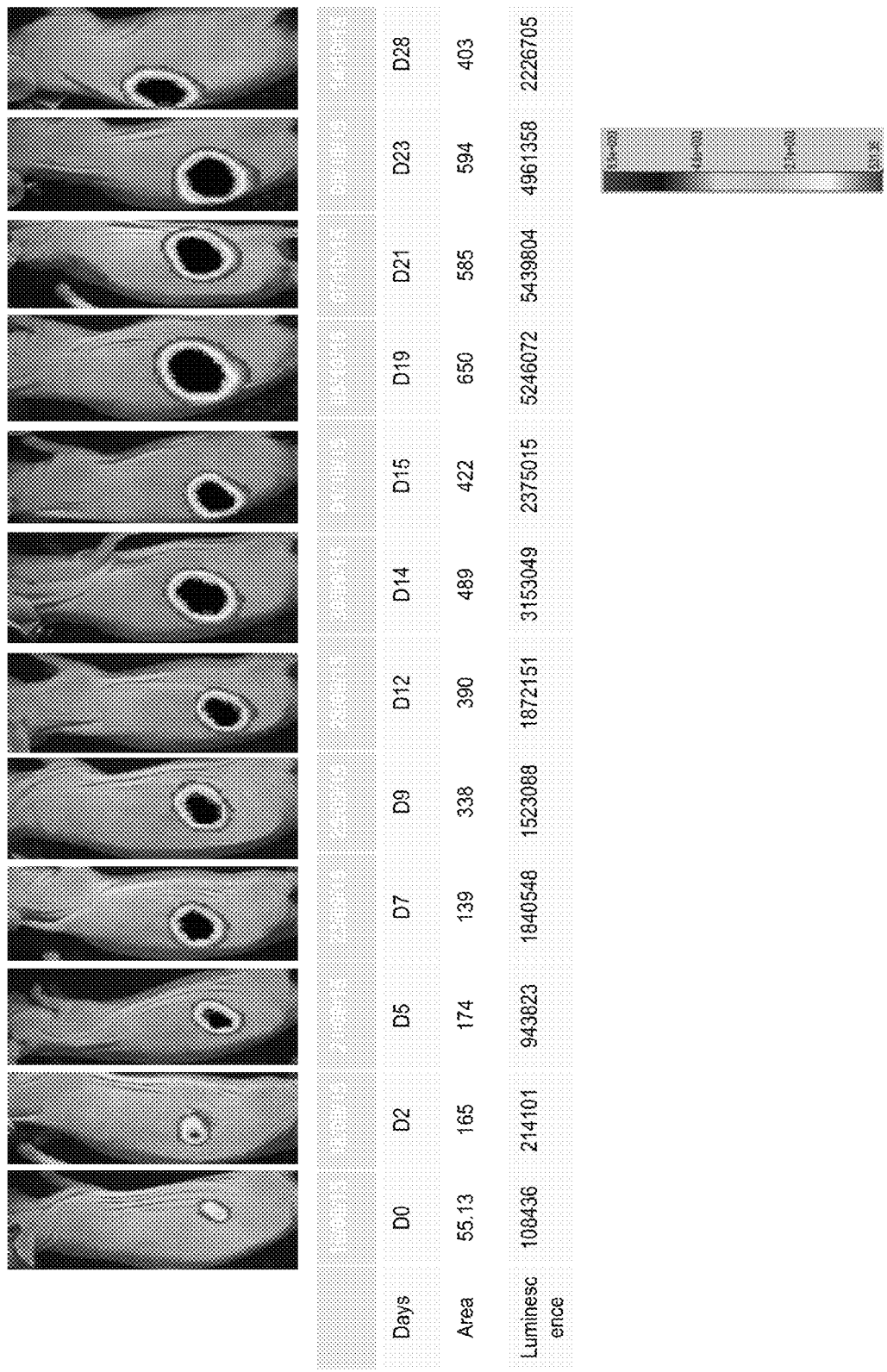
FIG. 22 shows the effect of KBA105 and Docetaxel on ovarian subcutaneous tumors. Mice were implanted in the flank with SKOV3 cancer cells. Tumor growth was monitored by luminescence using the Near Infrared imaging system from Carestream. When tumors reached similar luminescence, mice were treated with Docetaxel (22A) or KBA105 (22B) at an equivalent dose of Docetaxel (10 mg/kg/week).
Figure 22:
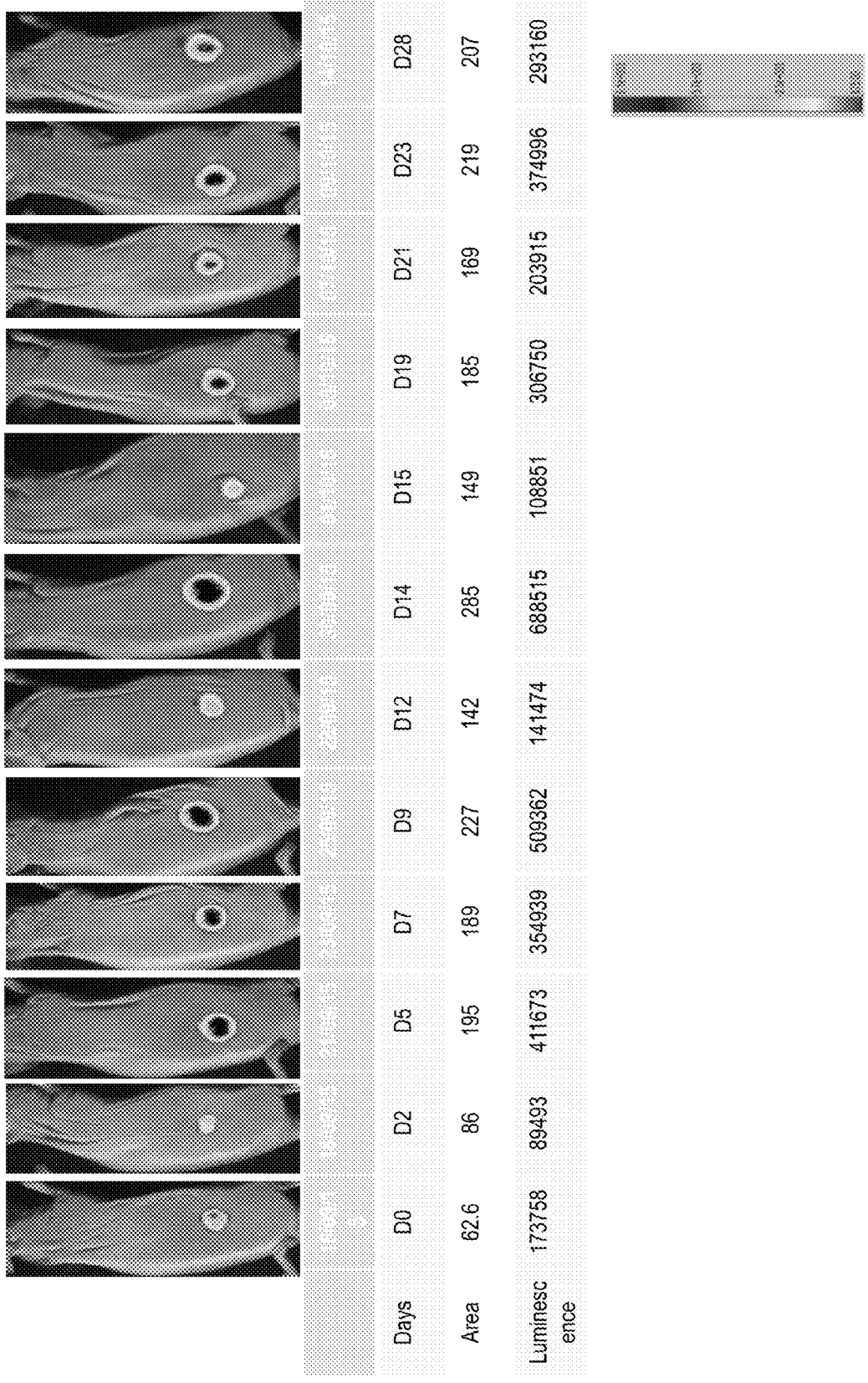
Figure 23:
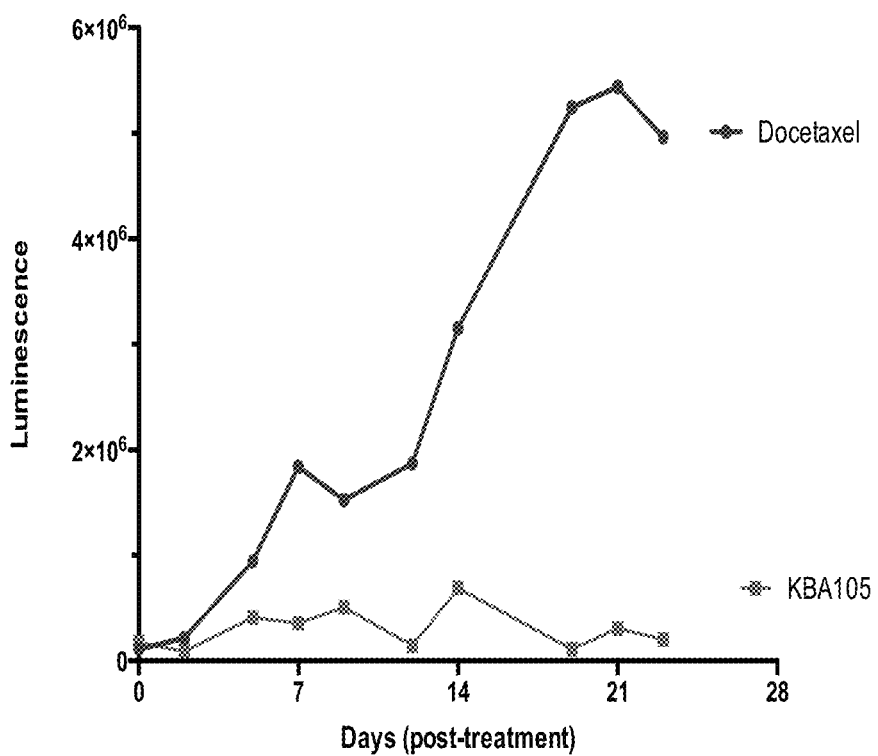
FIG. 23 shows the luminescence quantitation of FIG. 22. Results are expressed in terms of luminescence intensity as a function of post-treatment days.
Figure 24:
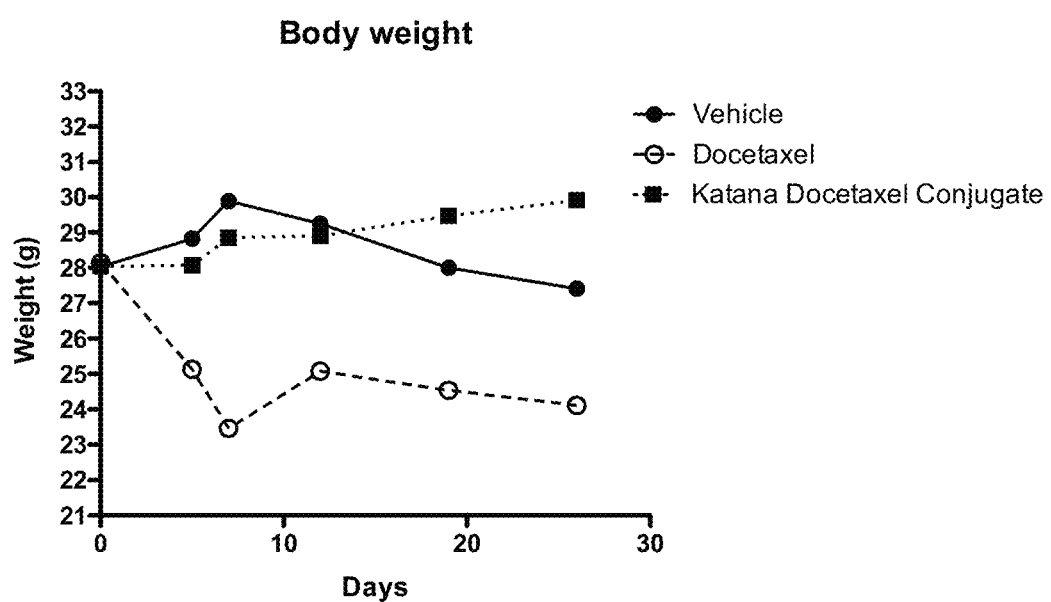
FIG. 24 is a graph showing the body weight of mice treated with Docetaxel and KBA105 monitored over treatment days. Results indicate that at the dose administered Docetaxel has a strong effect on the body weight. In contrast, at the equivalent dose of Docetaxel, KBA105 has no effect on the body weight of mice. These results indicate that at an equivalent dose of Docetaxel, KBA105 is better tolerated.

Imaging results in FIG. 22 show a much lower luminescence on different days for the mouse treated with KBA-105 compared to the one treated with Docetaxel. Luminescence was then quantified and plotted as a function of days after implantation (FIG. 23). These early-quantitated luminescence results suggest that KBA-105 could be more efficacious than unconjugated Docetaxel to reduce tumour growth in this ovarian animal tumour model. Mice treated with Docetaxel had a body weight loss close to 20% (FIG. 22A) whereas the body weight of mice treated with KBA-105 was still unaffected by the treatments at 20 mg/kg/week (FIG. 22B). Furthermore, body weight of mice treated after 5 treatments with KBA-105 was unaffected (FIG. 24) whereas the mice treated at an equivalent dose of Docetaxel was strongly affected after only 3 treatments.

b) Doxorubicin

Figure 25:
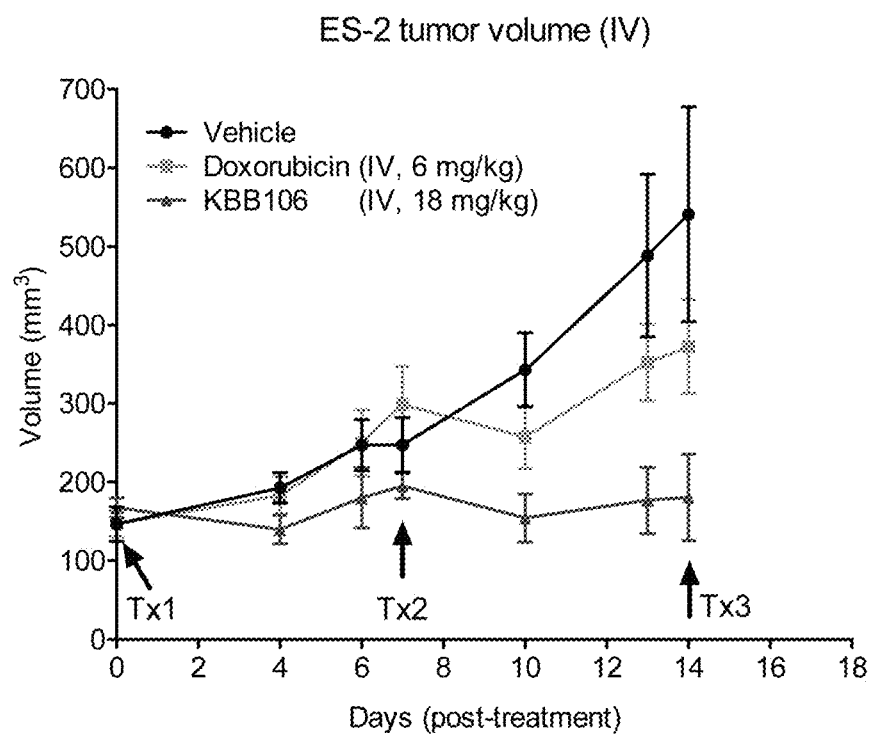
FIG. 25 shows the effect of the Doxorubicin conjugate (KBB106) and unconjugated Doxorubicin on ovarian subcutaneous tumors. 25A. Mice were implanted in the flank with ES-2 ovarian cancer cells. Tumor growth was measured using a caliper. When tumors reached a tumor volume of about 150 mm$^3$, mice were treated with Doxorubicin or KBB106 at an equivalent dose of Doxorubicin (6 mg/kg/week). 25B. Results show tumor volume increase at Day 14 post-treatment in mice treated with Doxorubicin or KBB106 compared to the vehicle group. 25C. Because of KBB106 efficacy and tolerability, treatments of mice with the conjugate were continued up to Day 66 post-treatment.
Figure 25:
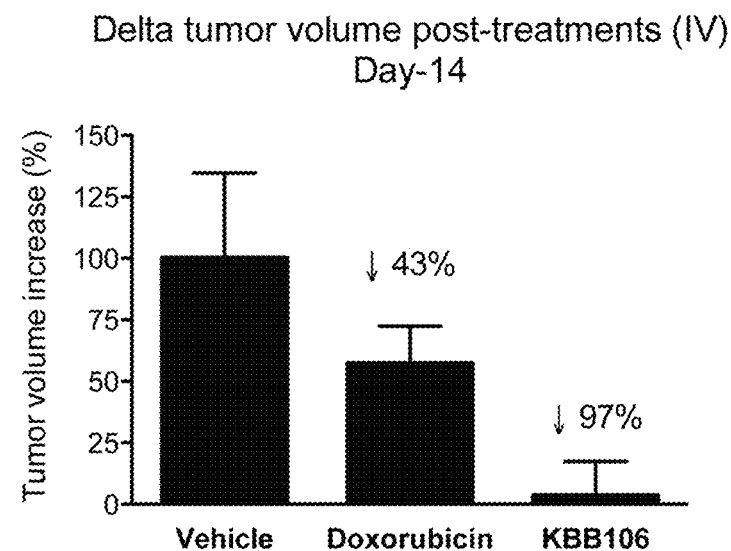
Figure 25:
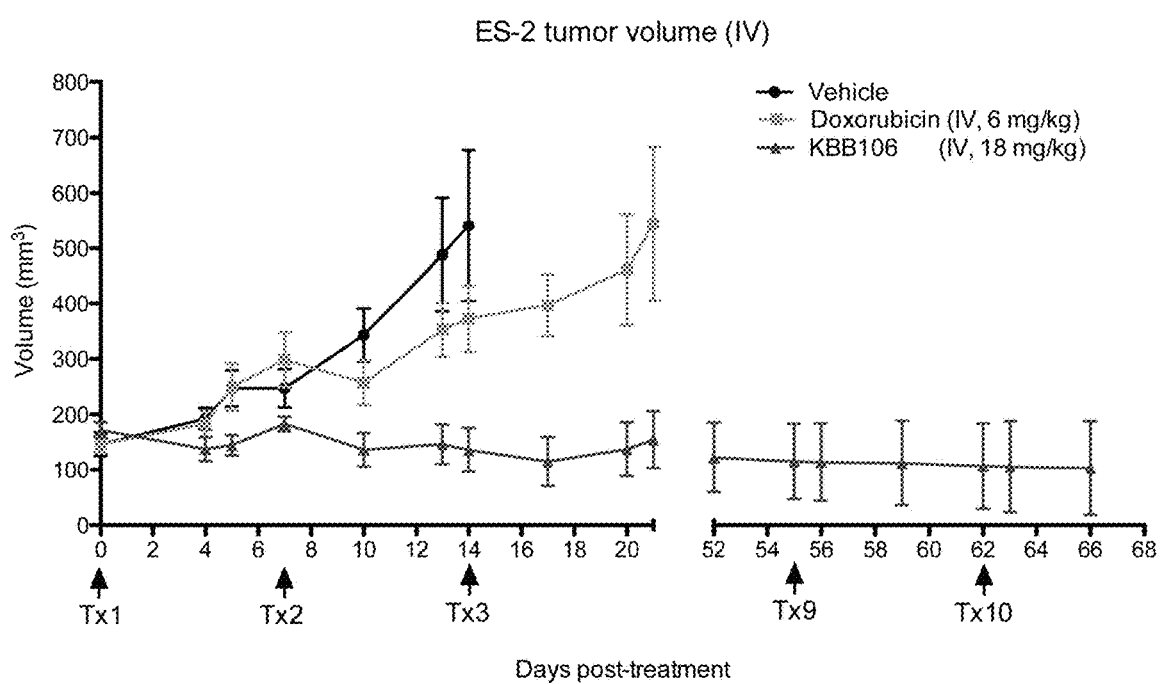
Figure 26:
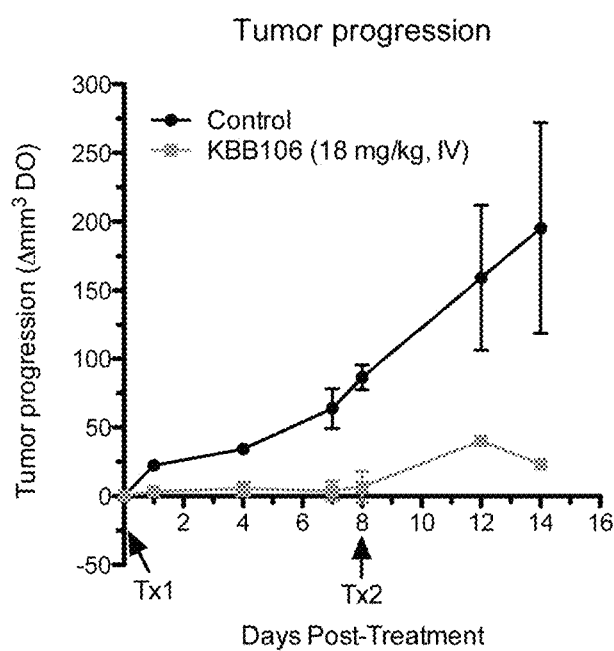
FIG. 26 shows the effect of the Doxorubicin conjugate (KBB106) on ovarian subcutaneous tumors. 26A. Mice were implanted in the flank with SKOV3 ovarian cancer cells. When tumors reached a volume of about 150 mm$^3$, mice were treated with KBB106 (18 mg/kg/week) as indicated by the arrows. Results show tumor volume progression (initial tumor volume at D0 was subtracted) in mice treated with KBB106 compared to the vehicle group. 26B. Body weight of mice was monitored during the treatments. Absence of body weight loss in mice treated with KBB106 suggests the treatments were well tolerated.
Figure 26:
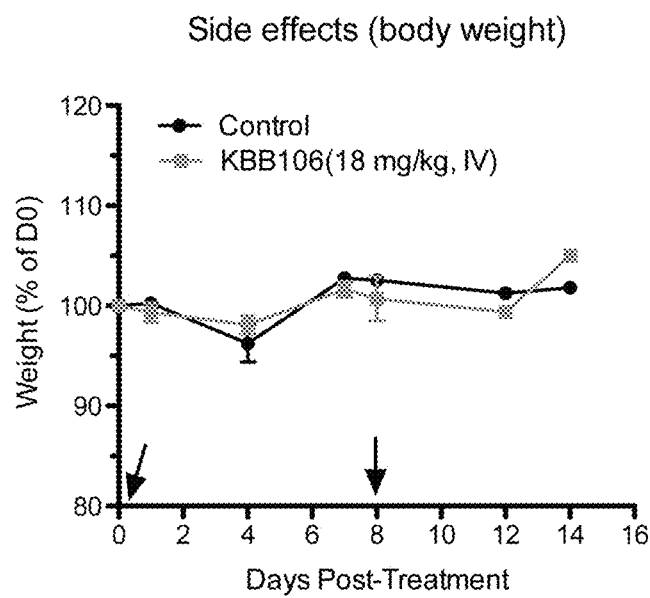

The effect of the conjugated and unconjugated Doxorubicin was also evaluated on ovarian subcutaneous tumors. Mice were implanted in the with ES-2 ovarian cancer cells. Tumor growth was measured using a caliper. When tumors reached a tumor volume of about 150 mm$^3$, mice were treated with Doxorubicin or Katana-Doxorubicin conjugate KBB106 at an equivalent dose of Doxorubicin (6 mg/kg/week). The results show that in mice treated with KBB106, the tumor volume remained about the same following the first treatment however in the mice treated with Doxorubicin, the tumor volume increased following the first treatment (FIG. 25A). Similarly, as demonstrated in FIG. 25B, the tumor volume decreased by 97% in KBB106 treated mice compared to the vehicle group compared to a decrease of 43% in Doxorubicin treated mice compared to the vehicle group. Progression of SKOV3 xenograft tumors in KBB106 treated mice was also significantly decreased compared to the control group (FIG. 26A).

Not only was tumor size suppression more effective with conjugated Doxorubicin, the tolerability of conjugated Doxorubicin was also superior to that of unconjugated Doxorubicin. In FIG. 25C, it is shown that treatment with KBB106 was continued up to Day 66 post-treatment. Moreover, treatment with KBB106 had little effect on the body weight of the mice (FIG. 26B) thus indicating that treatment with conjugated Doxorubicin is well tolerated.

Figure 27:
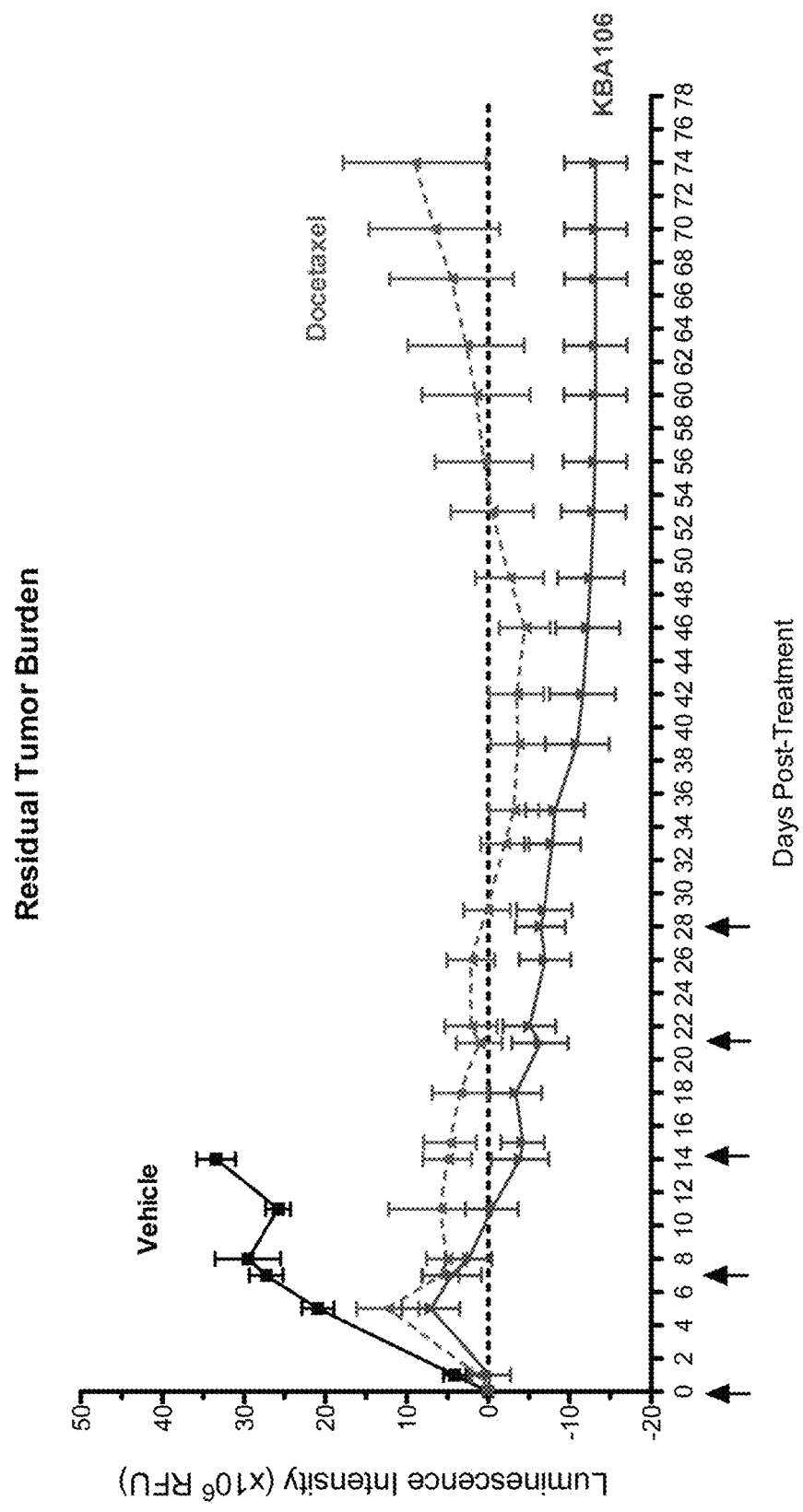
FIG. 27 shows the effect of the Docetaxel conjugate (KBA106) and unconjugated Docetaxel on breast subcutaneous tumors. 27A. Mice were implanted in the flank with MDA-MB231 breast cancer cells expressing luciferase. Tumor growth by luminescence was visualized using an in vivo imaging system from Carestream. Mice were treated with vehicle, Docetaxel (15 mg/kg/week) or KBA106 (50 mg/kg/week). Initial luminescence intensity was subtracted. 27B. Results show the residual tumor burden evaluated by the remaining luminescence associated with cancer cells at Day 74. No value was available (N/A) for the mice treated with the vehicle since all mice were then sacrificed because the size of their tumors reached the endpoint limit. 27C. Tumor luminescence results were expressed in terms of percentage of progression on D74 post-treatment compared to initial tumor luminescence. In the Docetaxel group, the tumor luminescence increased by 100% whereas in the KBA106 treated group the luminescence decreased by 100%. In the KBA106 group, no luminescence was detectable on Day 74 post-treatment suggesting no residual tumors in these mice.
Figure 27:
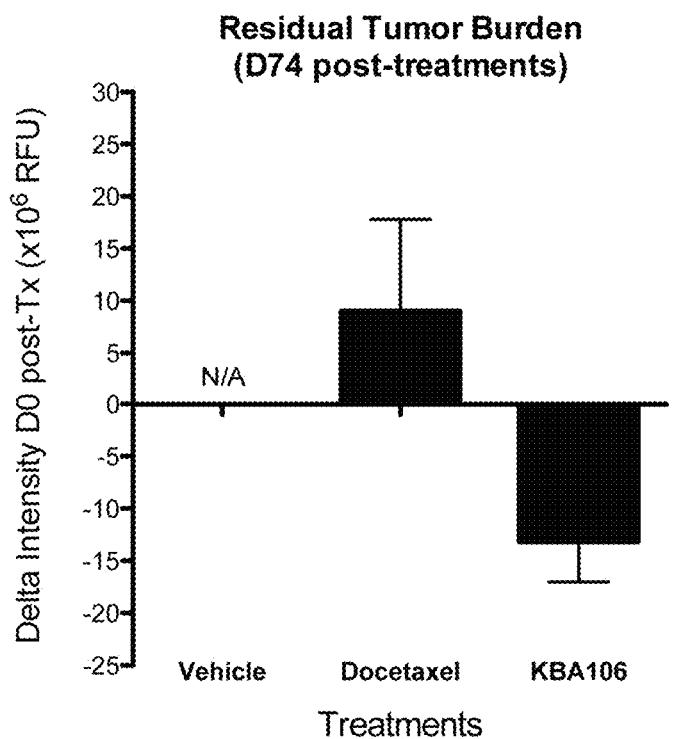
Figure 27:
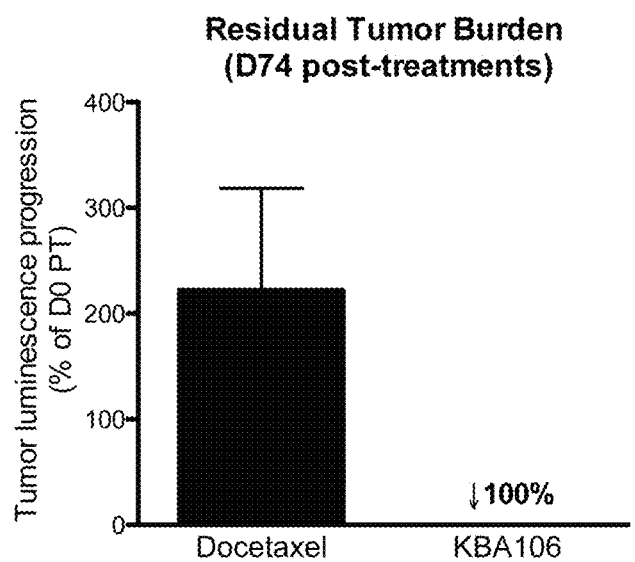

Residual tumor burden was assessed in Docetaxel and Docetaxel conjugate treated mice (FIG. 27). Mice were implanted in the flank with MDA-MB231 breast cancer cells expressing luciferase. Tumor growth by luminescence was visualized using an in vivo imaging system from Carestream. Mice were treated with vehicle, Docetaxel (15 mg/kg/week) or KBA106 (50 mg/kg/week). After 74 days post treatment, no luminescence was detectable in Docetaxel conjugate treated mice (FIGS. 27B and 27C), thus suggesting no residual tumors in the mice.

c) Curcumin

Figure 28:
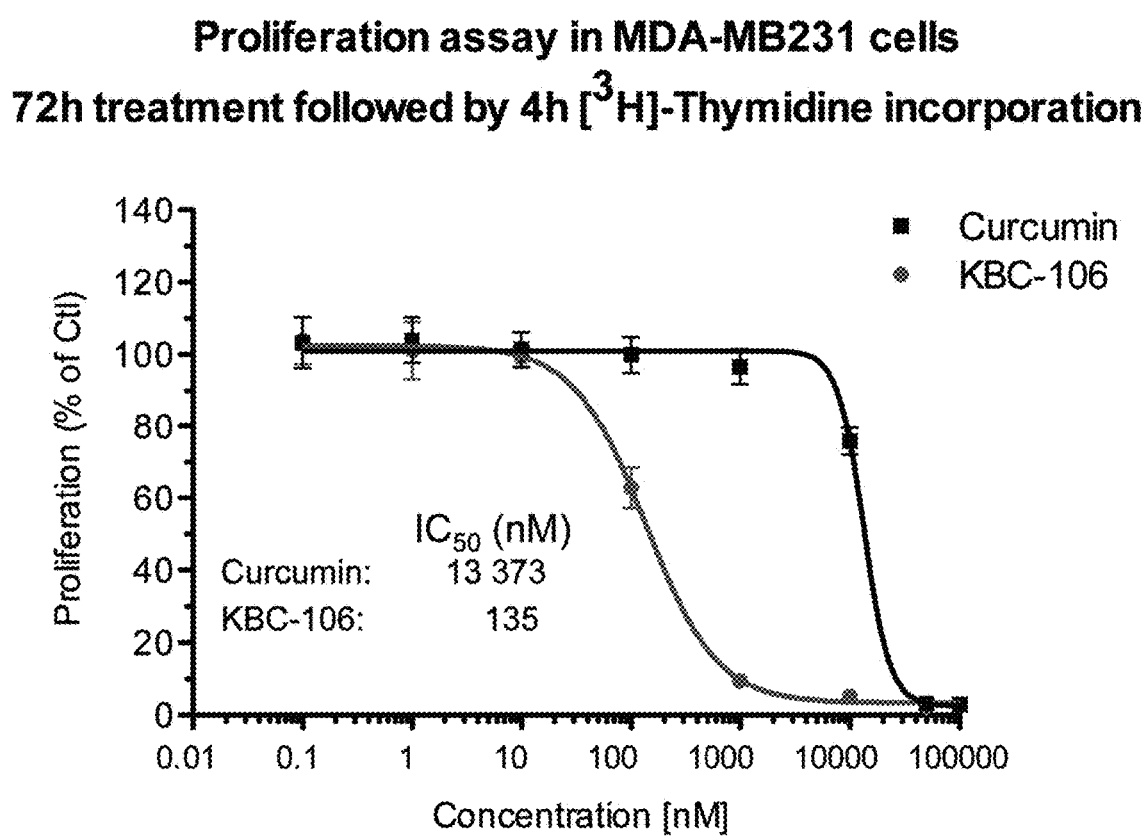
FIG. 28 shows the effect of the Curcumin conjugate (KBC106) and unconjugated Curcumin on cancer cell proliferation. Breast cancer cells (MDA-MB231) were incubated with increasing concentrations of KBC106 or curcumin. After 72 hrs, thymidine incorporation assay was performed to assess the anti-proliferative properties of both molecules. IC50 values were extracted from the anti-proliferative curves. Results show that KBC106 has a stronger anti-proliferation activity (about 100-fold) against these breast cancer cells compared to unconjugated curcumin.

The phytochemical Curcumin, unconjugated and conjugated, was also tested on cancer cell proliferation (FIG. 28). Breast cancer cells (MDA-MB231) were incubated with increasing concentrations of KBC106 or curcumin. After 72 hrs, thymidine incorporation assay was performed to assess the anti-proliferative properties of both molecules. IC50 values were extracted from the anti-proliferative curves. As shown in FIG. 28A, KBC106 had a stronger anti-proliferation activity (about 100-fold) against these breast cancer cells compared to unconjugated curcumin. Proliferation assay was also performed using different types of cancer cells (ovarian, breast, skin and colorectal cancer cells). IC50 values were calculated from the anti-proliferation curves. In all cases, the Curcumin conjugate (KBC106) had stronger anti-proliferative activity (9-100 fold) than unconjugated Curcumin, as shown in Table 6 below.

TABLE 6

Anti-proliferative IC50 values of conjugated and unconjugated Curcumin

| Cancer | Cell lines | Curcumin IC50 (nM) | KBC106 IC50 (nM) | Potency (x-fold) |
|---|---|---|---|---|
| Ovary | ES-2 | 14 433 | 1 524 | 10 |
| Breast | MDA-MB231 (Triple negative) | 13 373 | 135 | 100 |
| | HCC-1569 (HER2+; Herceptin resistant | 14 750 | 1 011 | 15 |
| | HCC-1954 (HER2+; Lapatinib resistant) | 11 989 | 1 286 | 9 |
| Skin | SK-MEL-28 | 12 454 | 243 | 51 |
| | A-375 | 20 889 | 326 | 64 |
| Colorectal | HT-29 | 51 287 | 3 605 | 14 |

Figure 29:
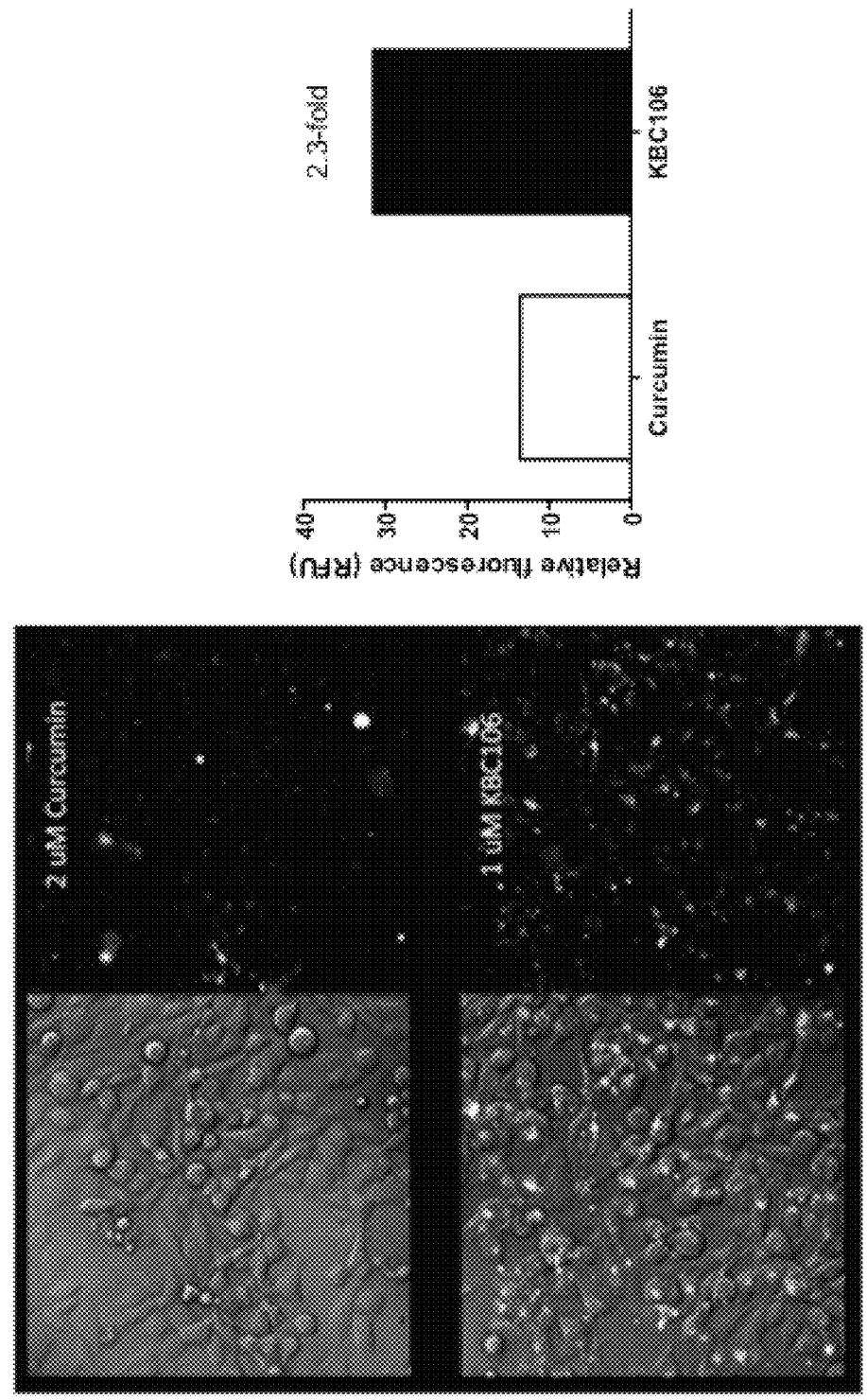
FIG. 29 shows the preferential sortilin dependent uptake of Curcumin conjugate (KBC106) in ES-2 ovarian cancer cells. A. Cancer cells were incubated with KBC106 or curcumin. Uptake for both molecules was evaluated by fluorescent live imaging. Higher accumulation of fluorescence was detected for KBC1006 indicating a better cell internalization for the conjugate. B. Uptake of KBC106 was monitored by in vitro fluorescence imaging in the presence of sortilin ligands Neurotensin (NT) and progranulin as well as free Katana peptide. Accumulation of KBC106 in ovarian cancer cells was inhibited by sortilin ligands. C. Results of KBC106 accumulation were expressed in terms of KBC106 fluorescence intensity in the presence or absence of sortilin ligands. Data demonstrate pharmacological competition of KBC106 uptake by sortilin ligands.
Figure 29:
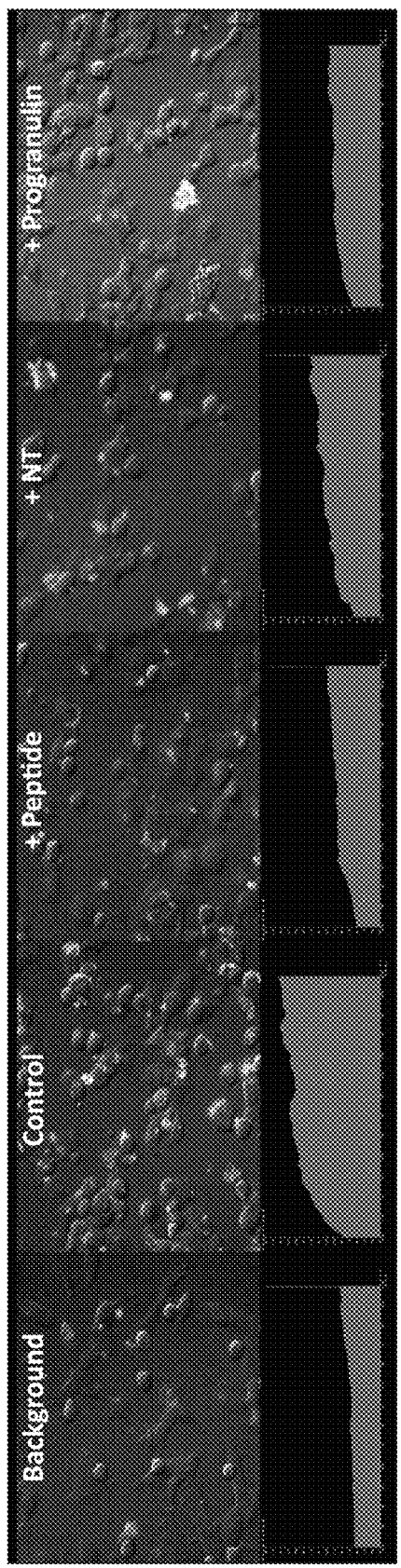
Figure 29:
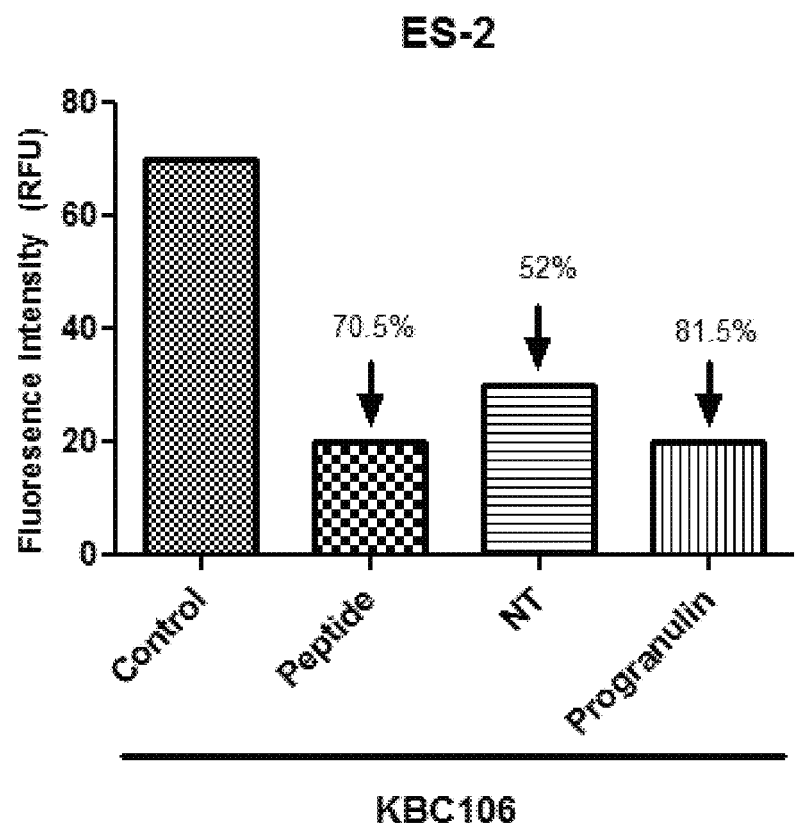

As demonstrated herein, the Curcumin conjugate (KBC106) cellular uptake is sortilin dependent. As shown in FIG. 29A, cancer cells incubated with conjugated or unconjugated Curcumin were assessed for uptake for both molecules using fluorescent live imaging. It was found that cells had increased cellular internalization of conjugated Curcumin as opposed to unconjugated Curcumin. In addition, it was shown that sortilin ligands (Neurotensin, progranulin and free Katana peptide) inhibit cellular update of conjugated Curcumin (FIGS. 29B and 29C).

In FIG. 30, it was further evaluated whether the Curcumin conjugate (KBC106) induces cancer cell apoptosis. Cancer cells were incubated with KBC106 and curcumin. First column, uptake for both molecules can be monitored by fluorescent microscopy. Higher accumulation of fluorescence was detected for KBC1006 indicating a better cell internalization for the conjugate. Curcumin accumulation was barely visible in these cancer cells. In the second column, Alpha-tubulin was detected by fluorescence and images indicating that KBC106 strongly affects cancer cell microtubules whereas curcumin alone has little effect on them. In the third column, cell nucleus was labelled with the fluorescent dye DAPI. In contrast to unconjugated Curcumin, the KBC106 clearly induced the nucleus fragmentations showing that the conjugate induces apoptosis of cancer cells whereas Curcumin alone does not. The last column (Merge) shows that KBC106 fluorescence co-localized with the alpha-tubulin detection.

Figure 31:
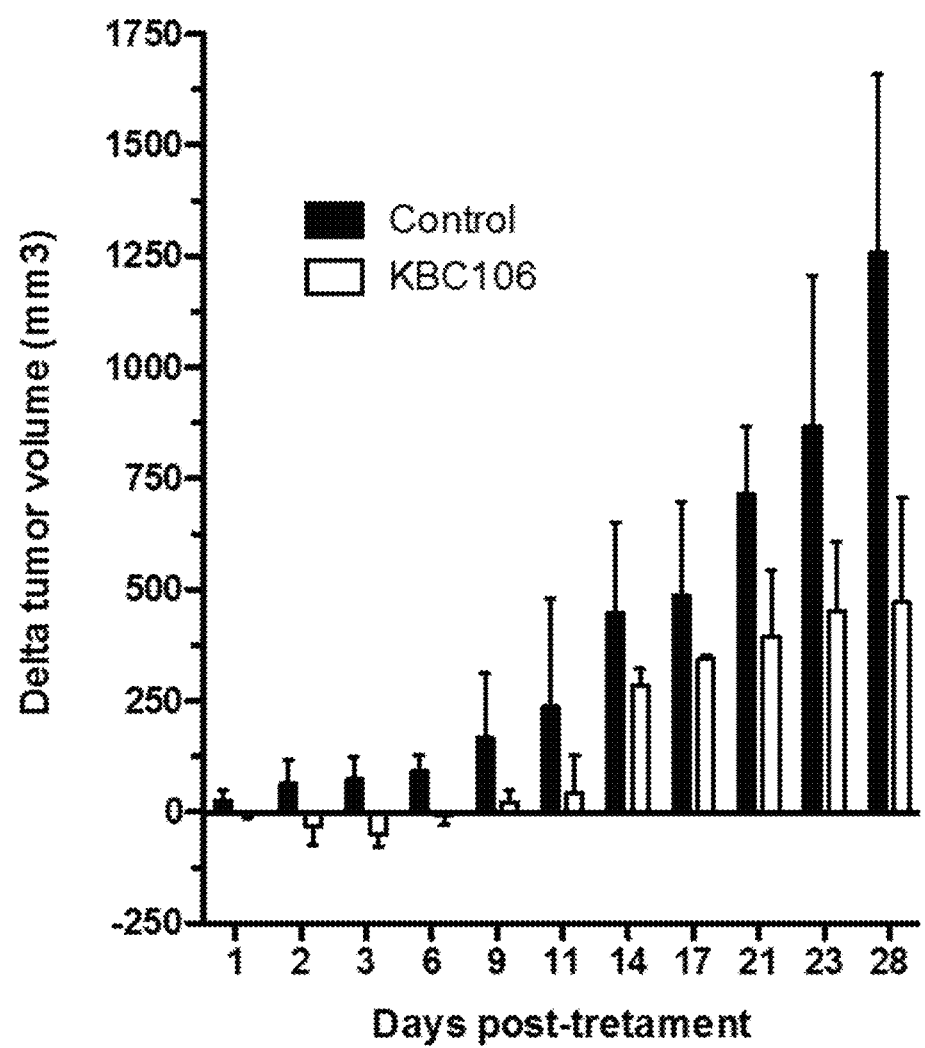
FIG. 31 is a demonstration that the Curcumin conjugate (KBC106) inhibits tumor growth of endometrial (MES) subcutaneous tumors. Mice were implanted in the flank with endometrial (MES) cancer cells. Tumor growth was measured using a caliper. When tumors reached a volume of around 150 mm$^3$, mice were treated with KBC106 at 60 mg/kg/twice a week.

The Curcumin conjugate (KBC106) was also shown to have an inhibitory effect on endometrial cancer growth (FIG. 31). Mice were implanted in the flank with endometrial (MES) cancer cells. Tumor growth was measured using a caliper. When tumors reached a volume of around 150 mm$^3$, mice were treated with KBC106 at 60 mg/kg/twice a week. The results at Day 28 post-treatments show that KBC1006 inhibits tumor growth by about 62% compared to the vehicle group, as shown in Table 7.

TABLE 7

Inhibitory effect of KBC106 on endometrial tumor growth at day 28

| | At day 28 | |
|---|---|---|
| | Volume (mm$^3$) | Inhibition (%) |
| Control | 1258 | — |
| KBC106 | 473 | 62 |

In conclusion, the results describe new applications for drug-Katana peptide conjugates including anticancer drugs (small molecules, biologics such as mAbs) and phytochemicals. These anticancer drug conjugates remain active in vitro as evidenced upon efficient inhibition of cell proliferation, and induction of cell toxicity. Importantly, data obtained with Katana peptide conjugates indicate that the conjugation of anticancer drugs to the Katana peptide allows them to escape from P-gp action. Moreover, these results suggest that conjugation of anticancer drugs or phytochemicals to Katana peptides increases their efficiency in vivo by: 1) targeting receptors expressed or overexpressed in cancer cells such as sortilin and therefore will potentially reduce the side effects of the conjugated drugs, 2) bypassing the P-gp efflux pump and/or 3) by modifying the pharmacokinetics or bioavailability of the therapeutic drug. In fact, for example the conjugation of the anticancer drug docetaxel to the Katana peptide increases the half-life of the free drug by about 1 hour to about 6 hours. In addition, by specifically targeting receptor(s), Katana-drug conjugates are better tolerated compared to unconjugated drugs at an equivalent dose as observed in the in vivo study with KBA-105 and KBB106. Taken together, data described in the present disclosure suggest that anticancer drugs and phytochemicals conjugated to Katana peptide(s) may be used against primary tumours such as ovarian, breast, lung and skin cancers. In particular, these conjugates may be used against cancers involving expression or overexpression of sortilin. In addition, because P-gp efflux pump can limit the accumulation of potential effective drugs in other diseases, conjugation to the Katana peptide may potentially be used in indications outside of oncology. Furthermore, Katana peptides may be conjugated to other types of molecules including anticancer peptides, larger biologics (ex. monoclonal antibodies), siRNA as well as drug delivery systems such as nanoparticles and liposomes.

Example 5

Cell Proliferation Assay

Cancer cells were cultured in 96-well white plates (Perkin Elmer). They were synchronized for 24 hours in serum-deprived medium. After incubation of cells with unconjugated drugs (docetaxel, cabazitaxel, doxorubicin) or with drug-Katana peptide conjugates for 2 or 3 days, all media was aspirated and cells were pulse-labeled for 4 hours at 37° C./95% $O_2$/5% $CO_2$ with media containing 2.5 µCi/mL [methyl-$^3$H] thymidine (Perkin Elmer). Cells were washed, fixed, and dried before addition of scintillation fluid (Microscint 0, Perkin Elmer). After 24 hours, cell-associated tritium was quantified by counting on a plate reader (TopCount, Perkin Elmer). Incorporated [$^3$H] thymidine was plotted for each drug concentration.

Example 6

Cell Migration Assay by xCELLigence Biosensor System

Experiments were carried out using the Real-Time Cell Analyser (RTCA) Dual-Plate (DP) Instrument, the xCELLigence system (Roche Diagnostics, QC). This system was used according to the instructions of the supplier. Then, cells (25 000 cells/well) were seeded in serum-free medium onto a CIM-Plates 16 (Roche diagnostics). These plates are similar to conventional Transwells (8-μm pore size) with gold electrode arrays on the bottom side of the membrane, which provide a real-time measurement of cell migration. Prior to cell seeding, the underside of the wells from the upper chamber was coated with 25 μL of 0.15% gelatin in PBS and incubated for 1 h at 37° C. The lower chamber was filled with serum-free medium. The upper chamber of each well was filled with 100 μL of SKOV3-Luciferase cells ($2.5 \times 10^5$ cells/mL) pre-treated for 2 hours with or without conjugated-Docetaxel (2 μM) or free Docetaxel (2 μM). After 30 min of adhesion, cell migration was monitored every 5 min for 8 h. The impedance value was measured by the RTCA DP Instrument and was expressed as an arbitrary unit called the Cell Index which reflecting the amount of migration-active cells. Each experiment was performed in duplicate wells.

Example 7

Iodination of Conjugate

Peptides were iodinated with standard procedures using iodo-beads from Sigma. Katana-peptides were diluted in 0.1M phosphate buffer, pH 6.5 (PB). Two iodo-beads were used for each protein. These beads were washed twice with 3 ml of PB on a whatman filter and re-suspended in 60 μl of PB. $^{125}$I (1 mCi) from Amersham-Pharmacia biotech was added to the bead suspension for 5 min at room temperature. The iodination for each peptide was initiated by the addition of 100 μg (80-100 μl). After an incubation of 10 min at room temperature, the free iodine was removed by HPLC.

Example 8

Drug Accumulation in MDCK-MDR1

Cellular uptake of [$^3$H]-Docetaxel and [$^{125}$I]-Docetaxel-Katana peptide conjugate was measured in P-gp-overexpressing MDCK-MDR1 cells, grown in 24-well plates. Cells were washed three times with PBS and preincubated for 30 min at 37° C. in culture medium without serum with or without the P-gp inhibitor Cyclosporin A (10 μM). Radio-labelled molecules (50 nM) were then added for 60 min. The cells were rapidly washed three times with ice-cold PBS and then lysed in 500 μL of 0.1 M NaOH. The amount of radiolabelled molecules retained in the cells was counted by β-scintillation counting (Packard model 1900 TR). An aliquot of cell lysate was used in parallel to determine cellular protein concentration.

Example 9

Xenograft Tumour Model

SKOV3 cancer cells ($2.5 \times 10^6$ cells) expressing luciferase were implanted in the right flank of mice. Tumour growth was monitored using near infrared (NiR) imaging system from Carestream by injecting the luciferase substrate luciferin. Mice were treated with Docetaxel and Katana-drug conjugate (KBA-105) at an equivalent dose of Docetaxel (10 mg/kg/week). Docetaxel treatment was stopped after 3 injections due to body weight loss (around −20%). Treatment with KBA-105 was better tolerated since body weight of mice treated at an equivalent dose was unaffected even after 5 treatments. Luminescence associated with tumour growth of SKOV3/Luc cancer cells was quantified as a function of post-treatment days with the instrument software.

Example 10

Pharmacokinetics and Tissue Distribution

The Docetaxel-Katana peptide conjugate was radiolabeled with [$^{125}$I]— using iodobeads. After radiolabeling free iodine was remove. Mice were injected with Docetaxel-[$^{125}$I]-Katana peptide conjugate at 5 mg/kg. Plasma was collected at the indicated times. After 1, 2 and 24 hours some mice were perfused with saline, sacrificed and tissues were collected. Radioactivity in the plasma and tissues were measured in a radioactivity counter and results were calculated and expressed in terms of μl/ml for the plasma or ng/g of tissues.

Example 11

Synthesis of Docetaxel-Katana Peptide (KBA-106) Conjugate

DoceSuOH

DIEA (0.21 ml, 1.2 mmol) was added dropwise to a suspension of Docetaxel (0.81 g, 1.0 mmol) and succinic anhydride (105 mg, 1.05 mmol) in DMSO (5 ml) under stirring. The mixture was stirred at room temperature and monitored by UPLC-MS. After 2 h, the reaction was complete. The solvent was removed, and the resulting residue was dissolved in DCM and loaded on Biotage silica column for purification. DoceSuOH was obtained as a white powder after lyophilization, UPLC-MS purity>95%.

KBP106-(SuDoce)$_2$

DIEA (0.234 mmol) was added dropwise to a solution of DoceSuOH (213 mg, 0.234 mmol) and TBTU (75 mg, 0.234 mmol) in DMSO (3-4 ml) in order to preactivate the DoceSuOH. The completion of preactivation was monitored by UPLC-MS, then a solution of KBP106 (120 mg, 0.062 mmol) in DMSO (0.2 ml) was added. The mixture was stirred at room temperature. The reaction was monitored by UPLC-MS until completion. The reaction mixture was purified using 30RPC resin column and an AKTA purifier system (10% to 80% ACN) to give KBP106-(SuDoce)2 (145 mg) as white powder after lyophilization, UPLC-MS purity >95%.

Example 12

Synthesis of Doxorubicin-Katana Peptide (KBA-106) Conjugate

Doxuribicin Fmoc-DmgOH

In order to incorporate the linker Dmg on Doxorubicin, the free primary amine in the sugar of Doxo needs first to be protected by an Fmoc group. This DoxoFmoc intermediate was purified on Biotage system. DIEA (0.21 ml, 1.2 mmol) was then added dropwise to a suspension of DoxoFmoc (0.81 g, 1.0 mmol) and dimethyl glutaric (Dmg) anhydride (105 mg, 1.05 mmol) in DMSO (x ml) under stirring. The mixture was stirred at room temperature and the reaction was monitored by UPLC-MS. After completion, the solvent was removed, and the resulting residue was dissolved in DCM and loaded on Biotage silica column for purification. DoxoFmoc-DmgOH was obtained as a reddish powder after lyophilization, UPLC-MS-MS purity >95%.

KBB106-(Dmg-FmocDoxo)$_2$ Conjugate

DIEA (0.234 mmol) was added dropwise to a solution of DmgOH-FmocDoxo (27.3 mg, 0.03 mmol) and TBTU (9.6 mg, 0.03 mmol) in DMSO (3-4 ml) in order to preactivate the DmgOH-FmocDoxo. The completion of preactivation was monitored by UPLC-MS, then a solution of KBP106 (16 mg, 0.008 mmol) in DMSO (0.2 ml) was added. The mixture was stirred at room temperature. The reaction was monitored by UPLC-MS until completion. The reaction mixture was the purified using 30RPC resin column and an AKTA purifier system (10% to 80% ACN; 0.1 Formic acid) to give KBP106-(DmgOH-FmocDoxo)2.

Fmoc Deprotection from KBP106-Dmg-FmocDoxo

Dmg-FmocDoxo (50 mg) was dissolved in 1.5 ml of DMSO and 10 µl of piperidine was added. The mixture turned purple instantaneously and the removal of the Fmoc group from the Doxo moiety was monitored by UPLC-MS. Deprotection was completed in about 10 minutes. To remove the free Fmoc group and piperidine, the mixture was then loaded directly on a 30RPC resin column for purification using an AKTA purifier system with a gradient of 10-80% ACN; 0.1 Formic Acid). The KBP106-Dmg-Doxo was obtained as a reddish powder, UPLC-MS purity >95%.

Example 13

Synthesis of Curcumin-Katana Peptide (KBA-106) Conjugate

Dmg (1.5 equivalent) was added to a solution of Curcumin (0.5 g) in pyridine (4 ml). The mixture was stirred under reflux at 65° C. and the reaction was monitored by UPLC-MS. After Dmg incorporation, the solvent was removed, and the resulting residue was dissolved in DCM and loaded on Biotage silica column for purification. Cur-DmgOH was obtained as a yellow powder after lyophilization, UPLC-MS purity >95%.

Addition of the NHS Linker to DmgOH

In this second step, the NHS linker was added to DmgOH-Cur. Briefly, a 5 fold excess of NHS (224 mg; 1.95 mmol) and EDC (373 mg; 1.95 mmol) were added to DmgOH-Cur (200 mg; 0.39 mmol) in DMSO. After the completion of NHS incorporation, the mixture was directly loaded on 30RPC resin for purification on an AKTA purifier system (10-80% ACN; 0.1 (YoFA gradient)

KBP106-(DmgCur)$_2$

Conjugation was performed in DMSO 80% (pH 9.8) by adding a solution of KBP106 (50 mg; 0.026 mmol) to NHS-DmgCur (38 mg; 0.062 mmol) dissolve in DMSO. The mixture was stirred at room temperature and the conjugation was monitored by UPLC-MS. The reaction mixture was the purified using 30RPC resin column and an AKTA purifier system (10% to 80% ACN; 0.1 Formic acid) to give KBP106-(DmgCur)2 as yellow powder after lyophilization, UPLC-MS purity >95%.

Example 14

Synthesis of Cabazitaxel-Katana Peptide (KBA-106) Conjugate

Cabazitaxel-SuOH

DIEA (0.21 ml, 1.2 mmol) was added dropwise to a suspension of Cabazitaxel (0.81 g, 1.0 mmol) and succinic anhydride (105 mg, 1.05 mmol) in DMSO (x ml) under stirring. The mixture was stirred at room temperature and monitored by UPLC-MS. After 2 h, the reaction was complete. The solvent was removed, and the resulting residue was dissolved in DCM and loaded on Biotage silica column for purification. Cabazitaxel-SuOH was obtained as a white powder after lyophilization, UPLC-MS-MS purity >95%.

KBP106-(SuCabazitaxel)$_2$

DIEA (0.234 mmol) was added dropwise to a solution of CabazitaxelSuOH (219 mg, 0.234 mmol) and TBTU (75 mg, 0.234 mmol) in DMSO (3-4 ml) in order to preactivate the CabazitaxelSuOH. The completion of preactivation was monitored by UPLC-MS, then a solution of KBP106 (120 mg, 0.062 mmol) in DMSO (0.2 ml) was added. The mixture was stirred at room temperature. The reaction was monitored by UPLC-MS until completion. The reaction mixture was purified using 30RPC resin column and an AKTA purifier system (10% to 80% ACN) to give KBP106-(SuCabazitaxel)2 (150 mg) as white powder after lyophilization, UPLC-MS-MS purity >95%.

Example 15

Synthesis of Docetaxel-Katana Peptide (KBA-105) Conjugate

A 2 steps process:
1. Addition of the linker on Docetaxel
   Addition of succinic acid (overnight)
   Purification on Biotage (1 hour)
   Evaporation of the solvents (30 min)
2. Conjugation
   Activation of the docetaxel with TBTU (5-10 min)
   Addition of the peptide
   Reaction in DMF (no need to follow the pH)
   Reaction time 30 min
   Purification on 30 RPC followed by lyophilization at −80° C.

Overall yields around 75%
Purity >95%.

Example 16

Synthesis of Doxorubicin-Katana Peptide (KBB-106) Conjugate

A 4 steps process:
1. Addition of Fmoc on the Doxorubicin free amine
2. Incorporation of the linker on Doxorubicin-Fmoc intermediate
   Dimethyl glutaric acid (DMG) linker
   Purification of Doxorubicin(Fmoc)-DMG on Akta followed by lyophilization
3. Conjugation
   Activation of the Doxorubicin-DMG with TBTU (5-10 min)
   Addition of the peptide
   Reaction in DMSO (no need to follow the pH)
   Reaction time 30 min
   Purification on AKTA (30 RPC resin) followed by lyophilization
4. Deprotection of the Fmoc group with piperidin (5-10 min) followed by purification Overall yields around 42%
Purity >95%.

The embodiments of the paragraphs of the present disclosure are presented in such a manner in the present disclosure so as to demonstrate that every combination of embodiments, when applicable, can be made. These embodiments have thus been presented in the description in a manner equivalent to making dependent claims for all the embodiments that depend upon any of the preceding claims (covering the previously presented embodiments), thereby demonstrating that they can be combined together in all possible manners. For example, all the possible combinations, when applicable, between the embodiments of the paragraphs of the present disclosure are hereby covered.

REFERENCES

1. Bonavia R, Inda M M, Cavenee W K, Furnari F B. Heterogeneity maintenance in glioblastoma: a social network. Cancer Res. 2011, 71:4055-4060.
2. Corbin E M, Morrison S J Tumour heterogeneity and cancer cell plasticity. Nature 2013, 501, 328-337.
3. Diaz Jr L A, Williams R T, Wu J, Kinde I, Hecht J R, Berlin J, Allen B, Bozic I,
4. Fisher R, Pusztai L, Swanton C. Cancer heterogeneity: implications for targeted therapeutics. British Journal of Cancer. 2013, 108; 479-485.
5. Fodale V, Pierobon M, Liotta L, Petricoin E. Mechanism of cell adaptation: when and how do cancer cells develop chemoresistance? Cancer J 2011; 17:89-95.
6. Ghaemimanesh F, Ahmadian G, Talebi S, Zarnani A H. Behmanesh M, Hemmati S, Hadavi R, Jeddi-Tehrani M, Farzi M, Akhondi M M, Rabbani H. The Effect of Sortilin Silencing on Ovarian Carcinoma Cells. Avicenna J Med Biotech. 2014; 6:169-177.
7. Gillet J P, Gottesman M M. Mechanisms of multidrug resistance in cancer. Methods Mol Biol 2010; 596:47-76.
8. Gore M E, Larkin J M Challenges and opportunities for converting renal cell carcinoma into a chronic disease with targeted therapies. Br J Cancer 2011, 104:399-406.
9. Hemmati S., Zarnani A H, Mahmoudi A R, Sadeghi M R, Soltanghoraee H, Mohammad Mehdi Akhondi M M, Tarahomi M, Jeddi-Tehrani M, Hodjattallah Rabbani H. Ectopic Expression of Sortilin 1 (NTR-3) in Patients with Ovarian Carcinoma. Avicenna J Med Biotech. 2009; 1:125-131.
10. Heppner G H. Tumor heterogeneity. Cancer Res. 1984, 44: 2259-2265.
11. Hosseini A, Ghorbani A. Cancer therapy with phytochemicals: evidence from clinical studies. Avicenna J Phytomed. 2015; 5:84-97.
12. Kjolby M, Nielsen M S, Petersen C M. Sortilin, encoded by the cardiovascular risk gene SORT1, and its suggested functions in cardiovascular disease. Curr Atheroscler Rep. 2015 April; 17(4):496.
13. Kreso A, O'Brien C A, van Galen P, Gan O I, Notta F, Brown A M, et al. Variable clonal repopulation dynamics influence chemotherapy response in colorectal cancer. Science 2013; 339:543-548.
14. Marusyk A, Polyak K. Cancer. Cancer cell phenotypes, in fifty shades of grey. Science 2013; 339:528-529.
15. Marusyk A, Polyak K. Tumor heterogeneity: causes and consequences. Biochim Biophys Acta 2010, 1805:105-117.
16. Mortensen M B et al. Targeting sortilin in immune cells reduces proinflammatory cytokines and atherosclerosis. J Clin Invest. 2014; 124(12): 5317-5322.
17. Nowell P C. The clonal evolution of tumor cell populations. Science, 1976, 194: 23-28.
18. Navarro, V., Vincent, J, and Mazella, J. Shedding of the luminal domain of the neurotensin receptor-3/Sortilin in the HT29 cell line. Biochem. Biophys. Res. Commun, 298, 760-764.
19. Orit Lavi, James M. Greene, Doron Levy, and Michael M. Gottesman. The Role of Cell Density and Intratumoral Heterogeneity in Multidrug Resistance. Cancer Res.; 2013 73(24); 7168-7175.
20. Prabakaran et al. Mannose 6-phosphate receptor and sortilin mediated endocytosis of a-galactosidase A in kidney endothelial cells. PLoS One. 2012; 7(6):e39975.
21. Reiter J G, Nowak M A, Kinzler K W, Oliner K S, Vogelstein B. The molecular evolution of acquired resistance to targeted EGFR blockade in colorectal cancers. Nature 2012, 486:537-540.
22. Roselli S, Pundavela J, Demont Y, Faulkner S, Keene S, Attia J, Jiang C C, Zhang X D, Walker M M, Hondermarck H. Sortilin is associated with breast cancer aggressiveness and contributes to tumor cell adhesion and invasion. Oncotarget. 2015; 6:10473-10486.
23. Sanz-Moreno V, Gadea G, Ahn J, Paterson H, Marra P, Pinner S, et al. Rac activation and inactivation control plasticity of tumor cell movement. Cell 2008; 135:510-523.
24. Silva R, Vilas-Boas V, Carmo H, Dinis-Oliveira R J, Carvalho F, de Lourdes Bastos M, Remião. Modulation of P-glycoprotein efflux pump: induction and activation as a therapeutic strategy. Pharmacol Ther. 2015; 149:1-123.
25. Zhou S F. Structure, function and regulation of P-glycoprotein and its clinical relevance in drug disposition. Xenobiotica. 2008; 38:802-832.

What is claimed is:

1. A peptide compound having: at least 92% sequence identity to a compound of formula (VI), at least 80% sequence identity to a compound of formula (X), or at least 85% sequence identity to a compound of formula (XI):

```
                                        (SEQ ID NO: 6)
    IKLSGGVQAKAGVINMFKSESY
    (VI)

(SEQ ID NO: 10)
    GVRAKAGVRN(Nle)FKSESY
    (X)

(SEQ ID NO: 11)
    YKSLRRKAPRWDAPLRDPALRQLL
    (XI)
``` wherein at least one protecting group and/or at least one agent is optionally connected to said peptide compound at an N-terminal position of said peptide compound, at a C-terminal position of said peptide compound, at a free amine of said peptide compound, at a free —SH of said peptide compound, or at a free carboxyl of said peptide compound.

2. The peptide compound of claim 1, wherein the peptide compound is represented by formula (VI) and consists of the amino acid sequence of SEQ ID NO: 6.

3. The peptide compound of claim 1, wherein the peptide compound is represented by formula (VII) and consists of the amino acid sequence of SEQ ID NO: 7.

4. The peptide compound of claim 1, wherein the peptide compound is represented by formula (VIII) and consists of the amino acid sequence of SEQ ID NO: 8.

5. The peptide compound of claim 1, wherein the peptide compound is represented by formula (IX) and consists of the amino acid sequence of SEQ ID NO: 9.

6. The peptide compound of claim 1, wherein the peptide compound is represented by formula (X) and consists of the amino acid sequence of SEQ ID NO: 10.

7. The peptide compound of claim 1, wherein the peptide compound is represented by formula (XI) and consists of the amino acid sequence of SEQ ID NO: 11.

8. The peptide compound of claim 1, wherein the peptide compound is represented by formula (XII) and consists of the amino acid sequence of SEQ ID NO: 12.

9. The peptide compound of claim 1, wherein the peptide compound is represented by formula (XIII) and consists of the amino acid sequence of SEQ ID NO: 13.

10. The peptide compound of claim 1, wherein the peptide compound has at least 90% sequence identity to the compound of formula (X) or formula (XI).

11. The peptide compound of claim 1, wherein the peptide compound is connected to the at least one agent.

12. The peptide compound of claim 11, wherein the peptide compound is connected to the at least one agent by a linker.

13. The peptide compound of claim 1, wherein the peptide compound is connected to at least one protecting group.

14. The peptide compound of claim 13, wherein the at least one protecting group is acetyl or succinyl.

15. The peptide compound of claim 14, wherein the peptide compound is connected to the at least one protecting group to form a peptide compound-protecting group conjugate represented by Formula (XXXVIII), Formula (XXXIX), Formula (XXXX), Formula (XXXXI), Formula (XXXXII) or Formula (XXXVI):

```
                                        (SEQ ID NO: 14)
    Acetyl-GVRAKAGVRNMFKSESY
    (XXXVIII)

(SEQ ID NO: 15)
    Acetyl-GVRAKAGVRN(Nle)FKSESY
    (XXXIX)

(SEQ ID NO: 16)
    Acetyl-YKSLRRKAPRWDAPLRDPALRQLL
    (XXXX)

(SEQ ID NO: 17)
    Acetyl-YKSLRRKAPRWDAYLRDPALRQLL
    (XXXXI)

(SEQ ID NO: 18)
    Acetyl-YKSLRRKAPRWDAYLRDPALRPLL
    (XXXXII)

Succinyl-IKLSGGVQAKAGVINMFKSESY
    (XXXVI),
``` that comprises the peptide compound having SEQ ID NO: 6 connected to a succinyl group at the N-terminal end.

16. The peptide compound of claim 11, wherein the peptide compound is connected to at least one therapeutic agent, labelling agent and/or imaging agent.

17. The peptide compound of claim 16, wherein the at least one therapeutic agent is an anticancer agent.

18. A method of selectively targeting at least one agent to a sortilin-expressing cell in a population of cells, comprising contacting the peptide compound of claim 11 with the population of cells.

19. The method of claim 18, wherein the at least one agent is at least one anticancer agent and the sortilin-expressing cell is a cancer cell.

20. A method of increasing cellular internalization of at least one agent in a sortilin-expressing cell, comprising contacting the peptide compound of claim 11 with the sortilin-expressing cell.

21. The method of claim 20, wherein the at least one agent is at least one anticancer agent and the sortilin-expressing cell is a cancer cell.

* * * * *